United States Patent
Morita et al.

(10) Patent No.: US 8,247,569 B2
(45) Date of Patent: Aug. 21, 2012

(54) CYCLOHEXANE DERIVATIVE AND PHARMACEUTICAL USE THEREOF

(75) Inventors: Yasuhiro Morita, Kamakura (JP); Katsuhiko Iseki, Kamakura (JP); Yuji Sugawara, Kamakura (JP); Hideyuki Tsutsui, Kamakura (JP); Shunsuke Iwano, Kamakura (JP); Naoki Izumimoto, Kamakura (JP); Tadamasa Arai, Kamakura (JP); Hidetoshi Noda, Kamakura (JP); Chihiro Yoshida, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/126,901

(22) PCT Filed: Oct. 30, 2009

(86) PCT No.: PCT/JP2009/068644
§ 371 (c)(1),
(2), (4) Date: Apr. 29, 2011

(87) PCT Pub. No.: WO2010/050577
PCT Pub. Date: May 6, 2010

(65) Prior Publication Data
US 2011/0201650 A1    Aug. 18, 2011

(30) Foreign Application Priority Data

Oct. 31, 2008 (JP) .................................. 2008-281258
Jul. 29, 2009 (JP) .................................. 2009-176619

(51) Int. Cl.
C07D 401/02 (2006.01)
C07D 277/20 (2006.01)
C07D 263/30 (2006.01)
C07D 231/10 (2006.01)

(52) U.S. Cl. ..................... 546/275.4; 548/202; 548/235; 548/377.1

(58) Field of Classification Search ............... 546/275.4; 548/202, 235, 377.1
See application file for complete search history.

(56) References Cited

U.S. PATENT DOCUMENTS

| 6,025,375 A * | 2/2000 | Taniguchi et al. ............ 514/374 |
| 6,436,966 B1 | 8/2002 | Ohkawa et al. |
| 2004/0116475 A1 | 6/2004 | Shirai et al. |

FOREIGN PATENT DOCUMENTS

| JP | 11-193281 A | 7/1999 |
| JP | 2007-197324 A | 8/2007 |
| WO | 99/01449 A1 | 1/1999 |
| WO | 00/66562 A1 | 11/2000 |
| WO | 2004/050632 A1 | 6/2004 |
| WO | 2007/111323 A1 | 10/2007 |
| WO | 2008/105383 A1 | 9/2008 |

OTHER PUBLICATIONS

Shoten, H., "Development of Drugs," *Iyakuhin no Kaihatsa*, 1990, vol. 7, pp. 163-198 and 1 sheet of partial English translation.
Mitsuru, H., "Chemical Structures of Prodrugs and Their Classification," *Prog. Med.*, 1985, vol. 5, pp. 2157-2161 and 1 sheet of partial English translation.
Protective Groups in Organic Synthesis, Third Edition, Wiley-Interscience, pp. 298-303 and 316-319.
G.K. Surya Prakash et al., "Fluoride-Induced Trifluoromethylation of Carbonyl Compounds with Trifluoromethyltrimethylsilane (TMS-$CF_3$). A Trifluormethyide Equivalent," *J. Am. Chem. Soc.*, 1989, vol. 39, pp. 393-395.
Franklin A. Davis et al., "Applications of Oxaziridines in Organic Synthesis," *Tetrahedron*, 1989, vol. 45, No. 18, pp. 5703-5742.
Olivier Dirat et al., "Regioselective synthesis of 4-(2-alkyl-5-methyl-2$H$-pyrazol-3-yl)-piperidines," Tetrahedron Letters, 2006, vol. 47, pp. 1729-1731.

* cited by examiner

*Primary Examiner* — Rebecca Anderson
*Assistant Examiner* — Samantha Shterengarts
(74) *Attorney, Agent, or Firm* — DLA Piper LLP (US)

(57) ABSTRACT

A compound has a strong analgesic action against both nociceptive pain and neuropathic pain and has less side effects, and is medically useful. The compound includes cyclohexane derivatives represented by the following compound, or pharmaceutically acceptable salts thereof or prodrugs thereof.

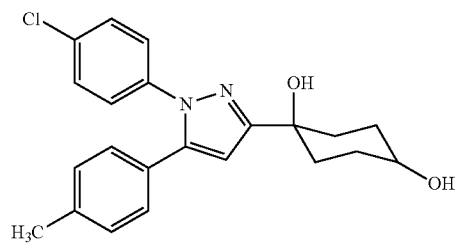

10 Claims, 4 Drawing Sheets

CYCLOHEXANE DERIVATIVE AND PHARMACEUTICAL USE THEREOF

RELATED APPLICATIONS

This is a §371 of International Application No. PCT/JP2009/068644, with an international filing date of Oct. 30, 2009 (WO 2010/050577 A1, published May 6, 2010), which is based on Japanese Patent Application Nos. 2008-281258, filed Oct. 31, 2008, and JP 2009-176619, filed Jul. 29, 2009, the subject matter of which is incorporated by reference.

TECHNICAL FIELD

This disclosure relates to cyclohexane derivatives and their medical use.

BACKGROUND

Pain is an experience that is accompanied by an uncomfortable sense or uncomfortable emotion, which occurs when a tissue is damaged or tissue may be damaged. Pain is roughly divided into nociceptive pain and neuropathic pain depending on its cause.

The term "nociceptive pain" means a pain caused when a tissue of the body was damaged or a nociceptive stimulus that may cause such damage was given to a tissue of the body, and a nociceptive pain is caused through a nociceptor. Examples of the nociceptive pain include physiological pains and inflammatory pains.

The term "neuropathic pain" means a pathological pain due to a functional abnormality of the peripheral nerve or the central nervous system itself, and a neuropathic pain is caused by a direct damage to, or pressure on, a nerve without a nociceptive stimulus to a nociceptor.

Examples of therapeutic drugs of nociceptive pain include nonsteroidal anti-inflammatory drugs (NSAIDs) and narcotic analgesics (e.g., opioid), and examples of therapeutic drugs of neuropathic pain include anticonvulsants, antidepressants, antianxiety agents, and antiepileptics such as gabapentin and pregabalin.

Further, in recent years, it has been reported that a pyrazole derivative is effective as an analgesic or a therapeutic drug for neuropathic pain (WO 08/105,383) and that the cyclohexane derivative of the following Formula having sulfonyl on an aromatic ring linked to a pyrazole ring has an analgesic effect on neuropathic pain (WO 00/066562):

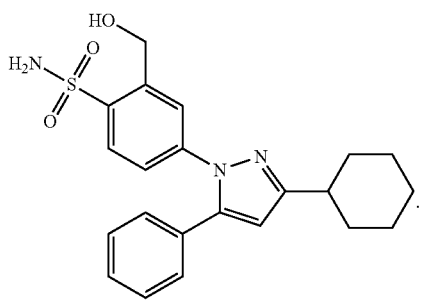

However, in terms of cyclohexane derivatives, whether or not compounds having no sulfur functional group on the aromatic ring linked to the pyrazole ring have an analgesic action has not been revealed, and the possibility that such compounds have an analgesic effect has not been suggested so far.

Further, it is known that administration of a nonsteroidal anti-inflammatory drug is accompanied by side effects such as gastrointestinal dysfunction and renal disorder, and administration of a narcotic analgesic is accompanied by side effects such as constipation, drowsiness, nausea and vomiting. Further, it has been pointed out that administration of the above-described therapeutic drugs for neuropathic pain is frequently accompanied by central nervous system side effects such as vertigo, nausea and vomiting, and therefore that their long-term administration is difficult.

Further, since the mechanism by which pain is caused is largely different between nociceptive pain and neuropathic pain, a compound having a strong analgesic effect on both of the pains has not been developed so far.

Thus, it could be helpful to provide a compound having a strong analgesic effect on both nociceptive pain and neuropathic pain and showing less side effects, and its medical use.

SUMMARY

We discovered cyclohexane derivatives having a strong analgesic effect on both nociceptive pain and neuropathic pain, which cyclohexane derivatives are excellent in metabolic stability and safety.

That is, we provide a cyclohexane derivative represented by Formula (I):

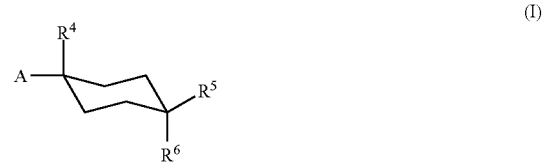

wherein

A represents a substituent represented by Formula (IIa) or (IIb):

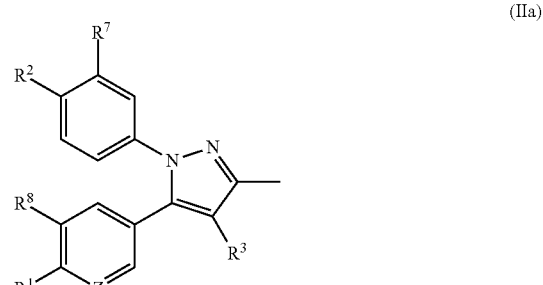

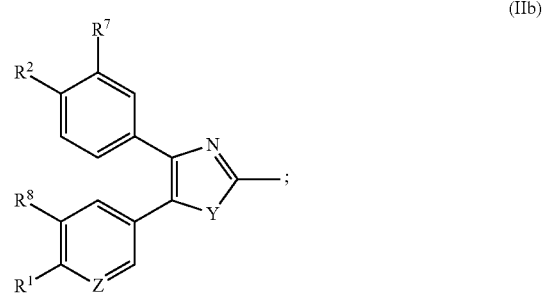

$R^1$ and $R^2$ each independently represent a hydrogen atom, chlorine atom, $C_1$-$C_3$ haloalkyl, $C_1$-$C_4$ alkyl, $C_1$-$C_4$ alkoxy or cyano;

$R^3$ represents a hydrogen atom or chlorine atom;

$R^4$ represents a fluorine atom, hydroxymethyl or hydroxyl;

$R^5$ and $R^6$ each independently represent a hydrogen atom, fluorine atom, $C_1$-$C_3$ haloalkyl, carboxyl, methoxycarbonyl, ethoxycarbonyl, $C_1$-$C_4$ alkoxy, hydroxyl or $C_2$-$C_5$ alkylcarbonyloxy, or $R^5$ and $R^6$ may together form an oxo group;

$R^7$ and $R^8$ each independently represent a hydrogen atom or fluorine atom;

Y represents an oxygen atom or sulfur atom; and

Z represents a nitrogen atom or methane or a pharmaceutically acceptable salt thereof or a prodrug thereof.

Preferably, in the above cyclohexane derivative, $R^1$ and $R^2$ each independently represent a hydrogen atom, chlorine atom, $C_1$-$C_3$ haloalkyl, $C_1$-$C_4$ alkyl or $C_1$-$C_4$ alkoxy; $R^5$ and $R^6$ each independently represent a hydrogen atom, fluorine atom, $C_1$-$C_3$ haloalkyl, carboxyl, $C_1$-$C_4$ alkoxy, hydroxyl or $C_2$-$C_5$ alkylcarbonyloxy, or $R^5$ and $R^6$ may together form an oxo group; and $R^7$ and $R^8$ are hydrogen atoms.

More preferably, in the above cyclohexane derivative, $R^1$ and $R^2$ each independently represent trifluoromethyl, methyl or methoxy; $R^3$ represents a hydrogen atom; $R^4$ represents hydroxymethyl or hydroxyl; $R^5$ and $R^6$ each independently represent a hydrogen atom, fluorine atom, trifluoromethyl, carboxyl, methoxy, hydroxyl or acetyloxy (or $R^5$ and $R^6$ may together form an oxo group).

We also provide a pharmaceutical comprising an effective amount of the above cyclohexane derivative or a pharmaceutically acceptable salt thereof or a prodrug thereof.

The pharmaceutical is preferably an analgesic, more preferably a therapeutic drug for neuropathic pain and/or nociceptive pain. More preferably, the above pharmaceutical has a strong analgesic effect also on diabetic neuropathic pain and can be suitably used as a therapeutic drug for diabetic neuropathic pain.

Since the cyclohexane derivative or a pharmaceutically acceptable salt thereof or a prodrug thereof exerts an analgesic effect on nociceptive pain and neuropathic pain as well as diabetic neuropathic pain, a therapeutic effect for pain can be exerted in a patient suffering from pain whose etiology is unknown. Further, the cyclohexane derivative or a pharmaceutically acceptable salt thereof or a prodrug thereof has a strong analgesic effect and less side effects, it can be administered as a pharmaceutical for a wide range of pain symptoms including diabetic neuropathic pain.

DETAILED DESCRIPTION

Figure 1:
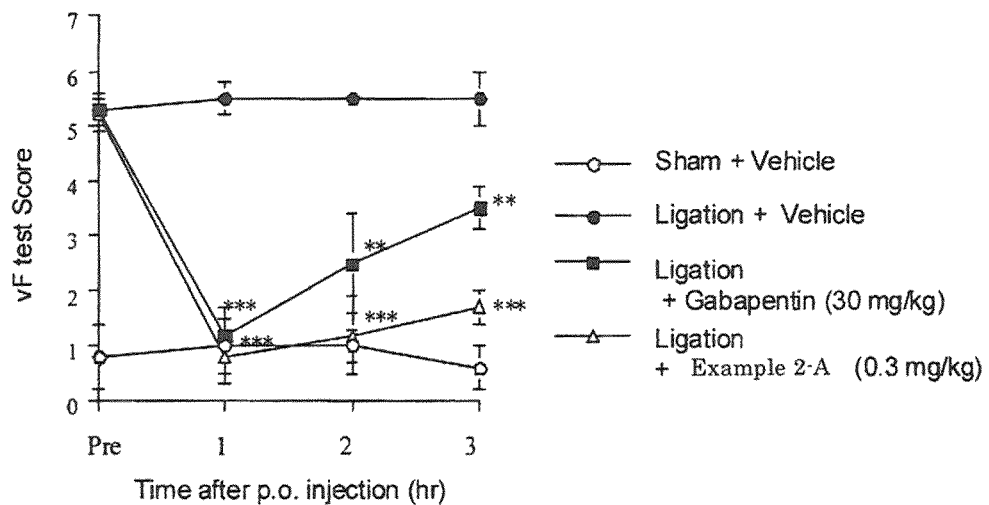
FIG. 1 is a diagram showing the effect of the compound of Example 2-A in a mouse partial sciatic nerve ligation model (oral administration).
Figure 2:
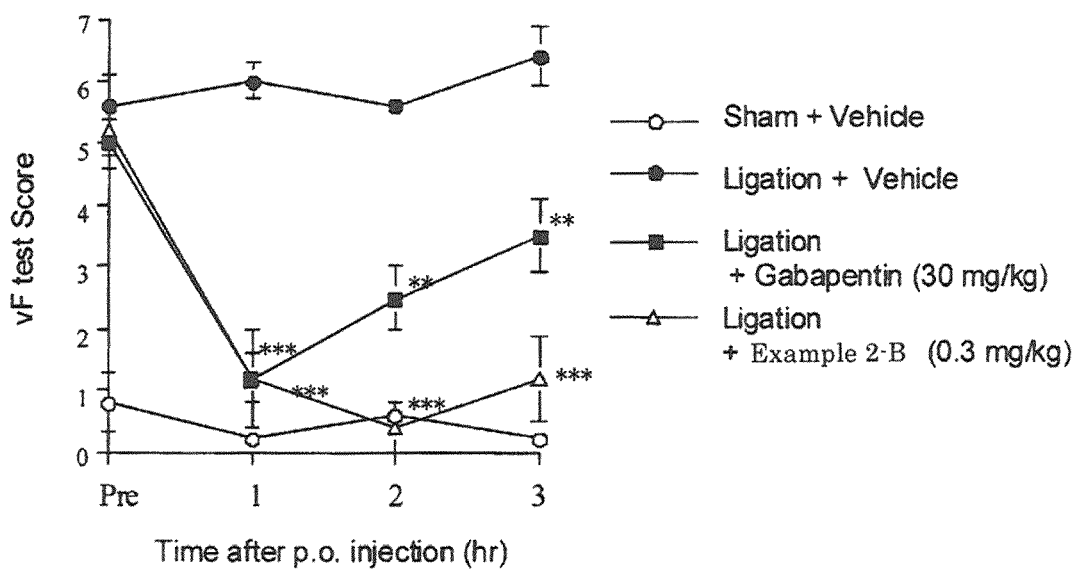
FIG. 2 is a diagram showing the effect of the compound of Example 2-B in a mouse partial sciatic nerve ligation model (oral administration).
Figure 3:
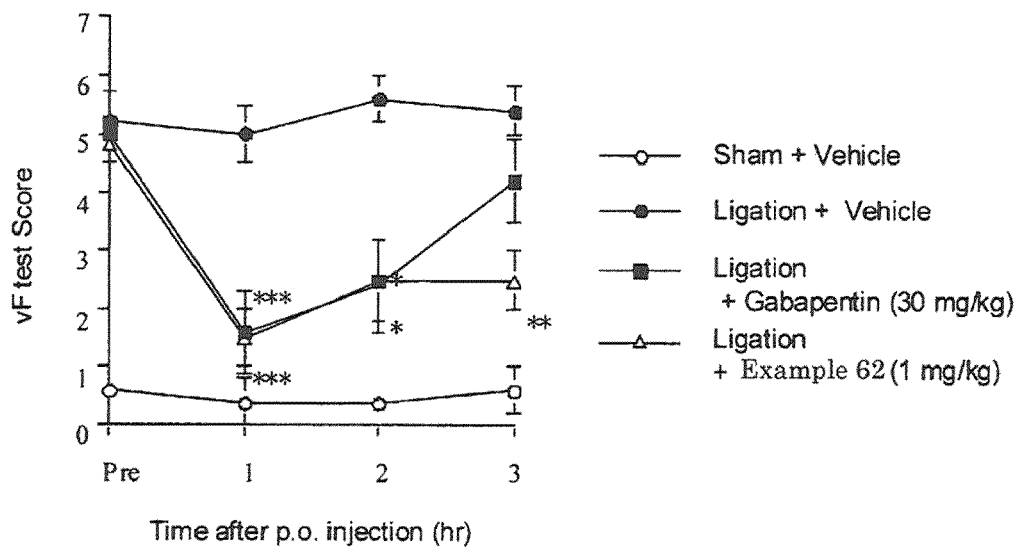
FIG. 3 is a diagram showing the effect of the compound of Example 62 in a mouse partial sciatic nerve ligation model (oral administration).
Figure 4:
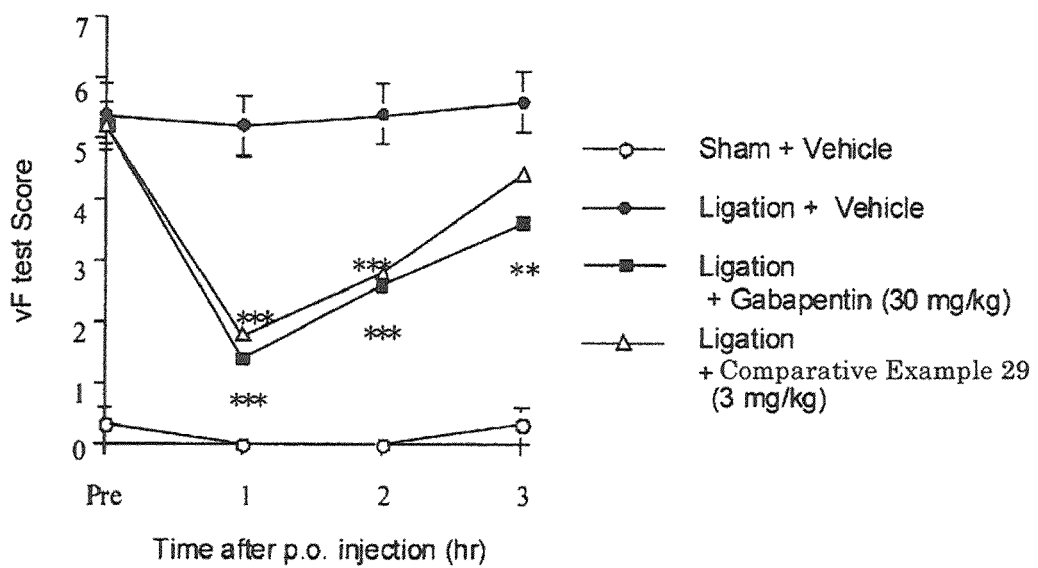
FIG. 4 is a diagram showing the effect of the compound of Comparative Example 29 in a mouse partial sciatic nerve ligation model (oral administration).

The following terms used in the specification are defined as described below unless otherwise specified.

The cyclohexane derivative is represented by Formula (I):

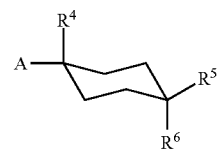

wherein

A represents a substituent represented by Formula (IIa) or (IIb) below:

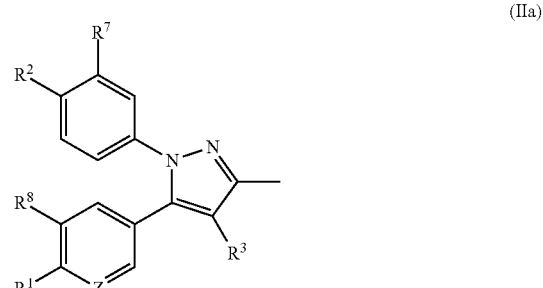

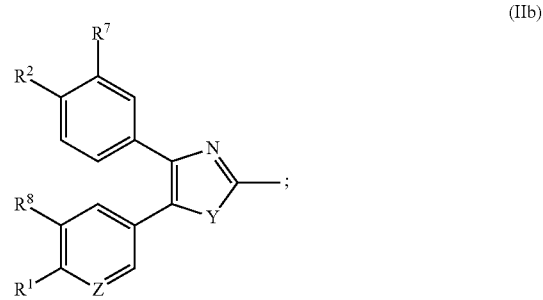

$R^1$ and $R^2$ each independently represent a hydrogen atom, chlorine atom, $C_1$-$C_3$ haloalkyl, $C_1$-$C_4$ alkyl, $C_1$-$C_4$ alkoxy or cyano;

$R^3$ represents a hydrogen atom or chlorine atom; $R^4$ represents a fluorine atom, hydroxymethyl or hydroxyl;

$R^5$ and $R^6$ each independently represent a hydrogen atom, fluorine atom, $C_1$-$C_3$ haloalkyl, carboxyl, methoxycarbonyl, ethoxycarbonyl, $C_1$-$C_4$ alkoxy, hydroxyl or $C_2$-$C_5$ alkylcarbonyloxy, or $R^5$ and $R^6$ may together form an oxo group;

$R^7$ and $R^8$ each independently represent a hydrogen atom or fluorine atom;

Y represents an oxygen atom or sulfur atom; and

Z represents a nitrogen atom or methane.

"C₁-C₄ alkyl" means a linear, branched or cyclic alkyl group having 1 to 4 carbon atoms, and examples thereof include methyl, ethyl, n-propyl, isopropyl, cyclopropyl, cyclopropylmethyl, n-butyl, sec-butyl and tert-butyl.

"C₁-C₄ alkoxy" means a linear, branched or cyclic alkyloxy group having 1 to 4 carbon atoms, and examples thereof include methoxy, ethoxy, n-propyloxy, isopropyloxy, cyclopropyloxy, n-butoxy, sec-butoxy and tert-butoxy.

"C₁-C₃ haloalkyl" means a linear alkyl group having 1 to 3 carbon atoms wherein the hydrogen atoms on the group are partially or entirely substituted with a halogen atom(s) (the halogen atom means a fluorine atom, chlorine atom, bromine atom or iodine atom), and examples thereof include monochloromethyl, monofluoromethyl, difluoromethyl, trifluoromethyl, trichloromethyl and pentafluoroethyl.

Examples of "C₂-C₅ alkylcarbonyloxy" include acetyloxy, ethanoyloxy, propanoyloxy, isopropanoyloxy, butanoyloxy, isobutanoyloxy and pivaloyloxy.

In Formula (I), A preferably represents (IIc).

Y preferably represents a sulfur atom.

$R^1$ and $R^2$ each independently preferably represent a hydrogen atom, chlorine atom, trifluoromethyl, methyl, ethyl, n-propyl, isopropyl, methoxy, ethoxy, n-propyloxy, isopropyloxy or cyano, and more preferably represent trifluoromethyl, methyl or methoxy.

$R^3$ preferably represents a hydrogen atom.

$R^4$ preferably represents hydroxyl.

Preferably, $R^5$ and $R^6$ each independently represent a hydrogen atom, fluorine atom, trifluoromethyl, carboxyl, methoxycarbonyl, ethoxycarbonyl, methoxy, ethoxy, n-propyloxy, isopropyloxy, hydroxyl, acetyloxy, propanoyloxy, butanoyloxy, isobutanoyloxy or pivaloyloxy, or $R^5$ and $R^6$ together form an oxo group. More preferably, $R^5$ and $R^6$ each independently represent a hydrogen atom, fluorine atom, trifluoromethyl, carboxyl, methoxy, hydroxyl or acetyloxy, or $R^5$ and $R^6$ together form an oxo group.

$R^7$ and $R^8$ each independently preferably represent a hydrogen atom or fluorine atom, and more preferably represent a hydrogen atom.

Particular preferred examples of the compounds represented by Formula (I) and pharmaceutically acceptable salts thereof (hereinafter referred to as Compounds (1)) are shown in Table 1, but these do not restrict the scope of the appended claims.

TABLE 1-1

| Compound | Structural formula |
|---|---|
| 1 | |
| 2 | |
| 3 | |
| 4 | |
| 5 | |
| 6 | |
| 7 | |

TABLE 1-1-continued

| Compound | Structural formula |
|---|---|
| 8 | 4-methoxyphenyl / 4-methoxyphenyl pyrazole with cyclohexane bearing OH and OH |
| 9 | 4-methoxyphenyl / 4-methylphenyl pyrazole (4-Cl) with cyclohexane bearing OH, OH |
| 10 | 4-methoxyphenyl / 4-methylphenyl pyrazole with cyclohexane bearing OH, OH, CF₃ |
| 11 | 4-methoxyphenyl / 4-methylphenyl pyrazole with cyclohexane bearing F and OH |
| 12 | 4-methoxyphenyl / 4-methylphenyl pyrazole with cyclohexane bearing OH and OC(O)CH₃ |
| 13 | 4-methoxyphenyl / 4-methylphenyl pyrazole with cyclohexane bearing OH and OCH₃ |
| 14 | 4-methoxyphenyl / 4-methylphenyl pyrazole with cyclohexane bearing CH₂OH and OH |
| 15 | 4-methoxyphenyl / 6-methylpyridin-3-yl pyrazole with cyclohexane bearing OH, OH |
| 16 | 4-methoxyphenyl / 4-methylphenyl pyrazole with cyclohexane bearing OH and CO₂H |

TABLE 1-2

| Compound | Structural formula |
|---|---|
| 17 | 4-methoxyphenyl / 4-methylphenyl pyrazole with cyclohexane bearing OH and two F |
| 18 | 4-methoxyphenyl / 4-(trifluoromethyl)phenyl pyrazole with cyclohexane bearing OH and OH |

TABLE 1-2-continued

| Compound | Structural formula |
|---|---|
| 19 | (4-methoxyphenyl / 4-trifluoromethylphenyl pyrazole with cyclohexane-diol) |
| 20 | (4-methoxyphenyl / 4-methylphenyl pyrazole with cyclohexane-diol, CH2OH) |
| 21 | (4-methoxyphenyl / 4-chlorophenyl pyrazole with cyclohexane-diol) |
| 22 | (4-chlorophenyl / 4-methylphenyl pyrazole with cyclohexane-diol) |
| 23 | (4-chlorophenyl / 4-chlorophenyl pyrazole with cyclohexane-diol) |
| 24 | (4-chlorophenyl / 4-chlorophenyl pyrazole with cyclohexane-diol) |
| 25 | (phenyl / 4-chlorophenyl pyrazole with cyclohexane-diol) |
| 26 | (phenyl / 4-chlorophenyl pyrazole with cyclohexane-diol) |
| 27 | (4-methylphenyl / 4-methylphenyl pyrazole with cyclohexane-diol) |
| 28 | (4-methylphenyl / 4-methylphenyl pyrazole with cyclohexane-diol) |
| 29 | (phenyl / 4-methylphenyl pyrazole with cyclohexane-diol) |
| 30 | (phenyl / 4-methylphenyl pyrazole with cyclohexane-diol) |

TABLE 1-2-continued

| Compound | Structural formula |
|---|---|
| 31 | (4-methoxyphenyl, phenyl pyrazole with cyclohexane-diol; OH, OH) |
| 32 | (4-methoxyphenyl, phenyl pyrazole with cyclohexane-diol; OH, OH) |

TABLE 1-3

| Compound | Structural Formula |
|---|---|
| 33 | (4-methylphenyl, phenyl pyrazole with cyclohexane-diol) |
| 34 | (4-methylphenyl, phenyl pyrazole with cyclohexane-diol) |
| 35 | (4-methylphenyl, 4-methoxyphenyl pyrazole with cyclohexane-diol) |
| 36 | (4-methylphenyl, 4-methoxyphenyl pyrazole with cyclohexane-diol) |

TABLE 1-3-continued

| Compound | Structural Formula |
|---|---|
| 37 | (4-chlorophenyl, 4-methoxyphenyl pyrazole with cyclohexane-diol) |
| 38 | (4-chlorophenyl, 4-methoxyphenyl pyrazole with cyclohexane-diol) |
| 39 | (phenyl, 4-methoxyphenyl pyrazole with cyclohexane-diol) |
| 40 | (phenyl, 4-methoxyphenyl pyrazole with cyclohexane-diol) |
| 41 | (4-methoxyphenyl, 4-methylphenyl thiazole with cyclohexane-diol) |
| 42 | (4-methoxyphenyl, 4-methylphenyl thiazole with cyclohexane-diol) |

TABLE 1-3-continued

| Compound | Structural Formula |
|---|---|
| 43 | 4,5-bis(4-methoxyphenyl)oxazol-2-yl cyclohexane-1,4-diol |
| 44 | 4,5-bis(4-methoxyphenyl)oxazol-2-yl cyclohexane-1,4-diol (isomer) |
| 45 | 4-(4-methoxyphenyl)-5-(4-methylphenyl)thiazol-2-yl 4-trifluoromethyl-cyclohexane-1,4-diol |
| 46 | 4-(4-methoxyphenyl)-5-(4-methylphenyl)thiazol-2-yl 4-trifluoromethyl-cyclohexane-1,4-diol (isomer) |
| 47 | 1-(4-methoxyphenyl)-5-(4-ethylphenyl)pyrazol-3-yl cyclohexane-1,4-diol |
| 48 | 1-(4-methoxyphenyl)-5-(4-ethylphenyl)pyrazol-3-yl cyclohexane-1,4-diol (isomer) |

TABLE 1-4

| Compound | Structural formula |
|---|---|
| 49 | 1-(4-cyanophenyl)-5-(4-methylphenyl)pyrazol-3-yl cyclohexane-1,4-diol |
| 50 | 1-(4-cyanophenyl)-5-(4-methylphenyl)pyrazol-3-yl cyclohexane-1,4-diol (isomer) |
| 51 | 1-(4-methoxyphenyl)-5-(4-cyanophenyl)pyrazol-3-yl cyclohexane-1,4-diol |
| 52 | 1-(4-methoxyphenyl)-5-(4-cyanophenyl)pyrazol-3-yl cyclohexane-1,4-diol (isomer) |
| 53 | 1-(3-fluoro-4-methoxyphenyl)-5-(4-methylphenyl)pyrazol-3-yl cyclohexane-1,4-diol |
| 54 | 1-(3-fluoro-4-methoxyphenyl)-5-(4-methylphenyl)pyrazol-3-yl cyclohexane-1,4-diol (isomer) |

TABLE 1-4-continued

| Compound | Structural formula |
|---|---|
| 55 | ![compound 55: 4-methoxyphenyl-pyrazole with 3-fluoro-4-methylphenyl and dihydroxycyclohexyl substituent] |
| 56 | ![compound 56: 4-methoxyphenyl-pyrazole with 3-fluoro-4-methylphenyl and hydroxy-hydroxymethyl cyclohexyl] |
| 57 | ![compound 57: 4-methoxyphenyl-pyrazole with 4-methylphenyl and hydroxy-CO2CH3 cyclohexyl] |
| 58 | ![compound 58: 4-methoxyphenyl-pyrazole with 4-methylphenyl and hydroxy-CO2Et cyclohexyl] |

In cases where asymmetric carbon atoms exist in Compound (I), all the enantiomers and mixtures thereof are included.

Further, in cases where stereoisomers exist in Compound (I), all the stereoisomers and mixtures thereof are included.

Examples of the "pharmaceutically acceptable salt" include inorganic acid salts such as hydrochloride, sulfate, phosphate and hydrobromide; organic acid salts such as oxalate, malonate, citrate, fumarate, lactiate, malate, succinate, tartarate, acetate, trifluoroacetate, maleate, gluconate, benzoate, ascorbate, methanesulfonate, p-toluenesulfonate and cinnamate; inorganic base salts such as sodium salt, potassium salt, calcium salt, magnesium salt and ammonium salt; and organic base salts such as methylamine salt, diethylamine salt, trimethylamine salt, triethylamine salt, pyridinium salt, triethanolamine salt, ethylenediamine salt and guanidium salt. Further, Compound (I) may form a hydrate, solvate or crystalline polymorph.

Compound (I) can be synthesized, for example, according to the production method described below. The symbols in each reaction formula have the same meanings as those defined above unless otherwise specified.

In cases where the raw material compound has a carboxyl group or a hydroxyl group, a protective group commonly used may be introduced, and the protective group may be removed as required after the reaction. Examples of the protective group of the hydroxyl group include $C_1$-$C_4$ alkyl, phenyl, trityl, $C_1$-$C_4$ aralkyl (e.g., benzyl), acyl (e.g., formyl, acetyl and benzoyl), $C_7$-$C_{10}$ aralkyl-carbonyl (e.g., benzylcarbonyl), and substituted silyl (e.g., trimethylsilyl, triethylsilyl and tert-butyldimethylsilyl). Examples of the protective group of the carboxyl group include $C_1$-$C_4$ alkyl.

The method of removal of the protective group varies depending on the type of the protective group, and the removal can be carried out according to a method described in PROTECTIVE GROUPS IN ORGANIC SYNTHESIS (WILEY-INTER-SCIENCE) or a method corresponding thereto.

In the production method described below, a salt can be used as the raw material compound. Examples of the salt include those described above as pharmaceutically acceptable salts.

Compound (I) obtained by the production method described below can be isolated and purified according to conventional methods, and examples of the methods include solvent extraction, recrystallization and chromatography.

In cases where Compound (I) has optical isomers, stereoisomers, regio isomers and/or rotamers, each of these can be obtained as single compounds by a conventional synthesis method and separation method.

Production Method 1: Production Method of Compound (Ic), Compound (Id), Compound (Ie) and Compound (If)

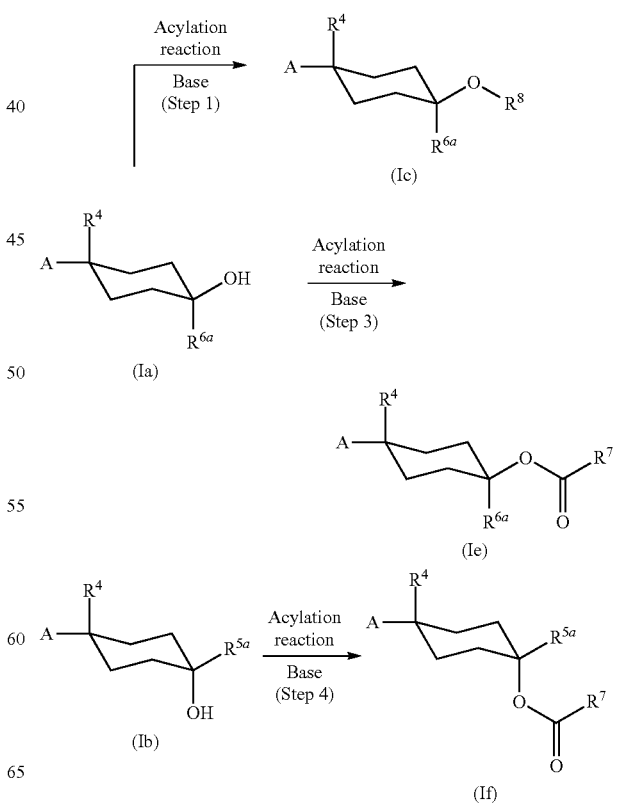

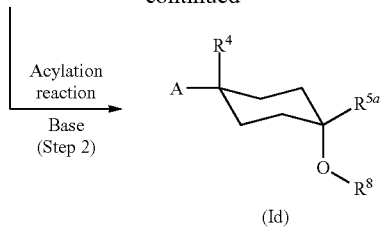

(Id)

wherein $R^{5a}$ and $R^{6a}$ each independently represent a hydrogen atom, $C_1$-$C_3$ haloalkyl, carboxyl or the like; $R^7$ and $R^8$ each independently represent $C_1$-$C_4$ alkyl or the like; and the other symbols have the same meanings as those defined above.

Compound (Ic) can be obtained by alkylation of Compound (Ia), and Compound (Id) can be obtained by alkylation of Compound (Ib). Compound (Ie) can be obtained by acylation of Compound (Ia), and Compound (If) can be obtained by acylation of Compound (Ib).

Step 1 and Step 2

The alkylation reaction of Compound (Ia) or Compound (Ib) is generally carried out by allowing Compound (Ia) or Compound (Ib) to react with a halogenated alkyl in a solvent in the presence of a base, and the solvent is appropriately selected such that it does not inhibit the reaction. Examples of the solvent which does not inhibit the reaction include ethers such as tetrahydrofuran, 1,4-dioxane and ethylene glycol dimethyl ether; acetone; acetonitrile; and N,N-dimethylformamide; and mixtures thereof may also be used as the solvent.

Examples of the base include alkali metal hydrogen carbonates such as sodium hydrogen carbonate and potassium hydrogen carbonate; alkali metal carbonates such as potassium carbonate and cesium carbonate; amines such as triethylamine, diisopropylethylamine and pyridine; potassium tert-butoxide; and sodium hydride.

The amount of the base to be used is preferably 0.5 to 6 moles, more preferably 0.8 to 3 moles with respect to 1 mole of Compound (Ia) or Compound (Ib).

The amount of the halogenated alkyl to be used is preferably 0.5 to 5 moles, more preferably 0.8 to 2 moles with respect to 1 mole of Compound (Ia) or Compound (Ib).

The reaction temperature of the alkylation reaction is preferably −78 to 200° C., more preferably −20 to 100° C.

The reaction time of the alkylation reaction varies depending on the reaction conditions, and is preferably 5 minutes to 78 hours, more preferably 30 minutes to 48 hours.

Step 3 and Step 4

The acylation reaction of Compound (Ia) or Compound (Ib) is generally carried out by allowing Compound (Ia) or Compound (Ib) to react with an acylating agent such as an acid halide or acid anhydride in a solvent in the presence of a base, and the solvent is appropriately selected such that it does not inhibit the reaction. Examples of the solvent which does not inhibit the reaction include halogenated hydrocarbons such as dichloromethane, chloroform, carbon tetrachloride and 1,2-dichloroethane; and ethers such as tetrahydrofuran, 1,2-dimethoxyethane and 1,4-dioxane; and mixtures thereof may also be used as the solvent.

Examples of the base include pyridine, triethylamine, diisopropylethylamine and N,N-dimethylaminopyridine.

The amount of the acid halide or acid anhydride to be used is preferably 0.5 to 3 moles, more preferably 0.8 to 1.5 moles with respect to 1 mole of Compound (Ia) or Compound (Ib).

The amount of the base to be used is preferably 0.1 to 6 moles, more preferably 0.8 to 3 moles with respect to 1 mole of Compound (Ia) or Compound (Ib).

The reaction temperature of the acylation reaction is preferably −20 to 150° C., more preferably 0 to 100° C.

The reaction time of the acylation reaction varies depending on the reaction conditions, and is preferably 5 minutes to 72 hours, more preferably 30 minutes to 48 hours.

Production Method 2: Production Method of Compound (Ih)

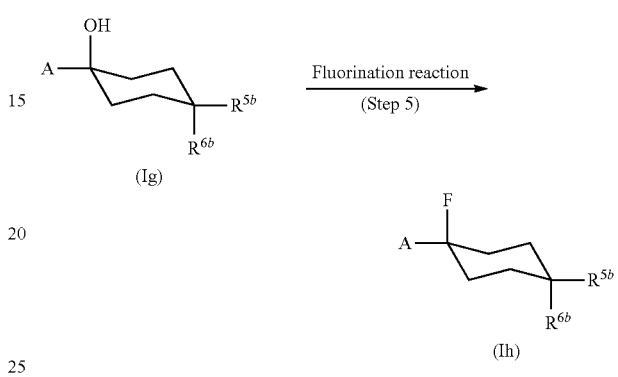

wherein $R^{5b}$ and $R^{6b}$ each independently represent a hydrogen atom, fluorine atom, $C_1$-$C_3$ haloalkyl, $C_1$-$C_4$ alkoxy, $C_2$-$C_5$ alkylcarbonyloxy or the like; and the other symbols have the same meanings as those defined above.

Compound (Ih) can be obtained by fluorination of Compound (Ig).

Step 5

The fluorination of Compound (Ig) is generally carried out by allowing Compound (Ig) to react with a fluorinating agent in a solvent, and the solvent is appropriately selected such that it does not inhibit the reaction. Examples of the solvent which does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile; and mixtures thereof may also be used as the solvent.

Examples of the fluorinating agent include alkylaminosulfur trifluorides such as (dimethylamino)sulfur trifluoride (DAST) and bis(2-methoxyethyl)aminosulfur trifluoride acid.

The amount of the fluorinating agent to be used is preferably 0.25 to 20 moles, more preferably 0.5 to 4 moles with respect to 1 mole of Compound (Ig).

The reaction temperature of the fluorination reaction is preferably −20 to 150° C., more preferably 0 to 100° C.

The reaction time of the fluorination reaction varies depending on the reaction conditions, and is preferably 5 minutes to 72 hours, more preferably 30 minutes to 48 hours.

Production Method 3: Production Method of Compound (Ij)

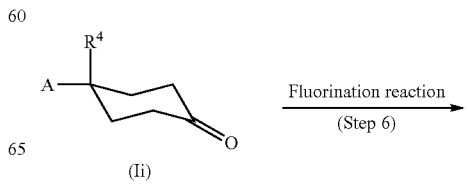

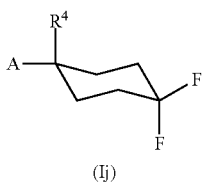

wherein the symbols have the same meanings as those defined above.

Compound (Ij) can be obtained by fluorination of Compound (Ii).

Step 6

The fluorination reaction of Compound (Ii) is generally carried out by allowing Compound (Ii) to react with a fluorinating agent in a solvent, and the solvent is appropriately selected such that it does not inhibit the reaction. Examples of the solvent which does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile; and mixtures thereof may also be used as the solvent.

Examples of the fluorinating agent include alkylaminosulfur trifluorides such as (dimethylamino)sulfur trifluoride (DAST) and bis(2-methoxyethyl)aminosulfur trifluoride acid.

The amount of the fluorinating agent to be used is preferably 0.25 to 20 moles, more preferably 0.5 to 4 moles with respect to 1 mole of Compound (Ii).

The reaction temperature of the fluorination reaction is preferably −20 to 150° C., more preferably 0 to 100° C.

The reaction time of the fluorination reaction varies depending on the reaction conditions, and is preferably 5 minutes to 72 hours, more preferably 30 minutes to 48 hours.

Production Method 4: Production Method of Compound (Ik) and Compound (Il)

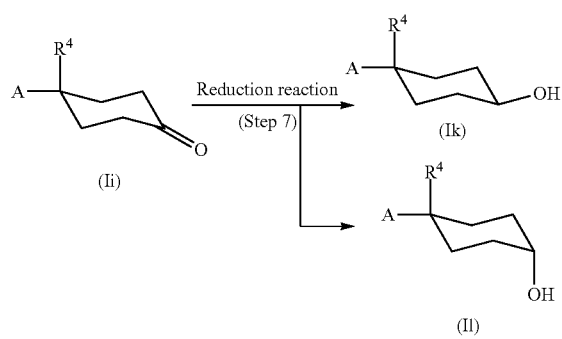

wherein the symbols have the same meanings as those defined above.

Compound (Ik) and Compound (Il) can be obtained by reduction of Compound (Ii).

Step 7

The reduction reaction of Compound (Ii) is generally carried out by allowing Compound (Ii) to react with a reducing agent in a solvent, and the solvent is appropriately selected such that it does not inhibit the reaction. Examples of the solvent which does not inhibit the reaction include hydrocarbons such as octane, hexane, benzene and toluene; ethers such as tetrahydrofuran, 1,4-dioxane, ethylene glycol dimethyl ether and diethyl ether; and alcohols such as methanol, ethanol and isopropyl alcohol; and mixtures thereof may also be used as the solvent.

Examples of the reducing agent include sodium borohydride, lithium borohydride, diisobutylaluminum hydride, lithium aluminum hydride, lithium triethyl hydride, sodium bis(2-methoxyethoxy)aluminum hydride and borane complexes.

The amount of the reducing agent to be used is preferably 0.25 to 100 moles, more preferably 0.5 to 20 moles with respect to 1 mole of Compound (Ii).

The reaction temperature of the reduction reaction is preferably −78 to 150° C., more preferably −78 to 100° C.

The reaction time of the reduction reaction varies depending on the reaction conditions such as the reaction temperature and the amount of the reducing agent, and is preferably 5 minutes to 72 hours, more preferably 30 minutes to 24 hours.

Production Method 5: Production Method of Compound (Im) and Compound (In)

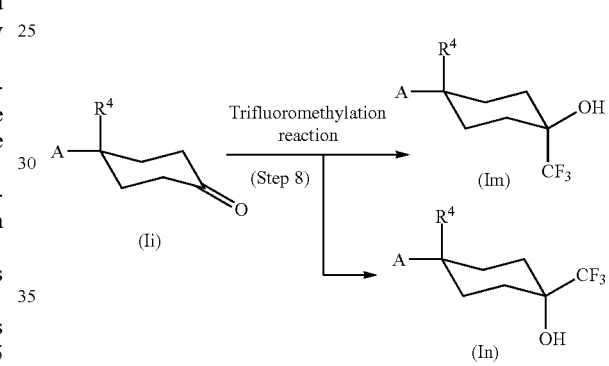

wherein the symbols have the same meanings as those defined above.

Compound (Im) and Compound (In) are obtained by trifluoromethylation of Compound (Ii).

Step 8

Examples of the trifluoromethylating reagent include organosilicon compounds such as (trifluoromethyl)trimethylsilane. The trifluoromethylation reaction using an organosilicon compound can be carried out by the method described in Journal of the American Chemical Society, 1989, Vol. 39, p. 393-395 or a method corresponding thereto.

Production Method 6: Production Method of Compound (Io)

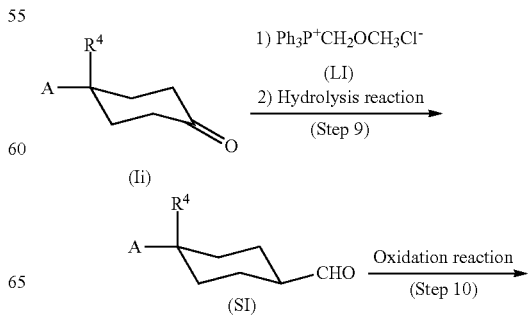

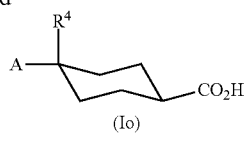

wherein the symbols have the same meanings as those defined above.

Compound (SI) is obtained by allowing a Wittig reagent (LI) to act on Compound (Ii), followed by hydrolyzing the resulting compound. The Wittig reagent (LI) employed may be one commercially available, but the reagent may also be synthesized according to a known method. Compound (Io) is obtained by oxidizing Compound (SI).

Step 9

The Wittig reaction of Compound (Ii) is generally carried out by allowing Compound (Ii) to react with a Wittig reagent in a solvent in the presence of a base, and the solvent is appropriately selected such that it does not inhibit the reaction. Examples of the solvent which does not inhibit the reaction include hydrocarbons such as octane, hexane, benzene and toluene; and ethers such as tetrahydrofuran, 1,4-dioxane, ethylene glycol dimethyl ether and diethyl ether; and mixtures thereof may also be used as the solvent.

Examples of the base include lithium diisopropylamide, potassium tert-butoxide, sodium hydride, phenyllithium and tert-butyllithium.

The amount of the base to be used is preferably 0.5 to 3 moles, more preferably 0.8 to 2 moles with respect to 1 mole of Compound (Ii).

The amount of Compound (LI) to be used is preferably 0.5 to 3 moles, more preferably 0.8 to 2 moles with respect to 1 mole of Compound (Ii).

The reaction temperature of the Wittig reaction is preferably −78 to 100° C., more preferably −78 to 50° C.

The reaction time of the Wittig reaction varies depending on the reaction conditions, and is preferably 5 minutes to 48 hours, more preferably 30 minutes to 24 hours.

The hydrolysis reaction to obtain Compound (SI) is carried out in a solvent appropriately selected, which solvent does not inhibit the reaction. Examples of the solvent which does not inhibit the reaction include ethers such as tetrahydrofuran, 1,4-dioxane and ethylene glycol dimethyl ether; alcohols such as methanol, ethanol and tert-butanol; acetonitrile; and water; and mixtures thereof may also be used as the solvent.

The concentration of the acid used in the hydrolysis reaction is preferably 0.1 to 12 M, and the amount of the acid to be used is preferably 1 mole to an excess amount with respect to 1 mole of Compound (Ii).

Examples of the acid to be used in the hydrolysis reaction include inorganic acids such as hydrochloric acid and sulfuric acid; and organic acids such as acetic acid.

The reaction temperature of the hydrolysis reaction is preferably −20 to 200° C., more preferably 0 to 100° C.

The reaction time of the hydrolysis reaction varies depending on the reaction conditions, and is preferably 5 minutes to 48 hours, more preferably 30 minutes to 24 hours.

Step 10

Examples of the oxidizing agent to be used in the oxidation reaction of Compound (SI) include chromium oxide (VI)-acetic acid, Jones reagent and sodium chlorite. The oxidation reaction may be carried out according to a known method.

Production Method 7: Production Method of Compound (Ii)

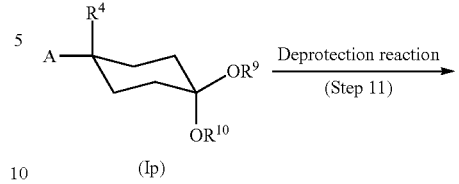

wherein $R^9$ and $R^{10}$ each independently represent methyl, ethyl, n-propyl, isopropyl, n-butyl, sec-butyl, tert-butyl or the like, or $R^9$ and $R^{10}$ may together form an ethylene group (—CH$_2$CH$_2$—) or a propylene group (—CH$_2$CH$_2$CH$_2$—); and the other symbols have the same meanings as those defined above.

Compound (Ii) is obtained by deprotection of Compound (Ip).

Step 11

The deprotection reaction of Compound (Ip) may be carried out according to a method described in PROTECTIVE GROUPS IN ORGANIC SYNTHESIS (WILEY-INTERSCIENCE) or a method corresponding thereto.

Production Method 8: Production Method of Compound (IIIb)

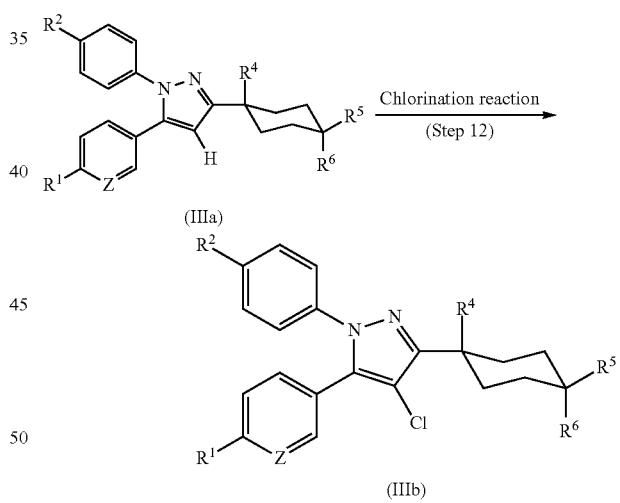

wherein the symbols have the same meanings as those defined above.

Compound (IIIb) can be obtained by chlorination of Compound (IIIa).

Step 12

The chlorination reaction of Compound (IIIa) is generally carried out by allowing Compound (IIIa) to react with a chlorinating agent in a solvent, and the solvent is appropriately selected such that it does not inhibit the reaction. Examples of the solvent which does not inhibit the reaction include halogenated hydrocarbons such as dichloromethane, chloroform, carbon tetrachloride and 1,2-dichloroethane; acetonitrile; and ethyl acetate; and mixtures thereof may also be used as the solvent.

Examples of the chlorinating agent include N-chlorosuccinimide (NCS).

The amount of the chlorinating agent to be used is preferably 0.5 to 2 moles, more preferably 0.8 to 1.2 moles with respect to 1 mole of Compound (IIIa).

The reaction temperature of the chlorination reaction is preferably 0 to 200° C., more preferably 0 to 120° C.

The reaction time of the chlorination reaction varies depending on the reaction conditions such as the reaction temperature, and is preferably 5 minutes to 72 hours, more preferably 30 minutes to 48 hours.

Production Method 9: Production Method of Compound (IIIa)

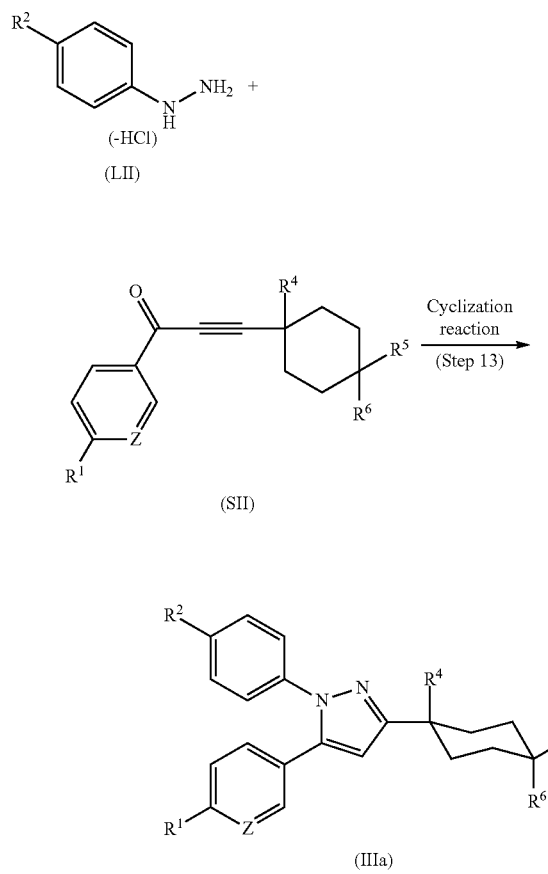

wherein the symbols have the same meanings as those defined above.

Compound (IIIa) can be obtained by cyclization of Compound (LII) and Compound (SII). The Compound (LII) may be one commercially available, but it may also be synthesized according to a known method.

Step 13

The cyclization reaction of Compound (LII) and Compound (SII) is generally carried out in a solvent appropriately selected such that it does not inhibit the reaction. Examples of the solvent which does not inhibit the reaction include alcohols such as methanol, ethanol and isopropyl alcohol; halogenated hydrocarbons such as dichloromethane, chloroform, carbon tetrachloride and 1,2-dichloroethane; ethers such as tetrahydrofuran, 1,2-dimethoxyethane and 1,4-dioxane; benzene; toluene; acetic acid; and water; and mixtures thereof may also be used as the solvent.

The amount of Compound (LII) to be used is preferably 0.5 to 1.5 moles, more preferably 0.8 to 1.2 moles with respect to 1 mole of Compound (SII).

In the cyclization reaction, a catalyst may be used, and examples of the catalyst include organic bases such as triethylamine and pyridine; inorganic acids such as hydrochloric acid and sulfuric acid; and organic acids such as acetic acid.

The amount of the catalyst to be used is preferably 0.1 to 3 moles with respect to 1 mole of Compound (SII).

The reaction temperature of the cyclization reaction is preferably 0 to 200° C., more preferably 0 to 120° C.

The reaction time of the cyclization reaction varies depending on the reaction conditions such as the reaction temperature, and is preferably 5 minutes to 72 hours, more preferably 30 minutes to 48 hours.

Production Method 10: Production Method of Compound (IV)

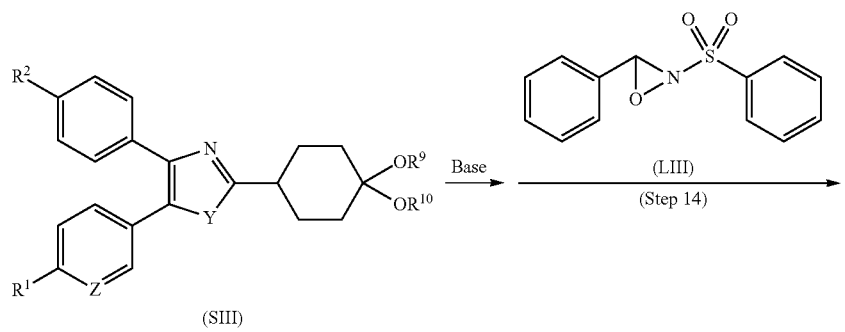

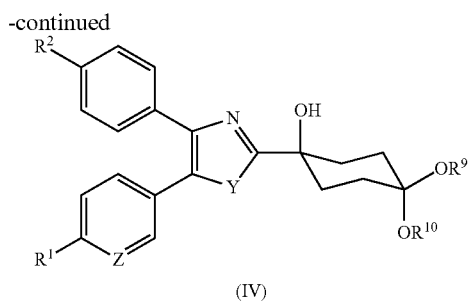

(IV)

wherein the symbols have the same meanings as those defined above.

Compound (IV) can be obtained by deprotonation and oxidation of Compound (SIII). The oxidation reaction may be carried out according to a method described in Tetrahedron, 1989, vol. 45, p. 5703-5742 or a method corresponding thereto.

Step 14

The deprotonation reaction and the oxidation reaction are generally carried out by allowing Compound (SIII) to react with a base and an oxidizing agent in an anhydrous solvent, and the solvent is appropriately selected such that it does not inhibit the reaction. Examples of the solvent which does not inhibit the reaction include hydrocarbons such as octane, hexane and heptane; and ethers such as tetrahydrofuran, 1,4-dioxane, ethylene glycol dimethyl ether and diethyl ether; and mixtures thereof may also be used as the solvent.

Examples of the base include butyllithiums such as n-butyllithium, sec-butyllithium and tert-butyllithium.

The amount of the base to be used is preferably 0.8 to 5 moles, more preferably 0.9 to 3 moles with respect to 1 mole of Compound (SIII).

The amount of Compound (LIII) to be used is preferably 0.8 to 5 moles, more preferably 0.9 to 3 moles with respect to 1 mole of Compound (SIII).

Examples of the oxidizing agent used in the hydrolysis reaction include 3-phenyl-2-(phenylsulfonyl)-1,2-oxaziridine.

The reaction temperature of the deprotonation reaction and the oxidation reaction is preferably −78 to 150° C., more preferably 0 to 50° C.

The reaction time of the deprotonation reaction and the oxidation reaction varies depending on the reaction conditions, and is preferably 5 minutes to 72 hours, more preferably 30 minutes to 48 hours.

Production Method 11: Production Method of Intermediate Compound (VI)

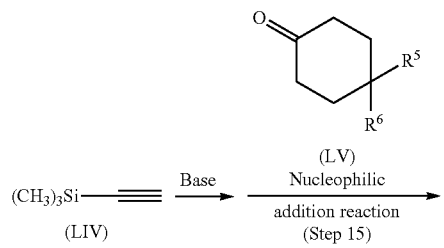

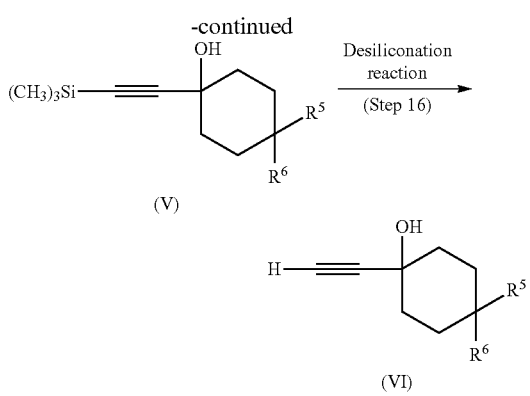

wherein the symbols have the same meanings as those defined above.

Compound (VI) can be obtained by allowing Compound (LIV) to react with Compound (LV) followed by solvolysis of the resulting Compound (V). The Compound (LIV) and Compound (LV) may be those commercially available, but these may also be synthesized according to known methods.

Step 15

The reaction of Compound (LIV) with Compound (LV) is generally carried out in an anhydrous solvent in the presence of a base, and the solvent is appropriately selected such that it does not inhibit the reaction. Examples of the solvent which does not inhibit the reaction include hydrocarbons such as octane, hexane, benzene and toluene; and ethers such as tetrahydrofuran, 1,4-dioxane, ethylene glycol dimethyl ether and diethyl ether; and mixtures thereof may also be used as the solvent.

Examples of the base include alkyllithiums such as methyllithium and n-butyllithium; and salts of dialkylamines such as lithium diisopropylamide, lithium bis(trimethylsilyl)amide and potassium bis(trimethylsilyl)amide.

The amount of the base to be used is preferably 0.8 to 5 moles, more preferably 0.9 to 3 moles with respect to 1 mole of Compound (LIV).

The amount of Compound (LV) to be used is preferably 0.8 to 5 moles, more preferably 0.9 to 3 moles with respect to 1 mole of Compound (LIV).

The reaction temperature of the reaction between the Compound (LIV) and Compound (LV) is preferably −78 to 150° C., more preferably −78 to 100° C.

The reaction time of the reaction between the Compound (LIV) and Compound (LV) varies depending on the reaction conditions, and is preferably 5 minutes to 72 hours, more preferably 30 minutes to 48 hours.

Step 16

The solvolysis reaction is generally carried out in a solvent in the presence of a base, and the solvent is appropriately selected such that it does not inhibit the reaction. Examples of the solvent which does not inhibit the reaction include alcohols such as methanol and ethanol; and water; and mixtures thereof may also be used as the solvent.

Examples of the base include potassium carbonate, sodium carbonate, potassium hydroxide and sodium hydroxide.

The amount of the base to be used is preferably 0.5 to 10 moles, more preferably 0.8 to 3 moles with respect to 1 mole of Compound (V).

The reaction temperature of the solvolysis reaction is preferably −20 to 150° C., more preferably 0 to 100° C.

The reaction time of the solvolysis reaction varies depending on the reaction conditions, and is preferably 5 minutes to 72 hours, more preferably 30 minutes to 48 hours.

Production Method 12: Production Method of Intermediate Compound (SIIa)

as lithium diisopropylamide, lithium bis(trimethylsilyl) amide and potassium bis(trimethylsilyl)amide.

The amount of the base to be used is preferably 0.8 to 5 moles, more preferably 0.9 to 3 moles with respect to 1 mole of Compound (VI).

The amount of Compound (LVI) or Compound (LVII) to be used is preferably 0.8 to 5 moles, more preferably 0.9 to 3 moles with respect to 1 mole of Compound (VI).

The reaction temperature of the reaction of Compound (VI) with Compound (LVI) or with Compound (LVII) is preferably −78 to 150° C., more preferably 0 to 50° C.

The reaction time of the reaction of Compound (VI) with Compound (LVI) or with Compound (LVII) varies depending on the reaction conditions, and is preferably 5 minutes to 72 hours, more preferably 30 minutes to 48 hours.

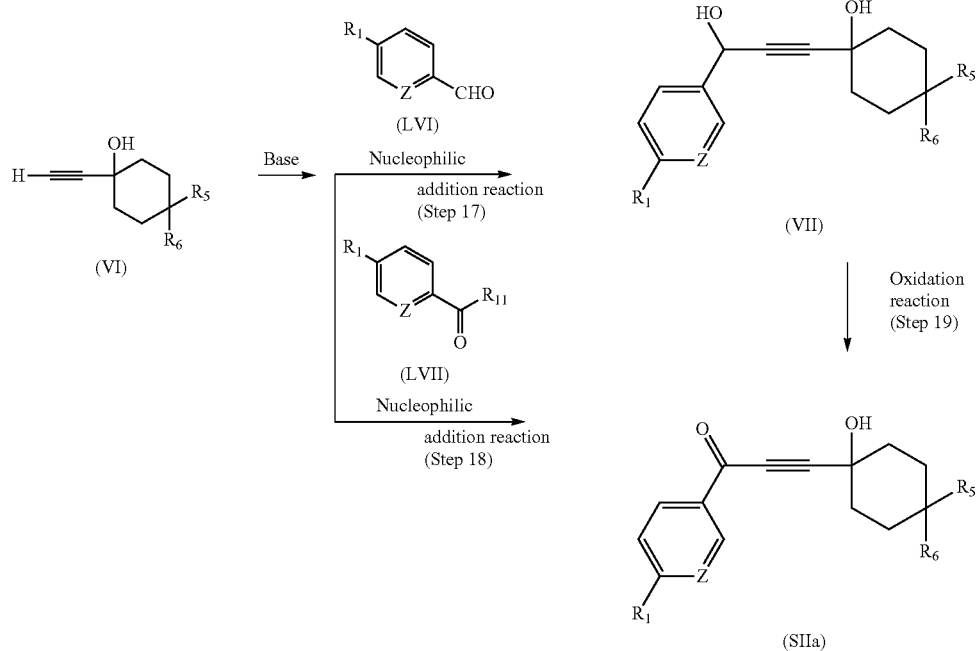

wherein $R^{11}$ represents a chlorine atom; imidazolyl group; N-methoxy-N-methylamino group; or an alkoxy group such as a methoxy group or ethoxy group; and the other symbols have the same meanings as those defined above.

Compound (SIIa) can be obtained by allowing Compound (VI) to react with Compound (LVI), followed by oxidizing the resulting Compound (VII). Compound (SIIa) can be obtained also by allowing Compound (VI) to react with Compound (LVII). The Compound (LVI) and Compound (LVII) may be those commercially available, but these may also be synthesized according to known methods.

Step 17 or Step 18

The reaction of Compound (VI) with Compound (LVI) or with Compound (LVII) is generally carried out in an anhydrous solvent in the presence of a base, and the solvent is appropriately selected such that it does not inhibit the reaction. Examples of the solvent which does not inhibit the reaction include hydrocarbons such as octane, hexane, benzene and toluene; and ethers such as tetrahydrofuran, 1,4-dioxane, ethylene glycol dimethyl ether and diethyl ether; and mixtures thereof may also be used as the solvent.

Examples of the base include alkyllithiums such as methyllithium and n-butyllithium; and salts of dialkylamines such Step 19

The oxidation reaction of Compound (VII) is generally carried out by allowing Compound (VII) to react with an oxidizing agent in a solvent, and the solvent is appropriately selected such that it does not inhibit the reaction. Examples of the solvent which does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; alkyl nitriles such as acetonitrile; trifluoroacetic acid; pyridine; and acetone; and mixtures thereof may also be used as the solvent.

Examples of the oxidizing agent include commercially available reagents such as manganese dioxide; sulfur trioxide-pyridine; activated dimethyl sulfoxide; and Dess-Martin reagent.

The amount of the oxidizing agent to be used is preferably 0.5 to 3 moles, more preferably 0.8 to 2 moles with respect to 1 mole of Compound (VII).

The reaction temperature of the oxidation reaction varies depending on the type of the oxidizing agent, and is preferably −78 to 100° C., more preferably −78 to 40° C.

The reaction time of the oxidation reaction varies depending on the reaction conditions such as the type of the oxidizing agent and the reaction temperature, and is preferably 5 minutes to 72 hours, more preferably 1 to 24 hours.

Production Method 13: Production Method of Intermediate Compound (IX)

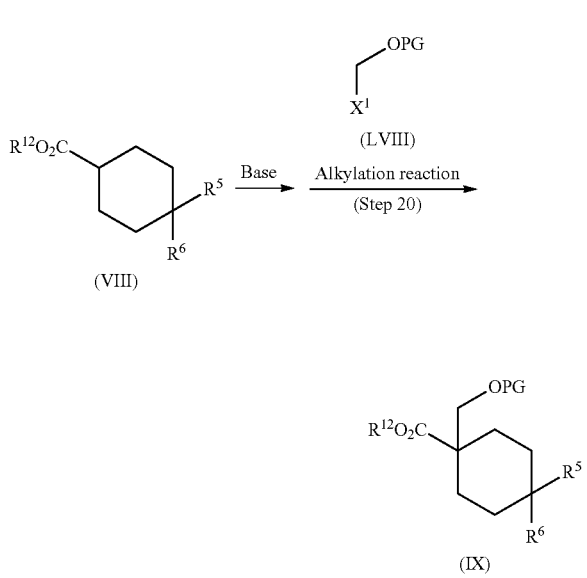

wherein $X^1$ represents a halogen atom; PG represents a protective group such as methyl or benzyl; $R^{12}$ represents an alkoxy group such as methoxy or ethoxy; and the other symbols have the same meanings as those defined above.

Compound (IX) can be obtained by allowing Compound (VIII) to react with Compound (LVIII). The Compound (VIII) and Compound (LVIII) may be those commercially available, but these may also be synthesized according to known methods.

Step 20

The reaction of Compound (VIII) with Compound (LVIII) is generally carried out in an anhydrous solvent in the presence of a base, and the solvent is appropriately selected such that it does not inhibit the reaction. Examples of the solvent which does not inhibit the reaction include hydrocarbons such as octane, hexane, benzene and toluene; and ethers such as tetrahydrofuran, 1,4-dioxane, ethylene glycol dimethyl ether and diethyl ether; and mixtures thereof may also be used as the solvent.

Examples of the base include lithium diisopropylamide, lithium bis(trimethylsilyl)amide and potassium bis(trimethylsilyl)amide.

The amount of the base to be used is preferably 0.8 to 4 moles, more preferably 0.9 to 3.5 moles with respect to 1 mole of Compound (VIII).

The amount of Compound (LVIII) to be used is preferably 0.8 to 5 moles, more preferably 0.9 to 3 moles with respect to 1 mole of Compound (VIII).

The reaction temperature of the reaction of Compound (VIII) with Compound (LVIII) is preferably −78 to 150° C., more preferably 0 to 50° C.

The reaction time of the reaction of Compound (VIII) with Compound (LVIII) varies depending on the reaction conditions, and is preferably 5 minutes to 72 hours, more preferably 30 minutes to 48 hours.

Production Method 14: Production Method of Intermediate Compound (XI)

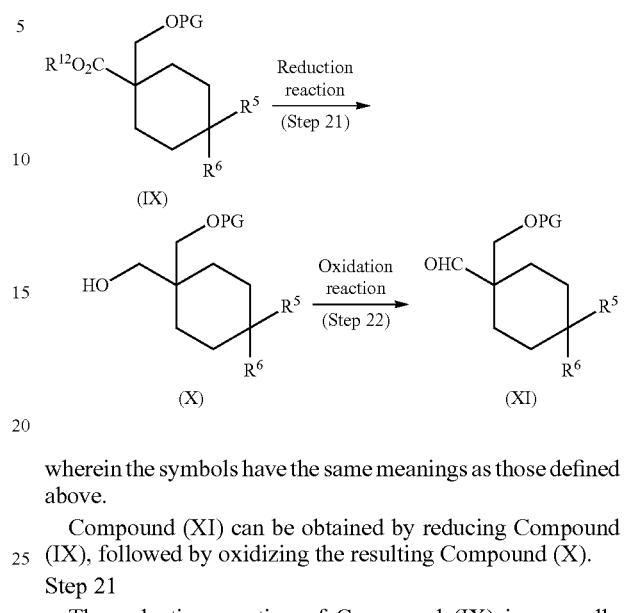

wherein the symbols have the same meanings as those defined above.

Compound (XI) can be obtained by reducing Compound (IX), followed by oxidizing the resulting Compound (X).

Step 21

The reduction reaction of Compound (IX) is generally carried out by allowing Compound (IX) to react with a reducing agent in a solvent, and the solvent is appropriately selected such that it does not inhibit the reaction. Examples of the solvent which does not inhibit the reaction include hydrocarbons such as octane, hexane, benzene and toluene; ethers such as tetrahydrofuran, 1,4-dioxane, ethylene glycol dimethyl ether and diethyl ether; and alcohols such as methanol, ethanol and isopropyl alcohol; and mixtures thereof may also be used as the solvent.

Examples of the reducing agent include lithium borohydride, diisobutylaluminum hydride, lithium aluminum hydride, lithium triethyl hydride, sodium bis(2-methoxyethoxy)aluminum hydride and borane complexes.

The amount of the reducing agent to be used is preferably 0.25 to 100 moles, more preferably 0.5 to 20 moles with respect to 1 mole of Compound (IX).

The reaction temperature of the reduction reaction is preferably −78 to 150° C., more preferably −78 to 100° C.

The reaction time of the reduction reaction varies depending on the reaction conditions such as the reaction temperature and the amount of the reducing agent, and is preferably 5 minutes to 72 hours, more preferably 30 minutes to 24 hours.

Step 22

The oxidation reaction of Compound (X) is generally carried by allowing Compound (X) to react with an oxidizing agent in a solvent, and the solvent is appropriately selected such that it does not inhibit the reaction. Examples of the solvent which does not inhibit the reaction include trifluoroacetic acid, pyridine, acetone, hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile; and mixtures thereof may also be used as the solvent.

Examples of the oxidizing agent include commercially available reagents such as sulfur trioxide-pyridine; activated dimethyl sulfoxide; and Dess-Martin reagent.

The amount of the oxidizing agent to be used is preferably 0.5 to 3 moles, more preferably 0.8 to 2 moles with respect to 1 mole of Compound (X).

The reaction temperature of the oxidation reaction varies depending on the type of the oxidizing agent, and is preferably −78 to 100° C., more preferably −78 to 40° C.

The reaction time of the oxidation reaction varies depending on the reaction conditions such as the type of the oxidizing agent and the reaction temperature, and is preferably 5 minutes to 72 hours, more preferably 1 to 24 hours.

Production Method 15: Production Method of Intermediate Compound (XII)

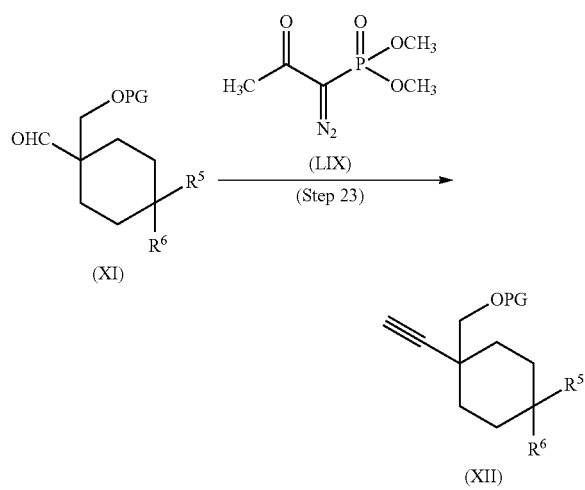

wherein the symbols have the same meanings as those defined above.

Step 23

Compound (XII) can be obtained by converting Compound (XI) to an alkyne. Examples of the reagent to be used in the conversion reaction include dimethyl-1-diazo-2-oxopropylphosphonate. The conversion reaction can be carried out according to the method described in Tetrahedron Letters, 2006, vol. 47, pp. 1729-1731 or a method corresponding thereto.

Production Method 16: Production Method of Intermediate Compound (SIIb)

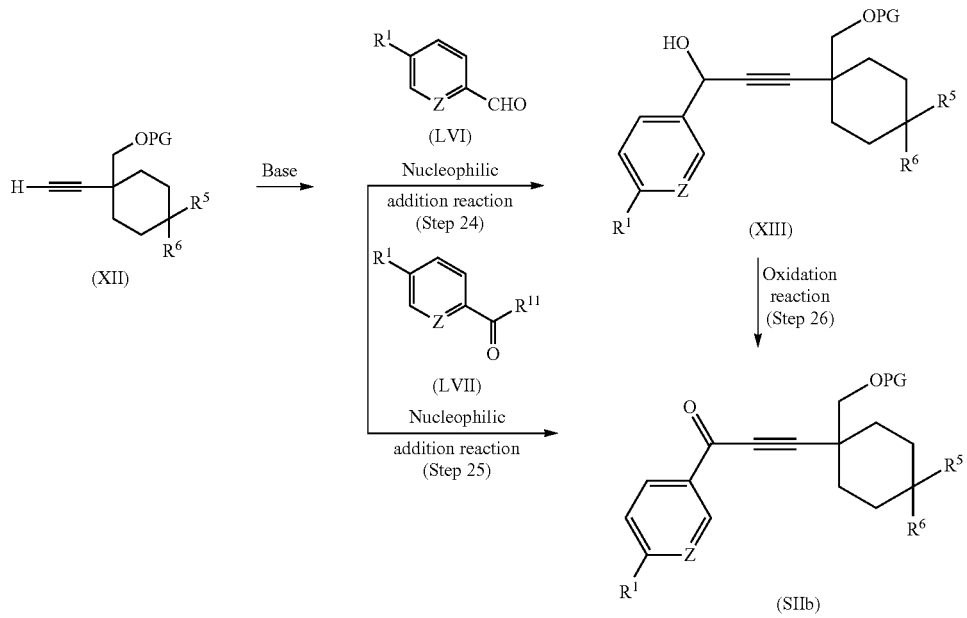

wherein the symbols have the same meanings as those defined above.

Compound (SIIb) can be obtained by allowing Compound (XII) to react with Compound (LVI), followed by oxidizing the resulting Compound (XIII). Compound (SIIb) can be obtained also by allowing Compound (XII) to react with Compound (LVII). The Compound (LVI) and Compound (LVII) may be those commercially available, but these may also be synthesized according to known methods.

Step 24 or Step 25

The nucleophilic addition reaction of Compound (XII) is generally carried out in an anhydrous solvent in the presence of a base, and the solvent is appropriately selected such that it does not inhibit the reaction. Examples of the solvent which does not inhibit the reaction include hydrocarbons such as octane, hexane, benzene and toluene; and ethers such as tetrahydrofuran, 1,4-dioxane, ethylene glycol dimethyl ether and diethyl ether; and mixtures thereof may also be used as the solvent.

Examples of the base include alkyllithiums such as methyllithium and n-butyllithium; and salts of dialkylamines such as lithium diisopropylamide, lithium bis(trimethylsilyl) amide and potassium bis(trimethylsilyl)amide.

The amount of the base to be used is preferably 0.8 to 5 moles, more preferably 0.9 to 3 moles with respect to 1 mole of Compound (XII).

The amount of Compound (LVI) or Compound (LVII) to be used is preferably 0.8 to 5 moles, more preferably 0.9 to 3 moles with respect to 1 mole of Compound (XII).

The reaction temperature of the nucleophilic addition reaction is preferably −78 to 150° C., more preferably 0 to 50° C.

The reaction time of the nucleophilic addition reaction varies depending on the reaction conditions, and is preferably 5 minutes to 72 hours, more preferably 30 minutes to 48 hours.

Step 26

The oxidation reaction of Compound (XIII) is generally carried out by allowing Compound (XIII) to react with an oxidizing agent in a solvent, and the solvent is appropriately selected such that it does not inhibit the reaction. Examples of the solvent which does not inhibit the reaction include trifluoroacetic acid, pyridine, acetone, hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile; and mixtures thereof may also be used as the solvent.

Examples of the oxidizing agent include commercially available reagents such as manganese dioxide; sulfur trioxide-pyridine; activated dimethyl sulfoxide; and Dess-Martin reagent.

The amount of the oxidizing agent to be used is preferably 0.5 to 3 moles, more preferably 0.8 to 2 moles with respect to 1 mole of Compound (XIII).

The reaction temperature of the oxidation reaction varies depending on the type of the oxidizing agent, and is preferably −78 to 100° C., more preferably −78 to 40° C.

The reaction time of the oxidation reaction varies depending on the reaction conditions such as the type of the oxidizing agent and the reaction temperature, and is preferably 5 minutes to 72 hours, more preferably 1 to 24 hours.

Production Method 17: Production Method of Intermediate Compound (SIIIa)

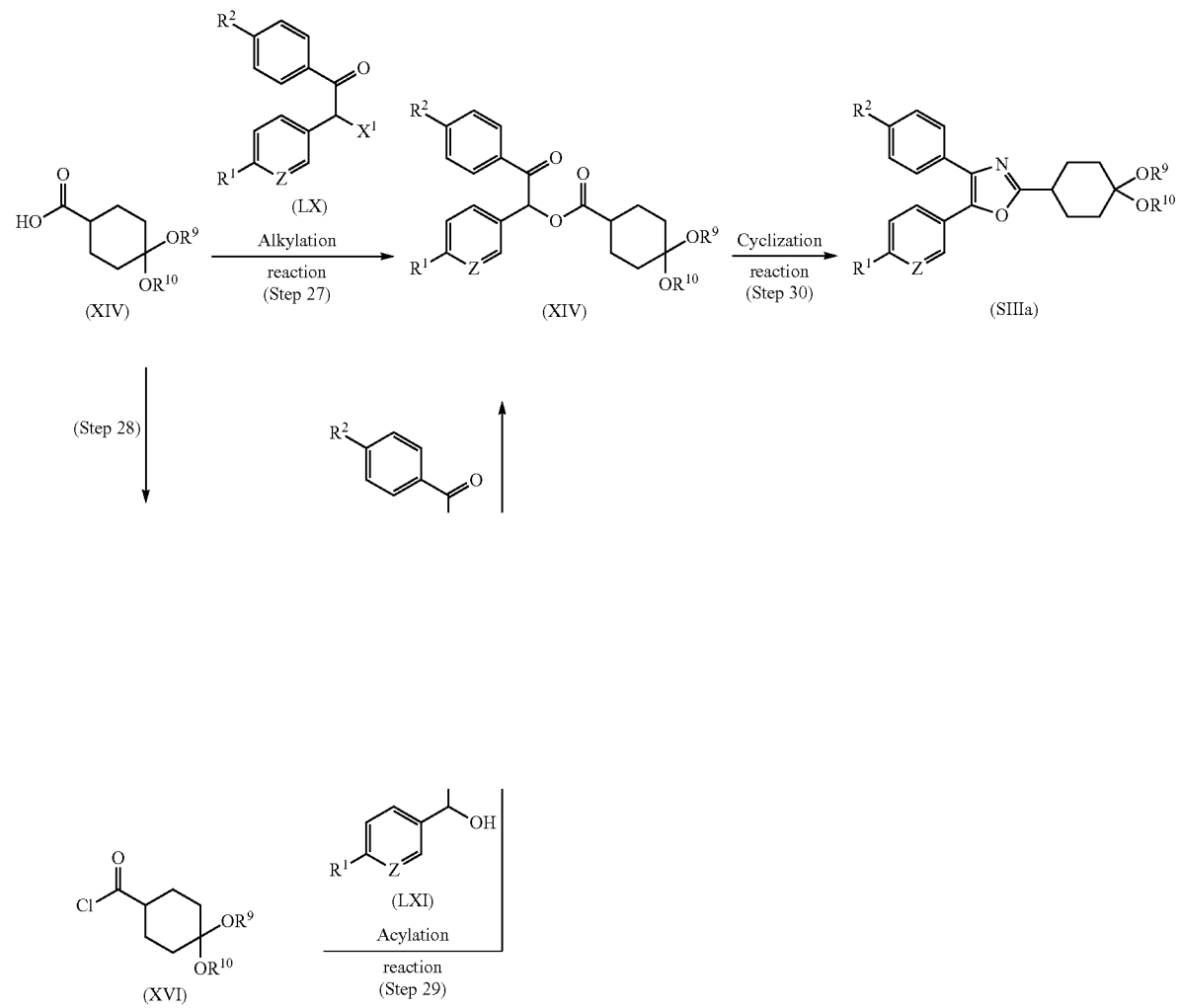

wherein the symbols have the same meanings as those defined above.

Compound (SIIIa) can be obtained by alkylating Compound (XIV) with Compound (LX) or acylating Compound (XVI) obtained from Compound (XIV) with Compound (LXI), thereby obtaining Compound (XV), which is then cyclized. Compound (XIV) and Compound (LX) can be synthesized according to known methods. The Compound (LXI) may be one commercially available, but it may also be synthesized according to a known method.

Step 27

The alkylation reaction of Compound (XIV) is generally carried out by allowing Compound (XIV) to react with a halogenated alkyl in a solvent in the presence of a base, and the solvent is appropriately selected such that it does not inhibit the reaction. Examples of the solvent which does not inhibit the reaction include ethers such as tetrahydrofuran, 1,4-dioxane and ethylene glycol dimethyl ether; acetone; acetonitrile; and N,N-dimethylformamide; and mixtures thereof may also be used as the solvent.

Examples of the base include alkali metal hydrogen carbonates such as sodium hydrogen carbonate and potassium hydrogen carbonate; alkali metal carbonates such as potassium carbonate and cesium carbonate; amines such as triethylamine, diisopropylethylamine and pyridine; potassium tert-butoxide; and sodium hydride.

The amount of the base to be used is preferably 0.5 to 6 moles, more preferably 0.8 to 3 moles with respect to 1 mole of Compound (XIV).

The amount of the Compound (LX) to be used is preferably 0.5 to 5 moles, more preferably 0.8 to 2 moles with respect to 1 mole of Compound (XIV).

The reaction temperature of the alkylation reaction is preferably −78 to 200° C., more preferably −20 to 100° C.

The reaction time of the alkylation reaction varies depending on the reaction conditions, and is preferably 5 minutes to 78 hours, more preferably 30 minutes to 48 hours.

Step 28

Compound (XVI) can be synthesized from Compound (XIV) according to, for example, a method using thionyl chloride, oxalyl chloride or the like, which known method.

Step 29

The acylation reaction of Compound (LXI) with Compound (XVI) is generally carried out in a solvent in the presence of a base, and the solvent is appropriately selected such that it does not inhibit the reaction. Examples of the solvent which does not inhibit the reaction include halogenated hydrocarbons such as dichloromethane, chloroform, carbon tetrachloride and 1,2-dichloroethane; and ethers such as tetrahydrofuran, 1,2-dimethoxyethane and 1,4-dioxane; and mixtures thereof may also be used as the solvent.

Examples of the base include pyridine, triethylamine, diisopropylethylamine and N,N-dimethylaminopyridine.

The amount of the base to be used is preferably 0.1 to 6 moles, more preferably 0.8 to 3 moles with respect to 1 mole of Compound (XVI).

The amount of Compound (LXI) to be used is 0.5 to 3 moles, more preferably 0.8 to 1.5 moles with respect to 1 mole of Compound (XVI).

The reaction temperature of the acylation reaction is preferably −20 to 150° C., more preferably 0 to 100° C.

The reaction time of the acylation reaction varies depending on the reaction conditions, and is preferably 5 minutes to 72 hours, more preferably 30 minutes to 48 hours.

Step 30

The cyclization reaction of Compound (XV) is generally carried out in a solvent in the presence of an ammonium salt, and the solvent is selected such that it does not inhibit the reaction. Examples of the solvent which does not inhibit the reaction include acetic acid and formic acid; and mixtures thereof may also be used as the solvent.

Examples of the ammonium salt include ammonium acetate, ammonium formate and ammonium carbonate, which are commercially available reagents.

The amount of the ammonium salt to be used is preferably 1 to 20 moles, more preferably 2 to 15 moles with respect to 1 mole of Compound (XV).

The reaction temperature of the cyclization reaction is preferably 0 to 200° C., more preferably 0 to 120° C.

The reaction time of the cyclization reaction varies depending on the reaction conditions, and is preferably 5 minutes to 100 hours, more preferably 30 minutes to 48 hours.

Production Method 18: Production Method of Intermediate Compound (SIIIb)

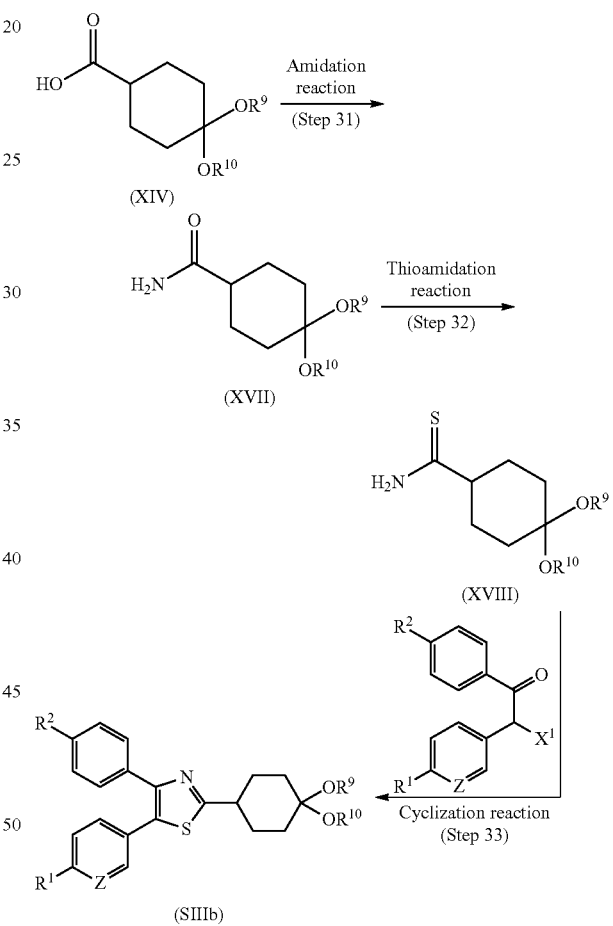

wherein the symbols have the same meanings as those defined above.

Compound (SIIIb) can be obtained by amidating Compound (XIV) and then thioamidating the resulting Compound (XVII) to produce Compound (XVIII), which is then cyclized using Compound (LX). Compound (XIV) can be synthesized according to a known method. Compound (LX) can also be synthesized according to a known method.

Step 31

The amidation reaction of Compound (XIV) is generally carried out by forming a mixed anhydride in a solvent in the presence of a base using a chloroformic ester or the like, followed by allowing aqueous ammonia to react with the mixed anhydride. The solvent is appropriately selected such that it does not inhibit the reaction. Examples of the solvent which does not inhibit the reaction include ethers such as tetrahydrofuran, 1,4-dioxane and ethylene glycol dimethyl ether; halogenated hydrocarbons such as dichloromethane and chloroform; and N,N-dimethylformamide; and mixtures thereof may also be used as the solvent.

Examples of the chloroformic ester include methyl chloroformate, ethyl chloroformate, isopropyl chloroformate and sec-butyl chloroformate.

The amount of the chloroformic ester is preferably 0.5 to 4 moles, more preferably 0.9 to 2 moles with respect to 1 mole of Compound (XIV).

Examples of the base include inorganic bases such as sodium hydrogen carbonate, sodium carbonate, potassium carbonate and cesium carbonate; and organic bases such as triethylamine, diisopropylethylamine and pyridine.

The amount of the base to be used is preferably 0.5 to 5 moles, more preferably 0.9 to 2.5 moles with respect to 1 mole of Compound (XIV).

The reaction temperature of the amidation reaction is preferably −78 to 200° C., more preferably −20 to 100° C. in terms of the formation of a mixed anhydride. In terms of the reaction after addition aqueous ammonia, the temperature is preferably −78 to 200° C., more preferably −20 to 100° C.

The reaction time of the amidation reaction varies depending on the reaction conditions, and is preferably 5 minutes to 48 hours, more preferably 30 minutes to 24 hours in terms of the formation of a mixed anhydride. In terms of the reaction after addition aqueous ammonia, the reaction time is preferably 5 minutes to 72 hours, more preferably 30 minutes to 48 hours Step 32

The thioamidation reaction of Compound (XVII) is generally carried out by allowing Compound (XVII) to react with Lawesson's reagent or phosphorus pentasulfide, which are commercially available reagents, in a solvent. The solvent is appropriately selected such that it does not inhibit the reaction. Examples of the solvent which does not inhibit the reaction include saturated hydrocarbons such as benzene and toluene; halogenated solvents such as dichloromethane and chloroform; and ethers such as tetrahydrofuran and 1,4-dioxane; and mixtures thereof may also be used as the solvent.

The amount of the Lawesson's reagent or phosphorus pentasulfide to be used is preferably 0.3 to 4 moles, more preferably 0.4 to 2 moles with respect to 1 mole of Compound (XVII).

The reaction temperature of the thioamidation reaction is preferably −20 to 200° C., more preferably 0 to 120° C.

The reaction time of the thioamidation reaction varies depending on the reaction conditions, and is preferably 5 minutes to 72 hours, more preferably 30 minutes to 48 hours.

Step 33

The cyclization reaction of Compound (XVIII) is generally carried out in a solvent appropriately selected such that it does not inhibit the reaction. Examples of the solvent which does not inhibit the reaction include alcohols such as methanol and ethanol; ethers such as tetrahydrofuran and 1,4-dioxane; and acetonitrile; and mixtures thereof may also be used as the solvent.

The amount of Compound (LX) to be used is preferably 0.5 to 4 moles, more preferably 0.9 to 1.5 moles with respect to 1 mole of Compound (XVIII).

The reaction temperature of the cyclization reaction is preferably −20 to 200° C., more preferably 0 to 100° C.

The reaction time of the cyclization reaction varies depending on the reaction conditions, and is preferably 5 minutes to 72 hours, more preferably 30 minutes to 48 hours.

In cases where Compound (I) was obtained as a free form, it may be converted to a desired salt according to a known method or a method corresponding thereto. Conversely, in cases where it was obtained as a salt, it may be converted to a free form or another desired salt according to a known method or a method corresponding thereto.

Compound (I) may also be used as a prodrug, and examples of the prodrug of Compound (I) include compounds which are converted to Compound (I) by reaction by an enzyme, gastric acid or the like under physiological conditions in a living body, that is, compounds that undergo enzymatic oxidation, reduction or hydrolysis to change into Compound (I); and compounds that undergo hydrolysis by gastric acid or the like to change into Compound (I), which compounds correspond to those wherein a hydroxyl group of Compound (I) was acylated, alkylated, phosphorylated or borated. Preferred particular examples of the prodrug in cases where $R^5$ or $R^6$ of Compound (I) is a hydroxyl group are shown in Table 2, but these examples do not restrict the scope of this disclosure.

TABLE 2

| Compound | Structural formula |
|---|---|
| P1 | (cyclohexane with OH, A-substituent, and O-C(=O)-N(CH₃)₂ carbamate group) |
| P2 | (cyclohexane with OH, A-substituent, and O-C(=O)-O-ethyl carbonate group) |
| P3 | (cyclohexane with OH, A-substituent, and O-C(=O)-O-cyclohexyl carbonate group) |
| P4 | (cyclohexane with OH, A-substituent, and O-C(=O)-C(CH₃)₃ pivalate group) |
| P5 | (cyclohexane with OH, A-substituent, and O-C(=O)-CH₂CH₂-C(=O)OH succinate group) |
| P6 | (cyclohexane with OH, A-substituent, and O-C(=O)-CH₂-NH₂ glycinate group) |

TABLE 2-continued

| Compound | Structural formula |
|---|---|
| P7 | A—[cyclohexane with OH]—O—C(=O)—CH(NH₂)(S)—CH(CH₃)₂ |
| P8 | A—[cyclohexane with OH]—O—CH₂—O—C(=O)—C(CH₃)₃ |
| P9 | A—[cyclohexane with OH]—O—CH(CH₃)—O—C(=O)—O—cyclohexyl |
| P10 | A—[cyclohexane with OH]—O—CH(CH₃)—O—C(=O)—O—ethyl |
| P11 | A—[cyclohexane with OH]—O—CH(CH₃)—O—C(=O)—O—CH(S)(CH(CH₃)₂)(NH₂) |
| P12 | A—[cyclohexane with OH]—O—P(=O)(OH)(OH) |

The prodrug of Compound (I) can be synthesized according to a known method from Compound (I). Further, the prodrug of Compound (I) may be one that changes into Compound (I) under the physiological conditions described in a known document ('Iyakuhin no Kaihatsu' (Development of Drugs), Hirokawa Shoten, 1990, vol. 7, pp. 163-198; Prog. Med. 5, 1985, pp. 2157-2161). By using Compound (I) as a prodrug, its solubility and/or absorbability may be improved.

The excellent analgesic effect, or therapeutic effect on neuropathic pain or therapeutic action against diabetic neuropathic pain, of Compound (I) can be evaluated using an appropriate animal model. Examples of the appropriate animal model for nociceptive pain include mouse acetic acid writhing model, rat or mouse formalin test, rat carrageenin-induced inflammation model, rat hot plate test, and tail-flick test for acute pain.

Examples of the appropriate animal models for neuropathic pain include mouse or rat partial sciatic nerve ligation model and mouse or rat spinal nerve ligation model, and examples of the appropriate animal model for diabetic neuropathic pain include mouse or rat streptozotocin (STZ)-induced diabetic neuropathy model.

Since Compound (I) has an excellent analgesic effect, or therapeutic effect on neuropathic pain or therapeutic effect on diabetic neuropathic pain, the compound can be used as a pharmaceutical, and is preferably used as an analgesic, therapeutic drug for neuropathic pain, or therapeutic drug for diabetic neuropathic pain.

In cases where Compound (I) is used as an analgesic, it is preferably used for nociceptive pain. Examples of the nociceptive pain herein include pain due to injuries such as fracture and incised wound; postoperative pain; sprain pain; bruise pain; joint pain; low back pain; muscle pain; pain after tooth extraction; dental pain; appendicitis; chronic rheumatoid arthritis; rheumatic fever; osteoarthritis; ankylosing spondylitis; spondylosis deformans; cervicobrachial syndrome; periarthritis; cellulitis; acute otitis media; prostatitis; alveolar periostitis; and pain due to inflammatory diseases such as vaginitis. Further, the above-described nociceptive pain include deep pain and visceral pain (e.g., headache; abdominal pain; back pain; chronic pelvic pain syndrome; pain due to endometriosis; pain due to urolithiasis or urethral calculus; colicky pain due to digestive organ disease, pelvic pain; and urologic diseases pain). In cases where Compound (I) is used as an analgesic, examples of more preferred target diseases include chronic rheumatoid arthritis, osteoarthritis, postoperative pain, joint pain, low back pain, muscle pain and dental pain.

Compound (I) is used as a therapeutic drug for neuropathic pain, and also as a therapeutic drug for diabetic neuropathic pain. Examples of the neuropathic pain herein include cancer pain, herpes zoster pain, postherpetic neuralgia, AIDS-related neuralgia and trigeminal neuralgia. The diabetic neuropathic pain herein means pain due to diabetic neuralgia.

Compound (I) is also useful for therapy of acute and chronic pain. Acute pain usually continues for a short period of time, and examples thereof include postoperative pain, pain after tooth extraction and trigeminal neuralgia. Chronic pain is defined as pain that usually continues for 3 to 6 months. It includes somatogenic pain and psychogenic pain, and examples thereof include chronic rheumatoid arthritis, osteoarthritis and postherpetic neuralgia.

A pharmaceutical containing Compound (I) shows an excellent analgesic effect, or therapeutic effect on neuropathic pain or diabetic neuropathic pain, in cases where it was administered to a mammal (e.g., mouse, rat, hamster, rabbit, cat, dog, bovine, sheep, monkey or human), especially human.

Further, Compound (I) may be used not only as an analgesic or a therapeutic drug for neuropathic pain, but also in a therapeutic method for pain or neuropathic pain, or in a therapeutic use for pain or neuropathic pain. Further, Compound (I) may be used in a therapeutic method or therapeutic use for diabetic neuropathic pain.

The dosage form of Compound (I) may be oral or parenteral administration of Compound (I) as it is or after blending of a pharmaceutically acceptable carrier thereto.

Examples of the dosage form of the drug product containing Compound (I) in cases where it is orally administered include tablets (e.g., sugar-coated tablets and film-coated tablets), pills, granules, powders, capsules (e.g., soft capsules and microcapsules), syrups, emulsions and suspensions; examples of the dosage form in cases where it is parenterally administered include injections, impregnating agents, drops and suppositories. It is also effective to formulate the drug into a sustained-release preparation by combining the drug with an appropriate base (e.g., polymer of butyric acid, polymer of glycolic acid, copolymer of butyric acid-glycolic acid, mixture of a polymer of butyric acid and a polymer of glycolic acid, or polyglycerol fatty acid ester).

Preparation of the drug product containing Compound (I) into the above-described dosage form can be carried out according to a known method commonly used in the field of drug formulation. In such a case, the formulation can be produced by inclusion of an excipient, binder, lubricant, disintegrant, sweetener, surfactant, suspending agent, emulsifier and/or the like, which are commonly used in the field of drug formulation.

Preparation of a tablet containing Compound (I) may be carried out by inclusion of an excipient, binder, disintegrant, lubricant and/or the like; and preparation of a pill or granule may be carried out by inclusion of an excipient, binder, disintegrant and/or the like. Preparation of a powder or capsule may be carried out by inclusion of an excipient and/or the like; preparation of a syrup may be carried out by inclusion of a sweetener and/or the like; and preparation of an emulsion or suspension be carried out by inclusion of a surfactant, suspending agent, emulsifier and/or the like.

Examples of the excipient include lactose, glucose, starch, sucrose, microcrystalline cellulose, powdered glycyrrhiza, mannitol, sodium hydrogen carbonate, calcium phosphate and calcium sulfate.

Examples of the binder include starch paste solutions, gum arabic solutions, gelatin solutions, tragacanth solutions, carboxymethylcellulose solutions, sodium alginate solutions and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethylcellulose, methyl cellulose and bentonite.

Examples of the emulsifier include gum arabic, tragacanth, gelatin and polysorbate 80.

Further, in cases where the drug containing Compound (I) is formulated into the above-described dosage form, a coloring agent, preservative, aromatic, corrigent, stabilizer, thickener and/or the like, which are commonly used in the field of drug formulation, may be added.

The daily dose of the formulation varies depending on the conditions and the body weight of the patient, type of the compound, administration route and the like, and is preferably 1 mg to 1000 mg in the case of oral administration to an adult (about 60 kg body weight), which is administered in one time or dividedly in several times. In cases where the formulation is parenterally administered, the daily dose is preferably 0.01 mg to 100 mg per 1 kg body weight, which is intravenously administered.

Compound (I) may also be used after blending with, or in combination with, another drug in an appropriate amount to complement or enhance the therapeutic or prophylactic effect, or to reduce the dose. Compound (I) may be used in combination with, for example, the following drugs.

Examples of antitussive agents, expectorants and antitussive expectorant agents include dextromethorphan, benproperine, dimemorfan, clofedanol, ephedrine, huscode, fominoben, methylephedrine, acetylcysteine, ambroxol, carbocisteine, bromhexine, eprazinone, cherry bark extract, codeine, dihydrocodeine and tipepidine.

Examples of bronchodilators include clenbuterol, cromoglycate, salbutamol, salmeterol, tulobuterol, theophylline and procaterol.

Examples of antipeptic ulcer drugs include azulene, aldioxa, irsogladine, ecabet, omeprazole, ornoprostil, cimetidine, sucralfate, sulpiride, cetraxate and famotidine.

Examples of antibiotics include amoxicillin, azithromycin, erythromycin, clarithromycin, tetracycline and doxycycline.

Examples of narcotic analgesics include opium alkaloid, ethylmorphine, oxycodone, morphine, cocaine, fentanyl and pethidine.

EXAMPLES

Our compounds and methods will now be described in more detail with reference to Reference Examples and Examples. However, the disclosure is not limited thereto.

The names of solvents in the parentheses set forth in NMR data indicate the solvents used for the measurements.

JNM-AL400 type nuclear magnetic resonance apparatus manufactured by JEOL LTD. was used for measuring 400 MHz NMR spectrum. Chemical shifts were referenced to tetramethylsilane and expressed in δ (unit: ppm). Each signal was expressed in s (singlet), d (doublet), t (triplet), q (quartet), quint (quintet), sept (septet), m (multiplet), br (broad), dd (doublet of doublets), dt (doublet of triplets), ddd (doublet of doublet of doublets), dq (doublet of quartets), td (triplet of doublets) or tt (triplet of triplets). IR spectrum was measured using FT/IR-410 manufactured by JASCO Corporation, and ESI-MS spectrum was measured using Micromass ZQ2K manufactured by Waters or 1200LC/MSD manufactured by Agilent Technology. All the solvents used were commercially available. YFLC W-prep2XY manufactured by Yamazen Corporation was used for flash chromatography.

The raw materials of the compounds and synthesis of the intermediates are described as Reference Examples in the following. Among the compounds used in the synthesis of the compounds of Reference Examples, for the compounds whose synthesis method is not described, commercially available compounds were used.

Reference Example 1

8-Ethynyl-1,4-dioxaspiro[4.5]decan-8-ol

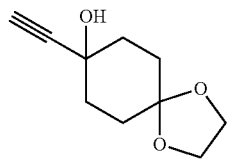

To a solution of trimethylsilylacetylene (27.1 mL, 0.192 mol) in tetrahydrofuran (300 mL), 2.77 M n-butyllithium (solution in n-hexane, 69.3 mL, 0.192 mol) was added dropwise at −76° C. for 30 minutes, and the obtained solution was stirred at the same temperature for 30 minutes. A solution of 1,4-dioxaspiro[4.5]decan-8-one (25.0 g, 0.160 mol) in tetrahydrofuran (100 mL) was added dropwise at −74° C. for 30 minutes, and the obtained solution was stirred at the same temperature for 1 hour and 30 minutes. The reaction solution was poured into saturated aqueous ammonium chloride solution and the resulting solution was extracted with ethyl acetate. The organic layer was washed with brine, dried over anhydrous sodium sulfate and concentrated under reduced pressure.

Methanol (320 mL) was added to the residue to dissolve it, and potassium carbonate (55.3 g, 0.400 mol) was added thereto. The resulting solution was stirred at room temperature for 2 hours and the obtained reaction solution was concentrated under reduced pressure. Distilled water was added to the residue and the resultant was extracted with ethyl acetate. The organic layer was washed with distilled water and brine, dried over anhydrous sodium sulfate and concentrated under reduced pressure. The residue was purified by flash chromatography (silica gel, n-hexane/ethyl acetate) to obtain the captioned compound (29.1 g, 0.160 mol, 100%) as white solid.

$^1$H-NMR (400 MHz, CDCl$_3$) δ: 1.75-2.03 (9H, m), 2.49 (1H, m), 3.95 (4H, s).

ESI-MS: m/z=165 (M−OH)$^+$

Reference Example 2

1-(3-Hydroxy-3-(p-tolyl)propyn-1-yl)cyclohexanol

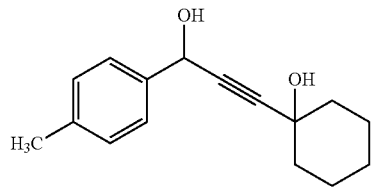

To a solution of 1-ethynylcyclohexanol (500 mg, 4.02 mmol) in tetrahydrofuran (20 mL), 2.77 M n-butyllithium (solution in n-hexane, 3.6 mL, 9.90 mmol) was added dropwise at −78° C., and the obtained solution was stirred at the same temperature for 1 hour. To the reaction solution, p-tolualdehyde (0.52 mL, 4.40 mmol) was added at −78° C., and the obtained solution was allowed to warm gradually to room temperature with stirring. To the reaction solution, distilled water and 1 M hydrochloric acid were added to make the mixture acidic, and the resultant was extracted with ethyl acetate. The organic layer was dried over anhydrous magnesium sulfate and concentrated under reduced pressure. The residue was purified by flash chromatography (silica gel, n-hexane/ethyl acetate) to obtain the captioned compound (598 mg, 2.44 mmol, 61%) as a pale yellow solid.

$^1$H-NMR (400 MHz, CDCl$_3$) δ: 1.18-1.30 (1H, m), 1.47-1.74 (7H, m), 1.89-1.98 (2H, m), 2.08 (1H, brs), 2.22 (1H, brs), 2.36 (3H, s), 5.47 (1H, s), 7.19 (2H, d, J=8.0 Hz), 7.43 (2H, d, J=8.0 Hz).

ESI-MS: m/z=227 (M−OH)$^+$

Reference Example 3

8-(3-Hydroxy-3-(p-tolyl)propyn-1-yl)-1,4-dioxaspiro[4.5]decan-8-ol

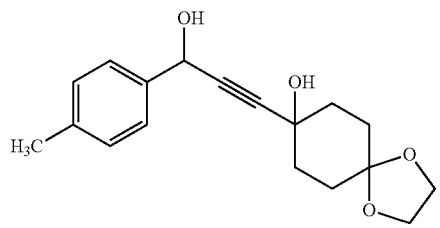

To a solution of 8-ethynyl-1,4-dioxaspiro[4.5]decan-8-ol (Reference Example 1) (15.0 g, 82.3 mmol) in tetrahydrofuran (165 mL), 2.77 M n-butyllithium (solution in n-hexane, 62.4 mL, 172.9 mmol) was added dropwise at −72° C. for 25 minutes, and the obtained solution was stirred at the same temperature for 30 minutes. Thereafter, p-tolualdehyde (10.2 mL, 86.4 mmol) was added dropwise at −72° C. for 5 minutes, and the obtained solution was stirred at the same temperature for 30 minutes. The reaction solution was allowed to warm to room temperature and poured into saturated aqueous ammonium chloride solution. The reaction solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (17.7 g, 58.5 mmol, 71%) as an amorphous product.

$^1$H-NMR (400 MHz, CDCl$_3$) δ: 1.72-1.85 (4H, m), 1.90-2.04 (4H, m), 2.35 (3H, s), 2.55 (1H, s), 2.78 (1H, d, J=6.0 Hz), 3.93 (4H, s), 5.44 (1H, d, J=6.0 Hz), 7.17 (2H, d, J=8.0 Hz), 7.40 (2H, d, J=8.0 Hz).

ESI-MS: m/z=285 (M−OH)$^+$

Reference Example 4

8-(3-Hydroxy-3-(4-methoxyphenyl)propyn-1-yl)-1,4-dioxaspiro[4.5]decan-8-ol

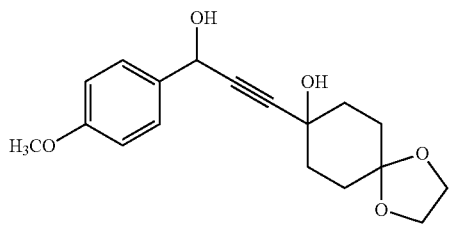

To a solution of 8-ethynyl-1,4-dioxaspiro[4.5]decan-8-ol (Reference Example 1) (5.02 g, 27.6 mmol) in tetrahydrofuran (100 mL), 2.63 M n-butyllithium (solution in n-hexane, 22.0 mL, 57.9 mmol) was added dropwise at −72° C. for 15 minutes, and the obtained solution was stirred at the same temperature for 60 minutes. Thereafter, 4-methoxyaldehyde (3.52 mL, 28.9 mmol) was added dropwise at −72° C. for 10 minutes, and the obtained solution was stirred at the same temperature for 60 minutes. The reaction solution was allowed to warm to room temperature and poured into saturated aqueous ammonium chloride solution. The reaction solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (7.46 g, 23.4 mmol, 85%) as an amorphous product.

$^1$H-NMR (400 MHz, CDCl$_3$) δ: 1.73-1.85 (4H, m), 1.91-2.04 (4H, m), 2.32 (1H, s), 2.52 (1H, d, J=6.1 Hz), 3.81 (3H, s), 3.94 (4H, s), 5.44 (1H, d, J=6.1 Hz), 6.89 (2H, d, J=8.5 Hz), 7.44 (2H, d, J=8.5 Hz).

Reference Example 5

8-(3-(4-Chlorophenyl)-3-hydroxypropyn-1-yl)-1,4-dioxaspiro[4.5]decan-8-ol

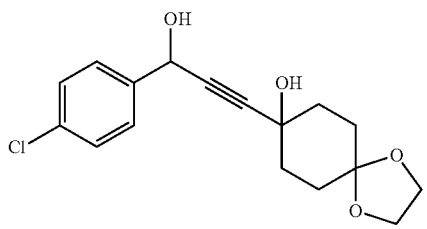

To a solution of 8-ethynyl-1,4-dioxaspiro[4.5]decan-8-ol (Reference Example 1) (5.03 g, 27.6 mmol) in tetrahydrofuran (100 mL), 2.63 M n-butyllithium (solution in n-hexane, 22.1 mL, 57.9 mmol) was added dropwise at −72° C. for 15 minutes, and the obtained solution was stirred at the same temperature for 60 minutes. Thereafter, 4-chlorobenzaldehyde (4.06 g, 28.9 mmol) was added dropwise at −72° C. for 10 minutes, and the obtained solution was stirred at the same temperature for 60 minutes. The reaction solution was allowed to warm to room temperature and poured into saturated aqueous ammonium chloride solution. The reaction solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (8.13 g, 25.2 mmol, 91%) as an amorphous product.

$^1$H-NMR (400 MHz, CDCl$_3$) δ: 1.68-1.81 (4H, m), 1.86-1.90 (4H, m), 3.55 (1H, s), 3.90 (4H, s), 4.03 (1H, d, J=4.2 Hz), 5.41 (1H, d, J=4.2 Hz), 7.28 (2H, d, J=8.3 Hz), 7.41 (2H, d, J=8.3 Hz).

The following compounds were prepared in the same manner as described above.

TABLE 3-1

| Reference Example | Structural Formula | Compound Data |
|---|---|---|
| 6 | (phenyl analog) | $^1$H-NMR (400 MHz, CDCl$_3$) δ: 1.71-1.84 (4H, m), 1.88-2.03 (4H, m), 2.65-3.31 (2H, m), 3.91 (4H, s), 5.47 (1H, d, J = 5.2 Hz), 7.29-7.38 (3H, m), 7.51 (2H, d, J = 8.4 Hz). ESI-MS: m/z = 271 (M − OH)$^+$ |
| 7 | (4-fluorophenyl analog) | $^1$H-NMR (400 MHz, CDCl$_3$) δ: 1.69-1.85 (4H, m), 1.86-2.02 (4H, m), 2.40-3.12 (2H, m), 3.91 (4H, d, J = 1.2 Hz), 5.46 (1H, m), 7.04 (2H, dt, J = 7.6, 8.4 Hz), 7.49 (2H, dd, J = 5.2, 7.6 Hz). ESI-MS: m/z = 289 (M − OH)$^+$ |
| 8 | (3-methylphenyl analog) | $^1$H-NMR (400 MHz, CDCl$_3$) δ: 1.70-1.85 (4H, m), 1.90-2.02 (4H, m), 2.36 (3H, s), 2.36-2.72 (2H, m), 3.93 (4H, s), 5.44 (1H, d, J = 4.8 Hz), 7.13 (1H, d, J = 7.6 Hz), 7.26 (1H, t, J = 7.6 Hz), 7.30 (1H, d, J = 7.6 Hz), 7.33 (1H, s). ESI-MS: m/z = 285 (M − OH)$^+$ |
| 9 | (4-methylthiophenyl analog) | $^1$H-NMR (400 MHz, CDCl$_3$) δ: 1.70-1.85 (4H, m), 1.86-2.02 (4H, m), 2.41 (1H, s), 2.49 (3H, s), 2.71 (1H, s), 3.97 (4H, s), 5.44 (1H, m), 7.25 (2H, d, J = 8.4 Hz), 7.42 (2H, d, J = 8.4 Hz). ESI-MS: m/z = 317 (M − OH)$^+$ |

TABLE 3-1-continued

| Reference Example | Structural Formula | Compound Data |
|---|---|---|
| 10 | | $^1$H-NMR (400 MHz, CDCl$_3$) δ: 1.69-1.84 (6H, m), 1.90-2.01 (4H, m), 3.06 (3H, s), 3.94 (4H, s), 5.57 (1H, d, J = 5.4 Hz), 7.72 (2H, d, J = 8.3 Hz), 7.93 (2H, d, J = 8.3 Hz). ESI-MS: m/z = 349 (M − OH)$^+$ |
| 11 | | $^1$H-NMR (400 MHz, CD$_3$OD) δ: 1.73-1.76 (4H, m), 1.82-1.94 (4H, m), 2.43 (3H, s), 3.91-3.95 (5H, m), 5.61 (1H, d, J = 1.6 Hz), 7.15-7.20 (3H, m), 7.59-7.61 (1H, m). ESI-MS: m/z = 285 (M − OH)$^+$ |

TABLE 3-2

| Reference Example | Structural Formula | Compound Data |
|---|---|---|
| 12 | | $^1$H-NMR (400 MHz, CDCl$_3$) δ: 1.72-1.85(4H, m), 1.90-2.04(4H, m), 2.42(1H, s), 3.25(1H, d, J = 2.4 Hz), 3.94 (4H, s), 4.02(3H, s), 5.65(1H, d, J = 2.4 Hz), 6.92(1H, dd, J = 5.2, 7.2 Hz), 7.80(1H, dd, J = 2.4, 7.2 Hz), 8.13(1H, dd, J = 2.4, 5.2 Hz). ESI-MS: m/z = 302 (M − OH)$^+$ |
| 13 | | $^1$H-NMR (400 MHz, CDCl$_3$) δ: 1.63(1H, s), 1.75-1.83(4H, m), 1.95-2.05(4H, m), 2.62(1H, s), 3.94(4H, s), 5.56(1H, s), 7.64(4H, s). ESI-MS: m/z = 339 (M − OH)$^+$ |

Reference Example 14

3-(1-Hydroxycyclohexyl)-1-(p-tolyl)-2-propyn-1-one

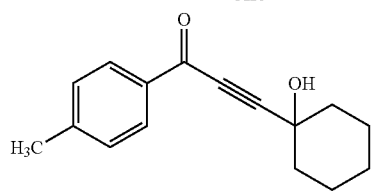

To a solution of 1-(3-hydroxy-3-(p-tolyl)propyn-1-yl)cyclohexanol (Reference Example 2) (593 mg, 2.42 mmol) in dichloromethane (20 mL), manganese dioxide (1.15 g, 13.2 mmol) was added, and the obtained solution was stirred at room temperature for 5 hours. The reaction solution was filtered through Celite and the filtrate was concentrated under reduced pressure. The residue was purified by flash chromatography (silica gel, n-hexane/ethyl acetate) to obtain the captioned compound (534 mg, 2.20 mmol, 91%) as a light yellow oily product.

$^1$H-NMR (400 MHz, CDCl$_3$) δ: 1.28-1.39 (1H, m), 1.55-1.84 (7H, m), 2.02-2.11 (2H, m), 2.23 (1H, brs), 2.43 (3H, s), 7.28 (2H, d, J=8.0 Hz), 8.02 (2H, d, J=8.0 Hz).

Reference Example 15

3-(8-Hydroxy-1,4-dioxaspiro[4.5]decan-8-yl)-1-(p-tolyl)-2-propyn-1-one

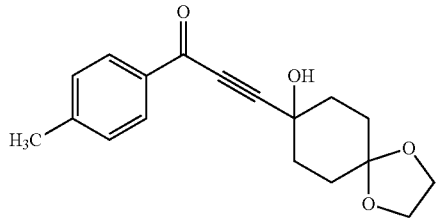

To a solution of 8-(3-hydroxy-3-(p-tolyl)propyn-1-yl)-1,4-dioxaspiro[4.5]decan-8-ol (Reference Example 3) (17.5 g, 57.9 mmol) in dichloromethane (289 mL), manganese dioxide (29.6 g, 289 mmol) was added, and the obtained solution was stirred at room temperature for 15 hours. The reaction solution was filtered through Celite and the filtrate was concentrated under reduced pressure. The residue was purified by flash chromatography (silica gel, n-hexane/ethyl acetate) to obtain the captioned compound (14.3 g, 47.6 mmol, 82%) as an oily product.

$^1$H-NMR (400 MHz, CDCl$_3$) δ: 1.79-1.85 (2H, m), 1.87-1.93 (2H, m), 2.04-2.15 (4H, m), 2.20 (1H, s), 2.43 (3H, s), 3.97 (4H, s), 7.28 (2H, d, J=8.0 Hz), 8.00 (2H, d, J=8.0 Hz).

ESI-MS: m/z=284 (M−OH)$^+$

Reference Example 16

3-(8-Hydroxy-1,4-dioxaspiro[4.5]decan-8-yl)-1-(6-methylpyridin-3-yl)-2-propyn-1-one

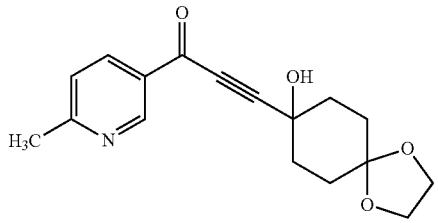

To a solution of 8-ethynyl-1,4-dioxaspiro[4.5]decan-8-ol (Reference Example 1) (592 mg, 3.25 mmol) in tetrahydrofuran (6 mL), 2.63 M n-butyllithium (solution in n-hexane, 2.6 mL, 6.82 mmol) was added dropwise at −78° C. for 5 minutes, and the obtained solution was stirred at the same temperature for 30 minutes. Thereafter, a solution of N-methoxy-N-methyl-6-methyl-nicotinamide (614.5 mg, 3.41 mmol) in tetrahydrofuran (5 ml) was added dropwise at −78° C. for 20 minutes, and the obtained solution was stirred at the same temperature for 30 minutes. The reaction solution was allowed to warm to room temperature and poured into saturated aqueous ammonium chloride solution. The reaction solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (626.3 mg, 2.08 mmol, 65%) as a pale yellow solid.

$^1$H-NMR (400 MHz, CDCl$_3$) δ: 1.76-1.83 (2H, m), 1.87-1.94 (2H, m), 2.04-2.10 (2H, m), 2.12-2.19 (2H, m), 2.30 (1H, s), 2.66 (3H, s), 3.97 (4H, s), 7.29 (1H, d, J=8.0 Hz), 8.22 (1H, dd, J=2.4, 8.0 Hz), 9.21 (1H, d, J=2.4 Hz).

ESI-MS: m/z=284 (M−OH)$^+$

Reference Example 17

3-(8-Hydroxy-1,4-dioxaspiro[4.5]decan-8-yl)-1-(4-methoxyphenyl)-2-propyn-1-one

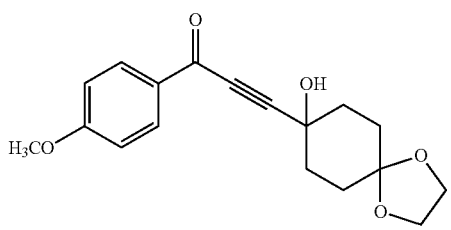

To a solution of 8-(3-hydroxy-3-(4-methoxyphenyl)propyn-1-yl)-1,4-dioxaspiro[4.5]decan-8-ol (Reference Example 4) (7.10 g, 22.3 mmol) in dichloromethane (100 mL), manganese dioxide (9.69 g, 112 mmol) was added, and the obtained solution was stirred at room temperature for 18 hours. The reaction solution was filtered through Celite and the filtrate was concentrated under reduced pressure. The residue was purified by flash chromatography (silica gel, n-hexane/ethyl acetate) to obtain the captioned compound (5.45 g, 17.2 mmol, 77%) as an oily product.

$^1$H-NMR (400 MHz, CDCl$_3$) δ: 1.78-1.93 (4H, m), 2.03-2.17 (4H, m), 2.27 (1H, s), 3.89 (3H, s), 3.97 (4H, s), 6.95 (2H, d, J=9.0 Hz), 8.08 (2H, d, J=9.0 Hz).

ESI-MS: m/z=299 (M−OH)$^+$

Reference Example 18

1-(4-Chlorophenyl)-3-(8-hydroxy-1,4-dioxaspiro[4.5]decan-8-yl)-2-propyn-1-one

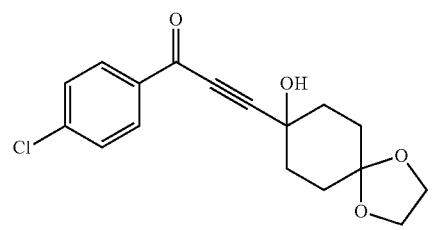

To a solution of 8-(3-(4-chlorophenyl)-3-hydroxypropyn-1-yl)-1,4-dioxaspiro[4.5]decan-8-ol (Reference Example 5) (7.70 g, 23.9 mmol) in dichloromethane (120 mL), manganese dioxide (10.4 g, 119 mmol) was added, and the obtained solution was stirred at room temperature for 18 hours. The reaction solution was filtered through Celite and the filtrate was concentrated under reduced pressure. The residue was purified by flash chromatography (silica gel, n-hexane/ethyl acetate) to obtain the captioned compound (5.45 g, 17.0 mmol, 71%) as an oily product.

$^1$H-NMR (400 MHz, CDCl$_3$) δ: 1.77-1.94 (4H, m), 2.04-2.19 (4H, m), 2.15 (1H, s), 3.98 (4H, s), 7.47 (2H, d, J=8.5 Hz), 8.04 (2H, d, J=8.5 Hz).

ESI-MS: m/z=303 (M−OH)$^+$

The following compounds were prepared in the same manner as described above.

TABLE 4-1

| Reference Example | Structural Formula | Compound Data |
|---|---|---|
| 19 | | $^1$H-NMR (400 MHz, CDCl$_3$) δ: 1.78-1.94(4H, m), 2.04-2.20(4H, m), 2.33(1H, s), 3.97(4H, s), 7.49(2H, t, J = 7.2 Hz), 7.62(1H, t, J = 7.2 Hz), 7.69(2H, d, J = 7.2 Hz). ESI-MS: m/z = 269 (M − OH)$^+$ |
| 20 | | $^1$H-NMR (400 MHz, CDCl$_3$) δ: 1.74-1.94(4H, m), 2.05-2.19(4H, m), 2.60-2.82(1H, m), 3.97(4H, s), 7.14(2H, dd, J = 7.6, 8.4 Hz), 7.49(2H, dd, J = 5.2, 7.6 Hz). ESI-MS: m/z = 287 (M − OH)$^+$ |
| 21 | | $^1$H-NMR (400 MHz, CDCl$_3$) δ: 1.77-1.94(4H, m), 2.04-2.18(4H, m), 2.20(1H, s), 2.43(3H, s), 3.97(4H, s), 7.37 (1H, t, J = 7.6 Hz), 7.44(1H, d, J = 7.6 Hz), 7.91(1H, s), 7.92(1H, d, J = 7.6 Hz). ESI-MS: m/z = 283 (M − OH)$^+$ |
| 22 | | $^1$H-NMR (400 MHz, CDCl$_3$) δ: 1.77-1.94(4H, m), 2.02-2.18(4H, m), 2.05(1H, s), 2.54(3H, s), 3.97(4H, s), 7.27 (2H, d, J = 8.8 Hz), 8.00(2H, d, J = 8.8 Hz). ESI-MS: m/z = 315 (M − OH)$^+$ |
| 23 | | $^1$H-NMR (400 MHz, CDCl$_3$) δ: 1.77-1.83(2H, m), 1.89-1.95(2H, m), 2.05-2.20(4H, m), 2.37(1H, s), 3.10(3H, s), 3.98(4H, s), 8.08(2H, d, J = 8.1 Hz), 8.29(2H, d, J = 8.1 Hz). ESI-MS: m/z = 347 (M − OH)$^+$ |

TABLE 4-2

| Reference Example | Structural Formula | Compound Data |
|---|---|---|
| 24 | | ¹H-NMR (400 MHz, CDCl3) δ: 1.77-1.83 (2H, m), 1.86-1.92 (2H, m), 2.02-2.08 (2H, m), 2.01-2.14 (2H, m), 2.62 (3H, s), 3.97 (4H, s), 7.24-7.26 (1H, m), 7.33 (1H, dd, J = 7.2, 7.6 Hz), 7.45 (1H, dd, J = 7.2, 8.0 Hz), 8.16 (1H, d, J = 8.0 Hz).<br>ESI-MS: m/z = 283 (M − OH)⁺ |
| 25 | | ¹H-NMR (400 MHz, CDCl3) δ: 1.79-1.91 (4H, m), 2.01-2.15 (4H, m), 2.38 (1H, s), 3.97 (4H, s), 4.08 (3H, s), 6.99-7.02 (1H, m), 8.25-8.28 (1H, m), 8.36-8.37 (1H, m). |
| 26 | | ¹H-NMR (400 MHz, CDCl3) δ: 1.81-1.84 (2H, m), 1.89-1.94 (2H, m), 2.09-2.17 (4H, m), 2.38 (1H, s), 3.98 (4H, s), 7.76 (2H, d, J = 8.0 Hz), 8.21 (2H, d, J = 8.0 Hz). |
| 27 | | ¹H-NMR (400 MHz, CDCl3) δ: 1.76-1.95 (4H, m), 2.04-2.20 (5H, m), 2.36 (3H, d, J = 2.0 Hz), 3.97 (4H, s), 7.31 (1H, t, J = 8.0 Hz), 7.71 (1H, d, J = 10.0 Hz), 7.81 (1H, d, J = 8.0 Hz).<br>ESI-MS: m/z = 319 (M + H)⁺ |
| 28 | | ¹H-NMR (400 MHz, CDCl3) δ: 1.75-1.96 (4H, m), 2.03-2.25 (4H, m), 2.47-2.60 (1H, m), 3.98 (4H, s), 7.77-7.82 (2H, m), 8.16-8.23 (2H, m).<br>ESI-MS: m/z = 312 (M + H)⁺ |
| 29 | | ¹H-NMR (400 MHz, CDCl3) δ: 1.26 (3H, t, J = 7.6 Hz), 1.78-1.94 (4H, m), 2.03-2.19 (4H, m), 2.27 (1H, br), 2.72 (2H, q, J = 7.6 Hz), 3.98 (4H, s), 7.30 (2H, d, J = 8.4 Hz), 8.03 (2H, d, J = 8.4 Hz).<br>ESI-MS: m/z = 315 (M + H)⁺ |

Reference Example 30

8-(1-(4-Methoxyphenyl)-5-(p-tolyl)-1H-pyrazol-3-yl)-1,4-dioxaspiro[4.5]decan-8-ol

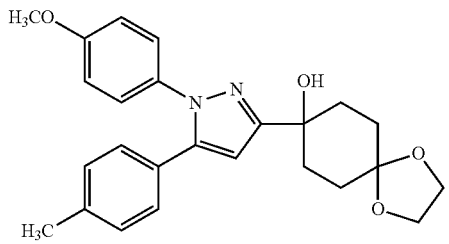

To a solution of 4-methoxyphenylhydrazine hydrochloride (7.35 g, 42.1 mmol) in ethanol (76.6 mL), triethylamine (5.87 mL, 42.1 mmol) was added dropwise, and the obtained solution was stirred at room temperature for 30 minutes. To the reaction solution, a solution of 3-(8-hydroxy-1,4-dioxaspiro[4.5]decan-8-yl)-1-(p-tolyl)-2-propyn-1-one (Reference Example 15) (11.5 g, 38.3 mmol) in ethanol (76.6 mL) was added dropwise, and the obtained solution was stirred at room temperature for 15 hours. Thereafter, the reaction solution was concentrated under reduced pressure. Water was added to the residue and the resultant was extracted with ethyl acetate. The organic layer was washed with 1 M hydrochloric acid, distilled water and brine, dried over anhydrous magnesium sulfate and concentrated under reduced pressure. The residue was purified by flash chromatography (silica gel, n-hexane/ethyl acetate) to obtain the captioned compound (14.7 g, 35.0 mmol, 91%) as an amorphous product.

$^1$H-NMR (400 MHz, CDCl$_3$) δ: 1.71-1.74 (2H, m), 1.99-2.25 (6H, m), 2.33 (3H, s), 2.71 (1H, s), 3.81 (3H, s), 3.96-4.01 (4H, m), 6.39 (1H, s), 6.84 (2H, d, J=8.0 Hz), 7.09 (4H, s), 7.21 (2H, d, J=8.0 Hz).

ESI-MS: m/z=421 (M+H)$^+$

Reference Example 31

8-(1-(4-Methoxyphenyl)-5-(6-methylpyridin-3-yl)-1H-pyrazol-3-yl)-1,4-dioxaspiro[4.5]decan-8-ol

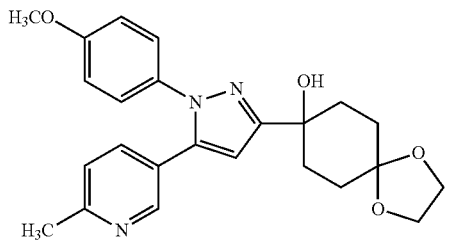

To a solution of 4-methoxyphenylhydrazine hydrochloride (359 mg, 2.06 mmol) in ethanol (4 mL), triethylamine (286 μL, 2.06 mmol) was added dropwise, and the obtained solution was stirred at room temperature for 30 minutes. To the reaction solution, a solution of 3-(8-hydroxy-1,4-dioxaspiro[4.5]decan-8-yl)-1-(6-methylpyridin-3-yl)-2-propyn-1-one (Reference Example 16) (563.7 mg, 1.87 mmol) in ethanol (5.4 mL) was added dropwise, and the obtained solution was stirred at room temperature for 22 hours. Thereafter, the reaction solution was concentrated under reduced pressure. Water was added to the residue and the resultant was extracted with ethyl acetate. The organic layer was washed with distilled water and brine, dried over anhydrous magnesium sulfate and concentrated under reduced pressure. The residue was purified by flash chromatography (silica gel, n-hexane/ethyl acetate) to obtain the captioned compound (177 mg, 0.42 mmol, 22%) as an amorphous product.

$^1$H-NMR (400 MHz, CDCl$_3$) δ: 1.72-1.75 (2H, m), 2.00-2.03 (2H, m), 2.07-2.14 (2H, m), 2.19-2.26 (2H, m), 2.55 (3H, s), 2.65 (1H, s), 3.81 (3H, s), 3.96-4.03 (4H, m), 6.47 (1H, s), 6.86 (2H, d, J=8.8 Hz), 7.06 (1H, d, J=8.0 Hz), 7.20 (2H, d, J=8.8 Hz), 7.33 (1H, dd, J=2.2, 8.0 Hz), 8.40 (1H, d, J=2.2 Hz).

ESI-MS: m/z=422 (M+H)$^+$

Reference Example 32

8-(1,5-Bis(4-methoxyphenyl)-1H-pyrazol-3-yl)-1,4-dioxaspiro[4.5]decan-8-ol

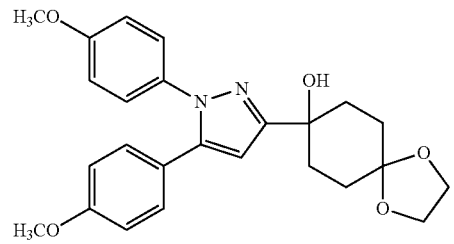

To a solution of 3-(8-hydroxy-1,4-dioxaspiro[4.5]decan-8-yl)-1-(4-methoxyphenyl)-2-propyn-1-one (Reference Example 17) (700 mg, 2.24 mmol) in ethanol (4.5 mL), a solution of 4-methoxyphenylhydrazine hydrochloride (470 mg, 2.69 mmol) and triethylamine (0.74 mL, 5.41 mmol) in ethanol (4.5 mL) was added, and the obtained solution was stirred at room temperature for 20 hours. The reaction solution was concentrated under reduced pressure. Distilled water was added to the residue and the resultant was extracted with ethyl acetate. The organic layer was dried over anhydrous magnesium sulfate and concentrated under reduced pressure. The residue was purified by flash chromatography (silica gel, n-hexane/ethyl acetate) to obtain the captioned compound (864 mg, 1.98 mmol, 88%) as a white amorphous product.

$^1$H-NMR (400 MHz, CDCl$_3$) δ: 1.68-1.77 (2H, m), 1.96-2.26 (6H, m), 2.70 (1H, brs), 3.80 (3H, s), 3.81 (3H, s), 3.94-4.04 (4H, m), 6.37 (1H, s), 6.81 (2H, d, J=8.8 Hz), 6.85 (2H, d, J=8.8 Hz), 7.13 (2H, d, J=8.8 Hz), 7.21 (2H, d, J=8.8 Hz).

ESI-MS: m/z=437 (M+H)$^+$

Reference Example 33

8-(5-(4-Chlorophenyl)-1-(4-methoxyphenyl)-1H-pyrazol-3-yl)-1,4-dioxaspiro[4.5]decan-8-ol

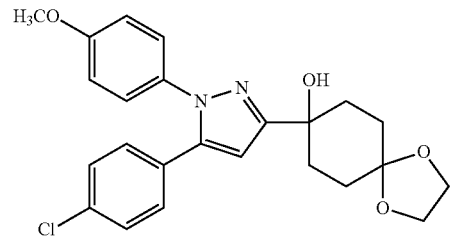

To a solution of 4-methoxyphenylhydrazine hydrochloride (457 mg, 2.62 mmol) in ethanol (4.4 mL), triethylamine (0.730 mL, 5.24 mmol) was added dropwise, and the obtained solution was stirred at room temperature for 30 minutes. To the reaction solution, a solution of 1-(4-chlorophenyl)-3-(8-hydroxy-1,4-dioxaspiro[4.5]decan-8-yl)-2-propyn-1-one (Reference Example 18) (700 mg, 2.18 mmol) in ethanol (4.4 mL) was added dropwise, and the obtained solution was stirred at room temperature for 14 hours. Thereafter, the reaction solution was concentrated under reduced pressure. Water was added to the residue and the resultant was extracted with ethyl acetate. The organic layer was washed with 1 M hydrochloric acid, distilled water and brine, dried over anhydrous magnesium sulfate and concentrated under reduced pressure. The residue was purified by flash chromatography (silica gel, n-hexane/ethyl acetate) to obtain the captioned compound (756 mg, 1.71 mmol, 79%) as an amorphous product.

$^1$H-NMR (400 MHz, CDCl$_3$) δ: 1.69-1.76 (2H, m), 1.97-2.25 (6H, m), 2.66 (1H, brs), 3.82 (3H, s), 3.94-4.03 (4H, m), 6.43 (1H, s), 6.85-6.87 (2H, m), 7.13 (2H, d, J=8.4 Hz), 7.19 (2H, d, J=8.4 Hz), 7.25-7.27 (2H, m).

ESI-MS: m/z=441 (M+H)$^+$

Reference Example 34

8-(1-(4-Chlorophenyl)-5-(p-tolyl)-1H-pyrazol-3-yl)-1,4-dioxaspiro[4.5]decan-8-ol

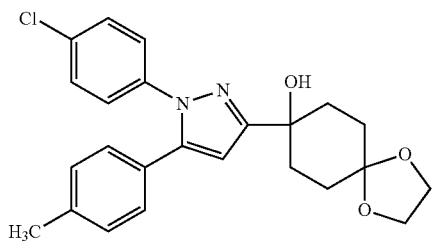

To a solution of 4-chlorophenylhydrazine hydrochloride (418 mg, 2.33 mmol) in ethanol (4.8 mL), triethylamine (5.87 mL, 42.1 mmol) was added dropwise, and the obtained solution was stirred at room temperature for 30 minutes. To the reaction solution, a solution of 3-(8-hydroxy-1,4-dioxaspiro[4.5]decan-8-yl)-1-(p-tolyl)-2-propyn-1-one (Reference Example 15) (698 mg, 2.32 mmol) in ethanol (4.7 mL) was added dropwise, and the obtained solution was stirred at room temperature for 14 hours. Thereafter, the reaction solution was concentrated under reduced pressure. Water was added to the residue and the resultant was extracted with ethyl acetate. The organic layer was washed with distilled water and brine, dried over anhydrous sodium sulfate and concentrated under reduced pressure. The residue was purified by flash chromatography (silica gel, n-hexane/ethyl acetate) to obtain the captioned compound (948 mg, 2.23 mmol, yield: 96%) as an amorphous product.

$^1$H-NMR (400 MHz, CDCl$_3$) δ: 1.71-1.75 (2H, m), 1.98-2.14 (4H, m), 2.17-2.25 (2H, m), 2.36 (3H, s), 2.62 (1H, s), 3.96-4.03 (4H, m), 6.41 (1H, s), 7.09 (2H, d, J=8.0 Hz), 7.13 (2H, d, J=8.0 Hz), 7.22-7.30 (4H, m).

ESI-MS: m/z=407 (M−OH)$^+$

The following compounds were prepared in the same manner as described above.

TABLE 5-1

| Reference Example | Structural Formula | Compound Data |
|---|---|---|
| 35 | | $^1$H-NMR (400 MHz, CDCl$_3$) δ: 1.72-1.75(2H, m), 1.99 (3H, s), 2.02-2.08(2H, m), 2.11-2.15(2H, m), 2.18-2.26 (2H, m), 2.70(1H, s), 3.75(3H, s), 3.95-4.03(4H, m), 6.31 (1H, s), 6.75(2H, d, J = 8.8 Hz), 7.10-7.12(2H, m), 7.15-7.19(4H, m). ESI-MS: m/z = 421 (M + H)$^+$ |
| 36 | | $^1$H-NMR (400 MHz, CDCl$_3$) δ: 1.72-1.75(2H, m), 2.00-2.13(4H, m), 2.19-2.26(2H, m), 2.69(1H, s), 3.07(3H, s), 3.83(3H, s), 3.96-4.02(4H, m), 6.55(1H, s), 6.88(2H, d, J = 8.8 Hz), 7.18(2H, d, J = 8.8 Hz), 7.40(2H, d, J = 8.4 Hz), 7.85(2H, d, J = 8.4 Hz). ESI-MS: m/z = 467 (M − OH)$^+$ |

TABLE 5-1-continued

| Reference Example | Structural Formula | Compound Data |
|---|---|---|
| 37 | 4-F-C6H4 and 4-Cl-C6H4 substituted pyrazole connected to 4-hydroxycyclohexane-1,1-dioxolane spiro | $^1$H-NMR (400 MHz, CDCl$_3$) δ: 1.68-1.76(2H, m), 1.96-2.26(6H, m), 2.67(1H, s), 3.94-4.03(4H, m), 6.45(1H, s), 7.00-7.17(2H, m), 7.10-7.15(2H, m), 7.21-7.31(4H, m). ESI-MS: m/z = 429 (M + H)$^+$ |
| 38 | 4-Cl-C6H4 and 4-Cl-C6H4 substituted pyrazole connected to 4-hydroxycyclohexane-1,1-dioxolane spiro | $^1$H-NMR (400 MHz, CDCl$_3$) δ: 1.69-1.76(2H, m), 2.16-2.25(2H, m), 1.96-2.23(4H, m), 2.63(1H, s), 3.94-4.03 (4H, m), 6.45(1H, s), 7.14(2H, d, J = 8.4 Hz), 7.21(2H, d, J = 8.4 Hz), 7.29-7.32(4H, m). ESI-MS: m/z = 445 (M + H)$^+$ |
| 39 | phenyl and 4-Cl-C6H4 substituted pyrazole connected to 4-hydroxycyclohexane-1,1-dioxolane spiro | $^1$H-NMR (400 MHz, CDCl$_3$) δ: 1.70-1.76(2H, m), 1.98-2.14(4H, m), 2.18-2.25(2H, m), 2.68(1H, s), 3.95-4.02 (4H, m), 6.45(1H, s), 7.13-7.15(2H, m), 7.25-7.37(7H, m). ESI-MS: m/z = 411 (M + H)$^+$ |

TABLE 5-2

| Reference Example | Structural Formula | Compound Data |
|---|---|---|
| 40 | 2,4-diCl-C6H3 and 4-Cl-C6H4 substituted pyrazole connected to 4-hydroxycyclohexane-1,1-dioxolane spiro | $^1$H-NMR (400 MHz, CDCl$_3$) δ: 1.69-1.77 (2H, m), 1.99-2.12 (4H, m), 2.18-2.26 (2H, m), 2.57 (1H, brs), 3.96-4.02 (4H, m), 6.49-6.51 (1H, m), 7.07-7.10 (2H, m), 7.23-7.37 (4H, m), 7.43-7.45 (1H, m). ESI-MS: m/z = 479 (M + H)$^+$ |
| 41 | 4-MeO-C6H4 and 3-Me-C6H4 substituted pyrazole connected to 4-hydroxycyclohexane-1,1-dioxolane spiro | $^1$H-NMR (400 MHz, CDCl$_3$) δ: 1.70-1.76 (2H, m), 1.98-2.14 (4H, m), 2.17-2.26 (2H, m), 2.29 (3H, s), 2.74 (1H, brs), 3.80 (3H, s), 3.95-4.02 (4H, m), 6.41 (1H, s), 6.84 (2H, d, J = 8.8 Hz), 6.92-6.96 (1H, m), 7.08-7.17 (3H, m), 7.21 (2H, d, J = 8.8 Hz). ESI-MS: m/z = 421 (M + H)$^+$ |

TABLE 5-2-continued

| Reference Example | Structural Formula | Compound Data |
|---|---|---|
| 42 | (4-fluorophenyl / 4-methylphenyl pyrazole with cyclohexanone ketal and OH) | $^1$H-NMR (400 MHz, CDCl$_3$) δ: 1.70-1.76 (2H, m), 1.98-2.04 (2H, m), 2.06-2.14 (2H, m), 2.18-2.25 (2H, m), 2.35 (3H, s), 2.62 (1H, s), 3.96-4.03 (4H, m), 6.41 (1H, s), 6.99-7.04 (2H, m), 7.08 (2H, d, J = 8.0 Hz), 7.11 (2H, d, J = 8.0 Hz), 7.25-7.28 (2H, m).<br>ESI-MS: m/z = 391 (M − OH)$^+$ |
| 43 | (bis-4-methylphenyl pyrazole with cyclohexanone ketal and OH) | $^1$H-NMR (400 MHz, CDCl$_3$) δ: 1.70-1.76 (2H, m), 1.98-2.04 (2H, m), 2.07-2.14 (2H, m), 2.18-2.25 (2H, m), 2.34 (3H, s), 2.35 (3H, s), 2.70 (1H, s), 3.95-4.02 (4H, m), 6.40 (1H, s), 7.08-7.11 (4H, m), 7.12 (2H, d, J = 8.4 Hz), 7.17 (2H, d, J = 8.4 Hz).<br>ESI-MS: m/z = 387 (M − OH)$^+$ |

TABLE 5-3

| Reference Example | Structural Formula | Compound Data |
|---|---|---|
| 44 | (phenyl / 4-methylphenyl pyrazole with cyclohexanone ketal and OH) | $^1$H-NMR (400 MHz, CDCl$_3$) δ: 1.71-1.77(2H, m), 1.98-2.05(2H, m), 2.07-2.14(2H, m), 2.18-2.26(2H, m), 2.34 (3H, s), 2.69(1H, s), 3.96-4.03(4H, m), 6.42(1H, s), 7.09-7.11(4H, m), 7.26-7.35(5H, m).<br>ESI-MS: m/z = 373 (M − OH)$^+$ |
| 45 | (4-methoxyphenyl / 4-fluorophenyl pyrazole with cyclohexanone ketal and OH) | $^1$H-NMR (400 MHz, CDCl$_3$) δ: 1.70-1.76(2H, m), 1.98-2.08(2H, m), 2.09-2.14(2H, m), 2.17-2.25(2H, m), 2.66 (1H, s), 3.81(3H, s), 3.95-4.03(4H, m), 6.41(1H, s), 6.83-6.87(2H, m), 6.96-7.01(2H, m), 7.16-7.20(4H, m).<br>ESI-MS: m/z = 407 (M − OH)$^+$ |
| 46 | (4-chlorophenyl / 4-fluorophenyl pyrazole with cyclohexanone ketal and OH) | $^1$H-NMR (400 MHz, CDCl$_3$) δ: 1.70-1.76(2H, m), 1.97-2.08(2H, m), 2.09-2.14(2H, m), 2.17-2.25(2H, m), 2.59 (1H, s), 3.95-4.03(4H, m), 6.43(1H, s), 6.99-7.05(2H, m), 7.16-7.23(4H, m), 7.28-7.32(2H, m).<br>ESI-MS: m/z = 411 (M − OH)$^+$ |

TABLE 5-3-continued

| Reference Example | Structural Formula | Compound Data |
|---|---|---|
| 47 | | $^1$H-NMR (400 MHz, CDCl$_3$) δ: 1.70-1.76(2H, m), 1.98-2.07(2H, m), 2.09-2.14(2H, m), 2.17-2.25(2H, m), 2.60 (1H, s), 3.95-4.03(4H, m), 6.43(1H, s), 6.98-7.06(4H, m), 7.15-7.19(2H, m), 7.22-7.26(2H, m).<br>ESI-MS: m/z = 395 (M – OH)$^+$ |

TABLE 5-4

| Reference Example | Structural Formula | Compound Data |
|---|---|---|
| 48 | | $^1$H-NMR (400 MHz, CDCl$_3$) δ: 1.71-1.77(2H, m), 1.99-2.05(2H, m), 2.06-2.15(2H, m), 2.18-2.26(2H, m), 2.66 (1H, s), 3.95-4.03(4H, m), 6.43(1H, s), 6.96-7.02(2H, m), 7.16-7.21(2H, m), 7.25-7.36(5H, m).<br>ESI-MS: m/z = 377 (M – OH)$^+$ |
| 49 | | $^1$H-NMR (400 MHz, CDCl$_3$) δ: 1.70-1.76(2H, m), 1.98-2.05(2H, m), 2.06-2.14(2H, m), 2.17-2.25(2H, m), 2.35 (3H, s), 2.68(1H, s), 3.95-4.03(4H, m), 6.41(1H, s), 6.96-7.02(2H, m), 7.11-7.21(6H, m).<br>ESI-MS: m/z = 391 (M – OH)$^+$ |
| 50 | | $^1$H-NMR (400 MHz, CDCl$_3$) δ: 1.71-1.77(2H, m), 1.98-2.03(2H, m), 2.06-2.13(2H, m), 2.18-2.26(2H, m), 2.38 (3H, s), 2.60(1H, s), 3.06(3H, s), 3.96-4.03(4H, m), 6.47 (1H, s), 7.11(2H, d, J = 8.0 Hz), 7.16(2H, d, J = 8.0 Hz), 7.50(2H, d, J = 8.4 Hz), 7.87(2H, d, J = 8.4 Hz).<br>ESI-MS: m/z = 451 (M – OH)$^+$ |
| 51 | | $^1$H-NMR (400 MHz, CDCl$_3$) δ: 1.72-1.75(2H, m), 2.02-2.14(4H, m), 2.19-2.23(2H, m), 2.66(1H, s), 3.67(3H, s), 3.79(3H, s), 3.98-4.01(4H, m), 6.47(1H, s), 6.80-6.88(3H, m), 7.15-7.17(2H, m), 7.44(1H, dd, J = 2.0, 5.2 Hz), 8.15 (1H, dd, J = 2.0, 8.4 Hz).<br>ESI-MS: m/z = 438 (M + H)$^+$ |

TABLE 5-5

| Reference Example | Structural Formula | Compound Data |
|---|---|---|
| 52 | ![structure] | $^1$H-NMR (400 MHz, CDCl3) δ: 1.60(2H, m), 1.73(2H, d, J = 12.4 Hz), 2.10(2H, td, J = 3.4, 12.8 Hz), 2.22(2H, td, J = 3.9, 12.4 Hz), 3.80(3H, s), 3.96-4.03(4H, m), 6.44(1H, s), 6.83-6.85(2H, m), 7.18-7.22(4H, m), 7.26-7.30(3H, m). |
| 53 | ![structure] | $^1$H-NMR (400 MHz, CDCl3) δ: 1.73(2H, d, J = 12.0 Hz), 2.01(2H, d, J = 12.4 Hz), 2.10(2H, td, J = 3.2 Hz), 2.22 (2H, td, J = 3.2, J = 12.4 Hz), 2.24(3H, s), 3.96-4.03(4H, m), 6.44(1H, s), 7.12(2H, d, J = 8.4 Hz), 7.16(2H, d, J = 8.8 Hz), 7.21-7.23(2H, m), 7.27-7.30(3H, m). ESI-MS: m/z = 391 (M + H)$^+$ |
| 54 | ![structure] | $^1$H-NMR (400 MHz, CDCl3) δ: 1.73(2H, d, J = 12.4 Hz), 1.99(2H, d, J = 12.4 Hz), 2.10(2H, td, J = 3.2, 12.4 Hz), 2.21(2H, td, J = 3.6, 12.4 Hz), 2.25(3H, s), 2.73(1H, s), 3.80(3H, s), 3.96-4.03(4H, m), 6.37(1H, s), 6.82(2H, m), 7.09-7.18(6H, m). ESI-MS: m/z = 421 (M + H)$^+$ |
| 55 | ![structure] | $^1$H-NMR (400 MHz, CDCl3) δ: 1.70(2H, d, J = 13.6 Hz), 2.01(2H, d, J = 9.2 Hz), 2.10(2H, td, J = 3.6, 12.8 Hz), 2.21 (2H, td, J = 3.6, 12.4 Hz), 2.66(1H, s), 3.80(3H, s), 3.95-4.03(4H, m), 6.39(1H, s), 6.83(2H, ddd, J = 9.2 Hz), 7.01 (2H, t, J = 8.8 Hz), 7.11(2H, d, J = 8.8 Hz), 7.26(2H, t, J = 6.0 Hz). ESI-MS: m/z = 425 (M + H)$^+$ |

TABLE 5-6

| Reference Example | Structural Formula | Compound Data |
|---|---|---|
| 56 | 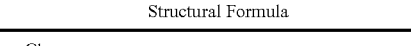 | $^1$H-NMR (400 MHz, CDCl3) δ: 1.73(2H, d, J = 12.4 Hz), 2.01(2H, d, J = 12.4 Hz), 2.10(2H, td, J = 3.2, 12.8 Hz), 2.21(2H, td, J = 3.2, 12.4 Hz), 2.64(1H, s), 3.82(3H, s), 3.95-4.03(4H, m), 6.40(1H, s), 6.84(2H, d, J = 8.4 Hz), 7.12(2H, d, J = 8.8 Hz), 7.23(2H, d, J = 8.8 Hz), 7.28(2H, d, J = 8.8 Hz). ESI-MS: m/z = 441 (M + H)$^+$ |

TABLE 5-6-continued

| Reference Example | Structural Formula | Compound Data |
|---|---|---|
| 57 | (structure) | $^1$H-NMR (400 MHz, CDCl3) δ: 1.70(2H, d, J = 12.0 Hz), 2.01(2H, d, J = 8.8 Hz), 2.10(2H, td, J = 4.0, 12.8 Hz), 2.21 (2H, td, J = 3.6, 12.4 Hz), 2.71(1H, s), 3.80(3H, s), 3.92-4.03(4H, m), 6.39(1H, s), 6.81(2H, d, J = 12.0 Hz), 7.13 (2H, d, J = 12.0 Hz), 7.22-7.35(5H, m). |
| 58 | (structure) | $^1$H-NMR (400 MHz, CDCl3) δ: 1.71-1.74(4H, m), 1.96-2.16(4H, m), 2.87(1H, s), 3.81(3H, s), 3.94-4.01(4H, m), 6.52(1H, s), 6.86(2H, d, J = 8.0 Hz), 7.19(2H, d, J = 8.0 Hz), 7.32(2H, d, J = 8.0 Hz), 7.54(2H, d, J = 8.0 Hz). |
| 59 | (structure) | $^1$H-NMR (400 MHz, CDCl3) δ: 1.23(3H, t, J = 7.6 Hz), 1.69-1.76(2H, m), 1.98-2.26(6H, m), 2.63(2H, q, J = 7.6 Hz), 2.69(1H, br), 3.81(3H, s), 3.95-4.03(4H, m), 6.40 (1H, s), 6.82-6.87(2H, m), 7.12(4H, s), 7.19-7.24(2H, m). ESI-MS: m/z = 425 (M + H)$^+$ |

TABLE 5-7

| Reference Example | Structural Formula | Compound Data |
|---|---|---|
| 60 | (structure) | $^1$H-NMR (400 MHz, CDCl$_3$) δ: 1.68-1.77(2H, m), 1.97-2.25(6H, m), 2.35(3H, s), 2.64(1H, s), 3.89(3H, s), 3.94-4.03(4H, m), 6.40(1H, s), 6.87(1H, t, J = 8.8 Hz), 6.94-7.01(1H, m), 7.07-7.13(5H, m). ESI-MS: m/z = 425 (M + H)$^+$ |
| 61 | (structure) | $^1$H-NMR (400 MHz, CDCl$_3$) δ: 1.69-1.77(2H, m), 1.97-2.28(9H, m), 2.64(1H, s), 3.82(3H, s), 3.95-4.03(4H, m), 6.41(1H, s), 6.83-6.89(4H, m), 7.08(1H, t, J = 8.0 Hz), 7.18-7.27(2H, m). ESI-MS: m/z = 439 (M + H)$^+$ |

TABLE 5-7-continued

| Reference Example | Structural Formula | Compound Data |
|---|---|---|
| 62 | 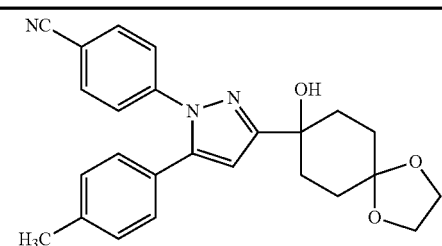 | $^1$H_NMR (400 MHz, CDCl$_3$) δ: 1.70-1.78(2H, m), 1.97-2.27(6H, m), 2.38(3H, s), 2.54(1H, s), 3.94-4.03(4H, m), 6.45(1H, s), 7.09-7.20(4H, m), 7.40-7.44(2H, m), 7.57-7.62(2H, m).<br>ESI-MS: m/z = 416 (M + H)$^+$ |
| 63 | 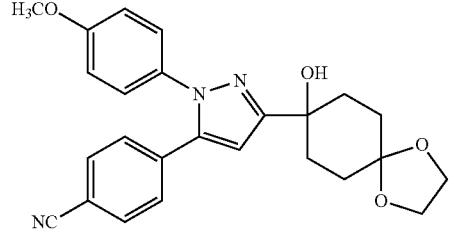 | $^1$H-NMR (400 MHz, CDCl$_3$) δ: 1.69-1.76(2H, m), 1.97-2.26(6H, m), 2.56(1H, br), 3.83(3H, s), 3.94-4.03(4H, m), 6.52(1H, s), 6.84-6.90(2H, m), 7.14-7.20(2H, m), 7.29-7.33(2H, m), 7.55-7.59(2H, m).<br>ESI-MS: m/z = 432 (M + H)$^+$ |

The following compounds were prepared in the same manner as in Examples 37-41 described below.

TABLE 6-1

| Reference Example | Structural Formula | Compound Data |
|---|---|---|
| 64 | 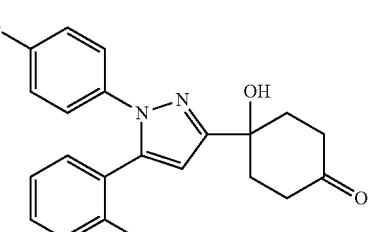 | $^1$H-NMR (400 MHz, CDCl$_3$) δ: 1.99 (3H, s), 2.34-2.39 (5H, m), 2.42-2.43 (1H, m), 2.87-2.96 (2H, m), 3.19 (1H, s), 3.76 (3H, s), 6.31 (1H, s), 6.76 (2H, d, J = 8.8 Hz), 7.11-7.20 (5H, m), 7.25-7.28 (1H, m).<br>ESI-MS: m/z = 377 (M + H)$^+$ |
| 65 | 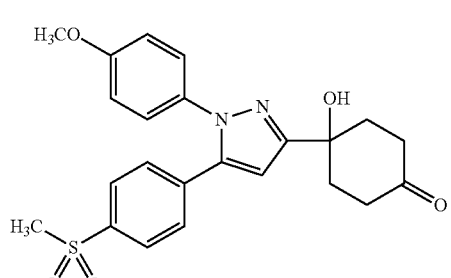 | $^1$H-NMR (400 MHz, CDCl$_3$) δ: 2.34-2.44 (6H, m), 2.86-2.96 (3H, m), 3.07 (3H, s), 3.83 (3H, s), 6.54 (1H, S), 6.90 (2H, d, J = 8.8 Hz), 7.19 (2H, d, J = 8.8 Hz), 7.41 (2H, d, J = 8.8 Hz), 7.87 (2H, d, J = 8.8 Hz).<br>ESI-MS: m/z = 441 (M + H)$^+$ |
| 66 | 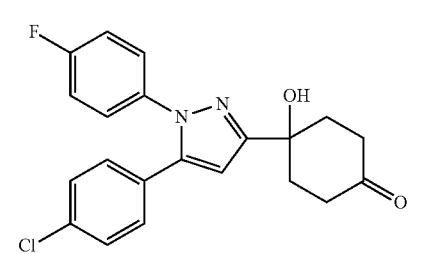 | $^1$H-NMR (400 MHz, CDCl$_3$) δ: 2.31-2.45 (6H, m), 2.82 (1H, s), 2.86-2.97 (2H, m), 6.45 (1H, s), 7.03-7.10 (2H, m), 7.12-7.17 (2H, m), 7.22-7.33 (4H, m).<br>ESI-MS: m/z = 385 (M + H)$^+$ |

TABLE 6-1-continued

| Reference Example | Structural Formula | Compound Data |
|---|---|---|
| 67 | 2,4-dichlorophenyl-N(1), 4-chlorophenyl-C(5) pyrazole with 4-hydroxy-4-cyclohexanone at C(3) | $^1$H-NMR (400 MHz, CDCl$_3$) δ: 2.32-2.45 (6H, m), 2.75 (1H, s), 2.84-2.94 (2H, m), 6.50 (1H, s), 7.09-7.12 (2H, m), 7.25-7.28 (2H, m), 7.34-7.36 (2H, m), 7.46-7.48 (1H, m). ESI-MS: m/z = 435 (M + H)$^+$ |
| 68 | 4-methoxyphenyl-N(1), 3-methylphenyl-C(5) pyrazole with 4-hydroxy-4-cyclohexanone at C(3) | $^1$H-NMR (400 MHz, CDCl$_3$) δ: 2.29-2.44 (9H, m), 2.86-2.96 (2H, m), 3.00 (1H, s), 3.81 (3H, s), 6.41 (1H, s), 6.86 (2H, d, J = 9.2 Hz), 6.93-6.97 (1H, m), 7.09-7.19 (m, 3H), 7.21 (2H, d, J = 9.2 Hz). ESI-MS: m/z = 377 (M + H)$^+$ |

TABLE 6-2

| Reference Example | Structural Formula | Compound Data |
|---|---|---|
| 69 | 4-fluorophenyl-N(1), 4-methylphenyl-C(5) pyrazole with 4-hydroxy-4-cyclohexanone at C(3) | $^1$H-NMR (400 MHz, CDCl$_3$) δ: 2.32-2.36 (4H, m), 2.35 (3H, s), 2.38-2.44 (2H, m), 2.87-2.96 (2H, m), 2.90 (1H, s), 6.41 (1H, s), 7.01 (2H, m), 7.09 (2H, d, J = 8.4 Hz), 7.13 (2H, d, J = 8.4 Hz), 7.23-7.30 (2H, m). ESI-MS: m/z = 365 (M + H)$^+$ |
| 70 | 4-methoxyphenyl-N(1), 4-fluorophenyl-C(5) pyrazole with 4-hydroxy-4-cyclohexanone at C(3) | $^1$H-NMR (400 MHz, CDCl$_3$) δ: 2.32-2.37 (4H, m), 2.37-2.45 (2H, m), 2.87-2.96 (2H, m), 2.94 (1H, s), 3.82 (3H, s), 6.40 (1H, s), 6.85-6.89 (2H, m), 6.97-7.03 (2H, m), 7.17-7.21 (4H, m). ESI-MS: m/z = 381 (M + H)$^+$ |
| 71 | 4-chlorophenyl-N(1), 4-fluorophenyl-C(5) pyrazole with 4-hydroxy-4-cyclohexanone at C(3) | $^1$H-NMR (400 MHz, CDCl$_3$) δ: 2.31-2.36 (4H, m), 2.38-2.45 (2H, m), 2.85 (1H, s), 2.87-2.96 (2H, m), 6.43 (1H, s), 7.01-7.07 (2H, m), 7.18-7.23 (4H, m), 7.31-7.34 (2H, m). ESI-MS: m/z = 385 (M + H)$^+$ |

TABLE 6-2-continued

| Reference Example | Structural Formula | Compound Data |
|---|---|---|
| 72 | (4-F-C6H4)-pyrazole-(4-F-C6H4), 4-hydroxy-4-cyclohexanone | $^1$H-NMR (400 MHz, CDCl$_3$) δ: 2.32-2.36 (4H, m), 2.39-2.45 (2H, m), 2.87 (1H, s), 2.87-2.96 (2H, m), 6.42 (1H, s), 7.00-7.08 (4H, m), 7.16-7.21 (2H, m), 7.23-7.28 (2H, m). ESI-MS: m/z = 369 (M + H)$^+$ |
| 73 | (4-F-C6H4)-pyrazole-(4-F-C6H4)-Ph, 4-hydroxy-4-cyclohexanone | $^1$H-NMR (400 MHz, CDCl$_3$) δ: 2.33-2.37 (4H, m), 2.38-2.45 (2H, m), 2.87-2.96 (2H, m), 2.94 (1H, s), 6.43 (1H, s), 6.98-7.03 (2H, m), 7.17-7.22 (2H, m), 7.26-7.39 (5H, m). ESI-MS: m/z = 351 (M + H)$^+$ |
| 74 | (4-CH3-C6H4)-pyrazole-(4-F-C6H4), 4-hydroxy-4-cyclohexanone | $^1$H-NMR (400 MHz, CDCl$_3$) δ: 2.32-2.37 (4H, m), 2.37 (3H, s), 2.38-2.44 (2H, m), 2.87-2.95 (2H, m), 2.94 (1H, s), 6.40 (1H, s), 6.97-7.03 (2H, m), 7.13-7.22 (6H, m). ESI-MS: m/z = 365 (M + H)$^+$ |

TABLE 6-3

| Reference Example | Structural Formula | Compound Data |
|---|---|---|
| 75 | (4-CH3SO2-C6H4)-pyrazole-(4-CH3-C6H4), 4-hydroxy-4-cyclohexanone | $^1$H-NMR (400 MHz, CDCl$_3$) δ: 2.32-2.36 (4H, m), 2.39 (3H, s), 2.39-2.46 (2H, m), 2.85 (1H, s), 2.88-2.96 (2H, m), 3.07 (3H, s), 6.46 (1H, s), 7.12 (2H, d, J = 8.0 Hz), 7.18 (2H, d, J = 8.0 Hz), 7.51 (2H, d, J = 8.4 Hz), 7.90 (2H, d, J = 8.4 Hz). ESI-MS: m/z = 425 (M + H)$^+$ |
| 76 | (4-CH3O-C6H4)-pyrazole-(2-OCH3-pyridin-3-yl), 4-hydroxy-4-cyclohexanone | $^1$H-NMR (400 MHz, CDCl$_3$) δ: 2.32-2.43 (6H, m), 2.88-2.95 (3H, m), 3.68 (3H, s), 3.80 (3H, s), 6.47 (1H, s), 6.84 (2H, d, J = 8.8 Hz), 6.87-6.89 (1H, m), 7.17 (2H, d, J = 8.8 Hz), 7.45-7.47 (1H, m), 8.15-8.17 (1H, m),. ESI-MS: m/z = 394 (M + H)$^+$ |

TABLE 6-3-continued

| Reference Example | Structural Formula | Compound Data |
|---|---|---|
| 77 | 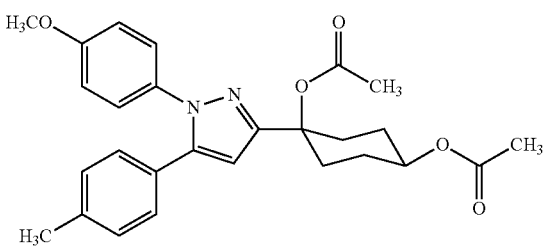 | $^1$H-NMR (400 MHz, CDCl$_3$) δ: 2.31-2.43 (6H, m), 2.86-2.93 (2H, m), 2.95 (1H, s), 3.81 (3H, s), 6.38 (1H, s), 6.84 (2H, d, J = 8.8 Hz), 7.04 (2H, t, J = 8.8 Hz), 7.12 (2H, d, J = 8.80 Hz), 7.24-7.30 (2H, m). ESI-MS: m/z = 381 (M + H)$^+$ |

Reference Example 78

1-(1-(4-Methoxyphenyl)-5-(p-tolyl)-1H-pyrazol-3-yl)-cyclohexane-cis-1,4-diyl diacetate

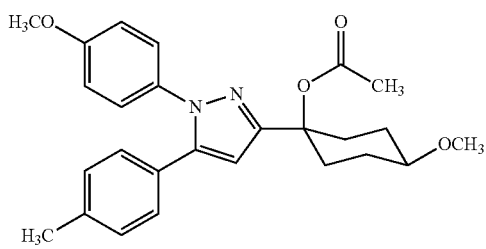

To a suspension of 1-(1-(4-methoxyphenyl)-5-(p-tolyl)-1H-pyrazol-3-yl)cyclohexane-cis-1,4-diol (Example 2-B) (300 mg, 0.793 mmol) in dichloromethane (2.6 mL), acetic anhydride (0.187 mL, 1.98 mmol), pyridine (0.192 mL, 2.38 mmol) and 4-dimethylaminopyridine (48.4 mg, 0.396 mmol) were added, and the obtained solution was stirred at room temperature for 60 hours. Again, 4-dimethylaminopyridine (48.4 mg, 0.396 mmol) was added and the resulting solution was stirred at room temperature for an additional 6 hours. The reaction was quenched by adding water to the reaction solution, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (297 mg, 0.642 mmol, 81%) as a white solid.

$^1$H-NMR (400 MHz, CDCl$_3$) δ: 1.74-1.82 (2H, m), 1.92-1.98 (2H, m), 2.01-2.08 (5H, m), 2.10 (3H, s), 2.32 (3H, s), 2.70-2.77 (2H, m), 3.80 (3H, s), 4.80-4.89 (1H, m), 6.38 (1H, s), 6.83 (2H, d, J=8.8 Hz), 7.08 (4H, s), 7.20 (2H, d, J=8.8 Hz).
ESI-MS: m/z=463 (M+H)$^+$

Reference Example 79 c-4-Methoxy-1-(1-(4-methoxyphenyl)-5-(p-tolyl)-1H-pyrazol-3-yl)-cyclohexan-r-1-yl acetate

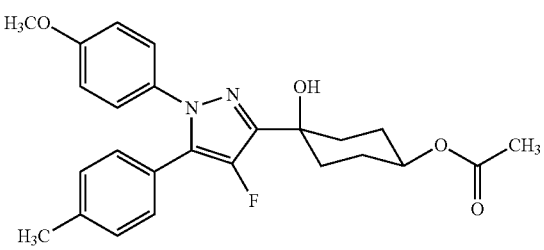

To a solution of c-4-hydroxy-1-(1-(4-methoxyphenyl)-5-(p-tolyl)-1H-pyrazol-3-yl)-cyclohexan-r-1-yl acetate (Comparative Example 26) (0.150 g, 0.357 mmol) in N,N-dimethylformamide (1.8 mL), 55% sodium hydride (23.4 mg, 0.535 mmol) and methyl iodide (29.0 μL, 0.464 mmol) were added with stirring under ice-cooling, and the obtained solution was stirred at room temperature for 9 hours. The reaction was quenched by adding water to the reaction solution with stirring under ice-cooling, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (124 mg, 0.284 mmol, 80%) as a white solid.

$^1$H-NMR (400 MHz, CDCl$_3$) δ: 1.60-1.68 (2H, m), 1.94-2.03 (4H, m), 2.08 (3H, s), 2.32 (3H, s), 2.69-2.76 (2H, m), 3.24-3.33 (1H, m), 3.39 (3H, s), 3.80 (3H, s), 6.37 (1H, s), 6.83 (2H, d, J=8.8 Hz), 7.08 (4H, s), 7.20 (2H, d, J=8.8 Hz).
ESI-MS: m/z=435 (M+H)$^+$

Reference Example 80

4-(4-Fluoro-1-(4-methoxyphenyl)-5-(p-tolyl)-1H-pyrazol-3-yl)-c-4-hydroxy-cyclohexan-r-1-yl acetate To a solution of c-4-hydroxy-4-(1-(4-methoxyphenyl)-5-(p-tolyl)-1H-pyrazol-3-yl)-cyclohexane-r-1-yl acetate (Example 57) (130 mg, 0.309 mmol) in acetonitrile (3.09 mL), Selectfluor™ (120 mg, 0.340 mmol) was added, and the obtained solution was stirred at room temperature for 3 hours. Saturated aqueous sodium thiosulfate solution was added to the reaction solution, and the resulting solution was extracted with ethyl acetate. The organic layer was washed with brine, dried over anhydrous magnesium sulfate and concentrated under reduced pressure. The residue was purified by flash chromatography (silica gel, n-hexane/ethyl acetate) to obtain the captioned compound (61 mg, 0.140 mmol, 45%) as a light yellow amorphous product.

$^1$H-NMR (400 MHz, CDCl$_3$) δ: 1.89-2.15 (11H, m), 2.35 (3H, m), 2.73 (1H, s), 3.81 (3H, s), 4.82-4.89 (1H, m), 6.84-6.86 (2H, m), 7.10-7.18 (6H, m).
ESI-MS: m/z=439 (M+H)$^+$

Reference Example 81

1-(1-(4-Methoxyphenyl)-5-(p-tolyl)-1H-pyrazol-3-yl)-4-oxo-cyclohexan-1-yl acetate

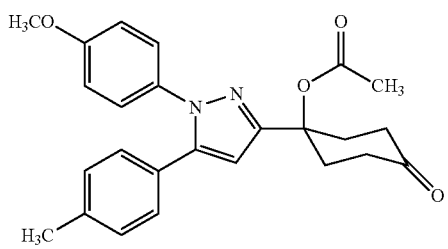

To a solution of c-4-hydroxy-1-(1-(4-methoxyphenyl)-5-(p-tolyl)-1H-pyrazol-3-yl)-cyclohexan-r-1-yl acetate (Comparative Example 26) (142 mg, 0.338 mmol) in dichloromethane (3.38 mL), Dess-Martin reagent (172 mg, 0.405 mmol) was added, and the obtained solution was stirred at 0° C. for 2 hours. The reaction solution was filtered through Celite and the residue was purified by flash chromatography (silica gel, n-hexane/ethyl acetate) to obtain the captioned compound (120 mg, 0.287 mmol, 85%) as a white amorphous product.

$^1$H-NMR (400 MHz, CDCl$_3$) δ: 2.13 (3H, s), 2.33 (3H, s), 2.44-2.52 (4H, m), 2.59-2.65 (2H, m), 2.93-2.96 (2H, m), 3.81 (3H, s), 6.45 (1H, s), 6.84 (2H, d, J=8.8 Hz), 7.08 (4H, s), 7.20 (2H, d, J=8.8 Hz).
ESI-MS: m/z=419 (M+H)$^+$

Reference Example 82 c-4-Hydroxy-4-(1-(4-methoxyphenyl)-5-(p-tolyl)-1H-pyrazol-3-yl)-cis-cyclohexane-r-1-carbaldehyde

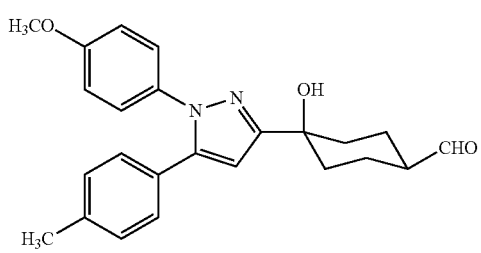

To a solution of (methoxymethyl)triphenylphosphonium chloride (546.3 mg, 1.59 mmol) in tetrahydrofuran (1.3 mL), potassium tert-butoxide (178.7 mg, 1.59 mmol) was added at −40° C., and the obtained solution was stirred at the same temperature for 60 minutes. To the reaction solution, a solution of 4-hydroxy-4-(1-(4-methoxyphenyl)-5-(p-tolyl)-1H-pyrazol-3-yl)cyclohexan-1-one (Example 37) (200 mg, 0.53 mmol) in tetrahydrofuran (1.35 mL) was added dropwise at −40° C., and the obtained solution was stirred at room temperature for 1.5 hours. To the reaction solution, 6 M aqueous hydrochloric acid solution was added at 0° C., and the obtained solution was stirred for 12 hours. Distilled water was added to the reaction solution and the resulting solution was extracted with ethyl acetate. The organic layer was washed with saturated aqueous sodium hydrogen carbonate solution and brine, dried over anhydrous sodium sulfate and concentrated under reduced pressure. The residue was purified by flash chromatography (silica gel, n-hexane/ethyl acetate) to obtain the captioned compound (87.5 mg, 0.23 mmol, 42%) as a colorless oily product.

$^1$H-NMR (400 MHz, CDCl$_3$) δ: 1.88-1.96 (6H, m), 2.09-2.11 (2H, m), 2.25-2.36 (5H, m), 3.80 (3H, s), 6.39 (1H, s), 6.84 (2H, d, J=8.8 Hz), 7.09-7.14 (4H, m), 7.20 (2H, d, J=8.8 Hz), 9.66 (1H, d, J=2.0 Hz).
ESI-MS: m/z=391 (M+H)$^+$

Reference Example 83

Ethyl 1,4-dioxaspiro[4.5]decane-8-carboxylate

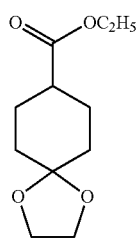

To a solution of ethyl 4-oxocyclohexanecarboxylate (10.0 g, 58.8 mmol) in toluene (196 mL), ethylene glycol (3.6 mL, 64.6 mmol) and p-toluenesulfonic acid monohydrate (1.12 g, 5.88 mmol) were added, and the obtained solution was heated to reflux at 150° C. The resulting solution was stirred for 18 hours. The reaction was quenched by adding a saturated sodium bicarbonate solution to the reaction solution, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (12.3 g, 57.4 mmol, 98%) as a colorless oily compound.

$^1$H-NMR (400 MHz, CDCl$_3$) δ: 1.25 (3H, t, J=7.2 Hz), 1.51-1.61 (2H, m), 1.75-1.86 (4H, m), 1.90-1.98 (2H, m), 2.29-2.38 (1H, s), 3.95 (4H, s), 4.13 (2H, q, J=7.2 Hz).
ESI-MS: m/z=215 (M+H)$^+$

Reference Example 84

Ethyl 8-(benzyloxymethyl)-1,4-dioxaspiro[4.5]decane-8-carboxylate

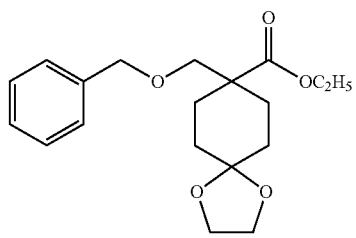

To a solution of ethyl 1,4-dioxaspiro[4.5]decane-8-carboxylate (Reference Example 83) (500 mg, 2.33 mmol) in tetrahydrofuran (7.8 mL), 0.5 M potassium bis(trimethylsilyl)amide (solution in toluene, 4.67 mL, 2.33 mmol) was added at −78° C., and the obtained solution was stirred for 20 minutes. Thereafter, benzylchloromethylether (0.379 mL, 2.45 mmol) was added, and the obtained solution was stirred at −78° C. for 30 minutes and at room temperature for 1.5 hours. Saturated aqueous ammonium chloride solution was added to the reaction solution, and the resulting solution was extracted with ethyl acetate. The organic layer was dried over anhydrous sodium sulfate and concentrated under reduced pressure. To the residue, 3 M aqueous sodium hydroxide solution (1.0 mL) was added, and the obtained solution was stirred for 4 hours. The reaction solution was extracted with ether and the organic layer was washed with brine, dried over anhydrous sodium sulfate and concentrated under reduced pressure. The residue was purified by flash chromatography (silica gel, n-hexane/ethyl acetate) to obtain the captioned compound (279 mg, 0.834 mmol, 36%) as a colorless oily compound.

$^1$H-NMR (400 MHz, CDCl$_3$) δ: 1.24 (3H, t, J=7.2 Hz), 1.52-1.68 (6H, m), 2.16-2.23 (2H, m), 3.46 (2H, s), 3.88-3.96 (4H, m), 4.17 (2H, q, J=7.2 Hz), 4.49 (2H, s), 7.25-7.39 (5H, m).

ESI-MS: m/z=335 (M+H)$^+$

Reference Example 85

(8-(Benzyloxymethyl)-1,4-dioxaspiro[4.5]decan-8-yl)methanol

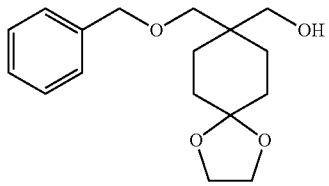

To a solution of ethyl 8-(benzyloxymethyl)-1,4-dioxaspiro[4.5]decane-8-carboxylate (Reference Example 84) (279 mg, 0.834 mmol) in tetrahydrofuran (4.2 mL), lithium borohydride (91.0 mg, 4.17 mmol) was added with stirring under ice-cooling, and the obtained solution was stirred at 70° C. for 4 hours. The reaction was quenched by adding saturated aqueous ammonium chloride solution to the reaction solution, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (183 mg, 0.625 mmol, 75%) as a colorless oily compound.

$^1$H-NMR (400 MHz, CDCl$_3$) δ: 1.48-1.66 (8H, m), 2.76 (1H, t, J=6.0 Hz), 3.43 (2H, s), 3.60 (2H, d, J=6.0 Hz), 3.91-3.95 (4H, m), 4.52 (2H, s), 7.27-7.38 (5H, m).

ESI-MS: m/z=293 (M+H)$^+$

Reference Example 86

8-(Benzyloxymethyl)-1,4-dioxaspiro[4.5]decane-8-carbaldehyde

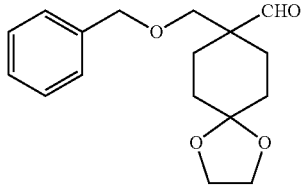

To a solution of (8-(benzyloxymethyl)-1,4-dioxaspiro[4.5]decan-8-yl)methanol (Reference Example 85) (183 mg, 0.625 mmol) in dimethyl sulfoxide (2.1 mL), 50% sulfur trioxide-pyridine complex (596 mg, 1.87 mmol) and triethylamine (0.522 mL, 3.75 mmol) were added, and the obtained solution was stirred at room temperature for 20 minutes. The reaction was quenched by adding water to the reaction solution, and the resulting solution was extracted with ethyl acetate. The organic layer was washed sequentially with 20% aqueous citric acid solution, saturated sodium bicarbonate solution and brine, dried over anhydrous sodium sulfate and concentrated under reduced pressure. The residue was purified by flash chromatography (silica gel, n-hexane/ethyl acetate) to obtain the captioned compound (172 mg, 0.592 mmol, 95%) as a colorless oily compound.

$^1$H-NMR (400 MHz, CDCl$_3$) δ: 1.55-1.67 (6H, m), 2.03-2.11 (2H, m), 3.45 (2H, s), 3.90-3.95 (4H, m), 4.47 (2H, s), 7.25-7.36 (5H, m), 9.60 (1H, s).

ESI-MS: m/z=291 (M+H)$^+$

Reference Example 87

8-(Benzyloxymethyl)-8-ethynyl-1,4-dioxaspiro[4.5]decane

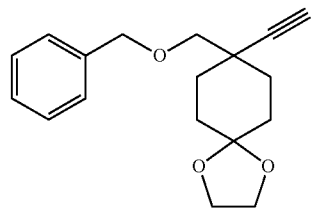

To a solution of 8-(benzyloxymethyl)-1,4-dioxaspiro[4.5]decane-8-carbaldehyde (Reference Example 86) (100 mg, 0.344 mmol) in methanol (5.2 mL), potassium carbonate (143 mg, 1.03 mmol) and dimethyl-1-diazo-2-oxopropylphosphonate (165 mg, 0.861 mmol) were added with stirring under ice-cooling, and the obtained solution was stirred at room temperature for 1 hour. The reaction was quenched by adding water to the reaction solution, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (88.9 mg, 0.310 mmol, 90%) as a colorless oily compound.

$^1$H-NMR (400 MHz, CDCl$_3$) δ: 1.52-1.71 (4H, m), 1.77-1.85 (2H, m), 1.94-2.04 (2H, m), 2.19 (1H, s), 3.38 (2H, s), 3.89-3.99 (4H, s), 4.61 (2H, s), 7.25-7.37 (5H, m).

ESI-MS: m/z=287 (M+H)$^+$

Reference Example 88

3-(8-(Benzyloxymethyl)-1,4-dioxaspiro[4.5]decan-8-yl)-1-(p-tolyl)propyn-1-ol

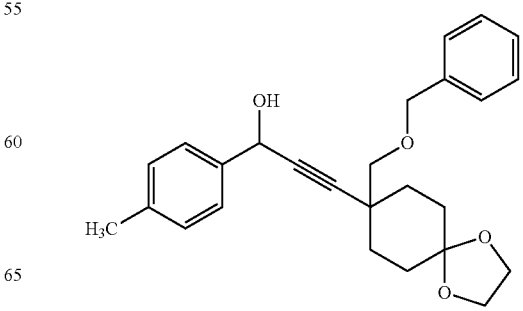

To a solution of 8-(benzyloxymethyl)-8-ethynyl-1,4-dioxaspiro[4.5]decane (Reference Example 87) (393 mg, 1.37 mmol) in tetrahydrofuran (4.6 mL), 2.6 M n-butyllithium (solution in hexane, 0.555 mL, 1.44 mmol) was added at −78° C., and the obtained solution was stirred for 10 minutes. Further, 4-methylbenzaldehyde (0.178 mL, 1.51 mmol) was added, and the obtained solution was allowed to warm gradually to room temperature and stirred for 1 hour. Saturated aqueous ammonium chloride solution was added to the reaction solution, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (459 mg, 1.13 mmol, 82%) as a colorless oily compound.

$^1$H-NMR (400 MHz, CDCl$_3$) δ: 1.62-1.71 (4H, m), 1.79-1.86 (2H, m), 1.92-2.02 (2H, m), 2.23 (1H, brs), 2.34 (3H, s), 3.41 (2H, s), 3.89-3.98 (4H, m), 4.59 (2H, m), 5.44 (1H, d, J=5.2 Hz), 7.15 (2H, d, J=8.0 Hz), 7.25-7.35 (5H, m), 7.43 (2H, d, J=8.0 Hz).

ESI-MS: m/z=407 (M+H)$^+$

Reference Example 89

3-(8-(Benzyloxymethyl)-1,4-dioxaspiro[4.5]decan-8-yl)-1-(p-tolyl)propyn-1-one

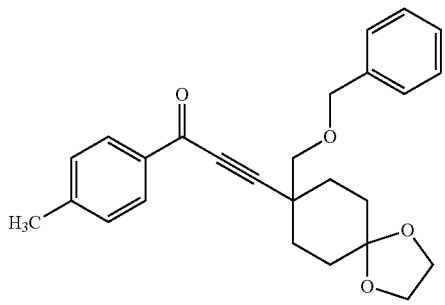

To a solution of 3-(8-(benzyloxymethyl)-1,4-dioxaspiro[4.5]decan-8-yl)-1-(p-tolyl)propyn-1-ol (Reference Example 88) (585 mg, 1.44 mmol) in dichloromethane (7.2 mL), manganese dioxide (625 mg, 7.19 mmol) was added, and the obtained solution was stirred at room temperature for 13 hours. The reaction solution was filtered through Celite and the filtrate was concentrated under reduced pressure. The residue was purified by flash chromatography (silica gel, n-hexane/ethyl acetate) to obtain the captioned compound (540 mg, 1.33 mmol, 93%) as a colorless oily compound.

$^1$H-NMR (400 MHz, CDCl$_3$) δ: 1.71-1.80 (4H, m), 1.97-2.03 (4H, m), 2.41 (3H, s), 3.52 (2H, s), 3.91-4.00 (4H, m), 4.63 (2H, m), 7.21 (2H, d, J=8.0 Hz), 7.25-7.38 (5H, m), 8.03 (2H, d, J=8.0 Hz).

ESI-MS: m/z=405 (M+H)$^+$

Reference Example 90

3-(8-(Benzyloxymethyl)-1,4-dioxaspiro[4.5]decan-8-yl)-1-(4-methoxyphenyl)-5-(p-tolyl)-1H-pyrazole

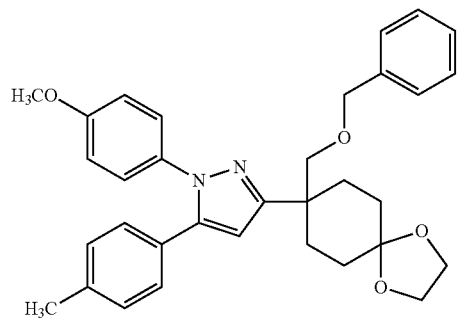

To a solution of 4-methoxyphenylhydrazine hydrochloride (280 mg, 1.60 mmol) in ethanol (2.7 mL), triethylamine (0.447 mL, 3.20 mmol) was added dropwise, and the obtained solution was stirred at room temperature for 30 minutes. To the reaction solution, a solution of 3-(8-(benzyloxymethyl)-1,4-dioxaspiro[4.5]decan-8-yl)-1-(p-tolyl)propyn-1-one (Reference Example 89) (540 mg, 1.33 mmol) in ethanol (2.7 mL) was added dropwise, and the obtained solution was stirred at room temperature for 14 hours. Thereafter, the reaction solution was concentrated under reduced pressure. Water was added to the residue and the resultant was extracted with ethyl acetate. The organic layer was washed with 1 M hydrochloric acid, distilled water and brine, dried over anhydrous magnesium sulfate and concentrated under reduced pressure. The residue was purified by flash chromatography (silica gel, n-hexane/ethyl acetate) to obtain the captioned compound (458 mg, 0.872 mmol, 65%) as a white amorphous product.

$^1$H-NMR (400 MHz, CDCl$_3$) δ: 1.64-1.72 (2H, m), 1.76-1.85 (2H, m), 1.89-1.98 (2H, m), 2.27-2.35 (5H, m), 3.50 (2H, s), 3.80 (3H, s), 3.90-3.99 (4H, m), 4.49 (2H, s), 6.38 (1H, s), 6.80-6.85 (2H, m), 7.06-7.31 (11H, m).

ESI-MS: m/z=525 (M+H)$^+$

Reference Example 91

4-(Benzyloxymethyl)-4-(1-(4-methoxyphenyl)-5-(p-tolyl)-1H-pyrazol-3-yl)cyclohexan-1-one

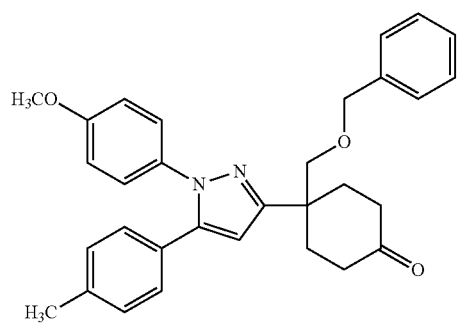

To a solution of 3-(8-(benzyloxymethyl)-1,4-dioxaspiro[4.5]decan-8-yl)-1-(4-methoxyphenyl)-5-(p-tolyl)-1H-pyrazole (Reference Example 90) (458 mg, 0.872 mmol) in tetrahydrofuran (2.2 mL), 6 M hydrochloric acid (4.4 mL) was added, and the obtained solution was stirred at room temperature for 15 hours. The reaction solution was cooled in ice and 50% aqueous sodium hydroxide solution was added dropwise thereto at 0° C. until basic. Thereafter, the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (387 mg, 0.804 mmol, 92%) as a white amorphous product.

$^1$H-NMR (400 MHz, CDCl$_3$) δ: 2.11-2.21 (2H, m), 2.31-2.39 (5H, m), 2.52-2.68 (4H, m), 3.57 (2H, s), 3.81 (3H, s), 4.51 (2H, s), 6.44 (1H, s), 6.83-6.88 (2H, m), 7.08-7.34 (11H, m).

ESI-MS: m/z=481 (M+H)$^+$

Reference Example 92

8-(4,5-Bis(4-methoxyphenyl)oxazol-2-yl)-1,4-dioxaspiro[4.5]decan-8-ol

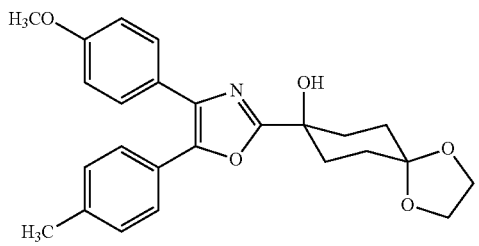

To a solution of 2-chloro-1,4-bis(4-methoxyphenyl)oxazole (1.01 g, 3.20 mmol), which was synthesized by the known production process (WO 2007/111323), in tetrahydrofuran (32 mL), 1.09 M borane-tetrahydrofuran complex (4.0 mL, 4.36 mmol) was added at 0° C., and the obtained solution was stirred at the same temperature for 1 hour. To the reaction solution, 2.66 M n-butyllithium (1.47 mL, mmol) was added at −78° C., and the obtained solution was stirred at the same temperature for 1 hour. To the reaction solution, 1,4-cyclohexanedione monoethylene ketal (524 mg, 3.36 mmol) was added, and the obtained solution was allowed to warm gradually to room temperature with stirring. To the reaction solution, 1 M hydrochloric acid was added to make the mixture acidic, and the resulting solution was extracted with ethyl acetate. The organic layer was dried over anhydrous magnesium sulfate and concentrated under reduced pressure. The residue was purified by flash chromatography (silica gel, n-hexane/ethyl acetate) to obtain the captioned compound (844 mg, 1.92 mmol, 60%) as a light yellow amorphous product.

$^1$H-NMR (400 MHz, CDCl$_3$) δ: 1.71-1.80 (2H, m), 2.01-2.11 (4H, m), 2.30-2.41 (2H, m), 2.76 (1H, s), 3.83 (3H, s), 3.84 (3H, s), 3.99 (4H, dd, J=Hz), 6.89 (2H, d, J=8.8 Hz), 6.90 (2H, d, J=8.8 Hz), 7.50 (2H, d, J=8.8 Hz), 7.56 (2H, d, J=8.8 Hz).

Reference Example 93

1,4-Dioxaspiro[4.5]decane-8-carboxamide

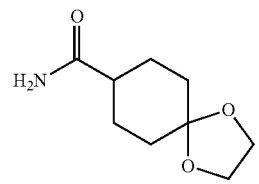

To a solution of 1,4-dioxaspiro[4.5]decane-8-carboxylic acid (823 mg, 4.42 mmol) in tetrahydrofuran (22 mL), triethylamine (5.87 mL, 42.1 mmol) and n-propyl chloroformate were added at 0° C., and the obtained solution was stirred at the same temperature for 1 hour. After adding dropwise, the obtained solution was stirred at room temperature for 30 minutes. To the reaction solution, 28% aqueous ammonia (1.5 mL) was added, and the obtained solution was stirred at room temperature for 1 hour. The organic layer was separated from the reaction solution, dried over sodium sulfate and concentrated under reduced pressure. The residue was purified by flash chromatography (silica gel, n-hexane/ethyl acetate) to obtain the captioned compound (694 mg, 3.75 mmol, 85%) as a colorless amorphous product.

$^1$H-NMR (400 MHz, CDCl$_3$) δ: 1.53-1.61 (2H, m), 1.72-1.86 (4H, m), 1.91-1.98 (2H, m), 2.17-2.25 (1H, m), 3.95 (4H, s), 5.29 (1H, brs), 5.46 (1H, brs).

ESI-MS: m/z=186 (M+H)$^+$

Reference Example 94

1,4-Dioxaspiro[4.5]decane-8-carbothioamide

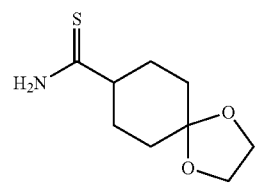

To a solution of 1,4-dioxaspiro[4.5]decane-8-carboxamide (Reference Example 93) (281 mg, 1.52 mmol) in toluene (5 mL), Lawson's reagent (337 mg, 0.834 mmol) was added, and the obtained solution was stirred at 100° C. for 1 hour before being cooled to room temperature. Methanol was added to the reaction solution, and the obtained solution was concentrated under reduced pressure. The residue was purified by flash chromatography (silica gel, n-hexane/ethyl acetate) to obtain the captioned compound (147 mg, 0.730 mmol, 48%) as a white solid.

$^1$H-NMR (400 MHz, CDCl$_3$) δ: 1.57-1.66 (2H, m), 1.79-1.90 (4H, m), 1.97-2.03 (2H, m), 2.64-2.72 (1H, m), 3.96 (4H, s), 6.89 (1H, brs), 7.46 (1H, brs).

ESI-MS: m/z=202 (M+H)$^+$

Reference Example 95

8-(4-(4-Methoxyphenyl)-5-(p-tolyl)thiazol-2-yl)-1,4-dioxaspiro[4.5]decane

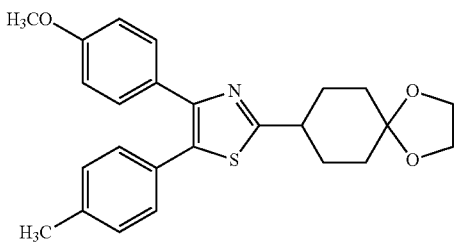

A solution of 1,4-dioxaspiro[4.5]decane-8-carbothioamide (Reference Example 94) (389 mg, 1.93 mmol) and 2-bromo-1-(4-methoxyphenyl)-2-(p-tolyl)ethanone (588 mg, 1.84 mmol) in acetonitrile (9.2 mL) was stirred at room temperature for 4 hours. Saturated aqueous sodium hydrogen carbonate solution was added to the reaction solution, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (630 mg, 1.49 mmol, 81%) as a colorless amorphous product.

$^1$H-NMR (400 MHz, CDCl$_3$) δ: 1.68-1.76 (2H, m), 1.88-1.98 (4H, m), 2.18-2.24 (2H, m), 2.35 (3H, s), 3.05-3.13 (1H, m), 3.80 (3H, s), 3.99 (4H, s), 6.79-6.82 (2H, m), 7.11 (2H, d, J=8.0 Hz), 7.22 (2H, d, J=8.0 Hz), 7.43-7.46 (2H, m).

ESI-MS: m/z=422 (M+H)$^+$

Reference Example 96

8-(4-(4-Methoxyphenyl)-5-(p-tolyl)thiazol-2-yl)-1,4-dioxaspiro[4.5]decan-8-ol

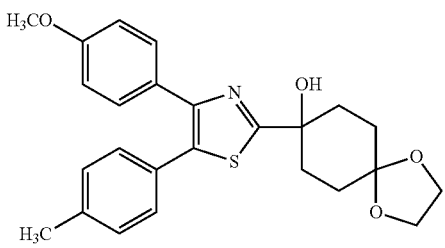

To a solution of 8-(4-(4-methoxyphenyl)-5-(p-tolyl)thiazol-2-yl)-1,4-dioxaspiro[4.5]decane (Reference Example 95) (734 mg, 1.74 mmol) in tetrahydrofuran (8.7 mL), 1.63 M n-butyllithium/solution in n-hexane (1.17 mL) was added at −78° C., and the obtained solution was stirred at the same temperature for 1 hour. The reaction solution was added at −78° C. to a solution of 3-phenyl-2-(phenylsulfonyl)-1,2-oxaziridine (546 mg, 2.09 mmol) in tetrahydrofuran (8.7 mL), and the obtained solution was allowed to warm gradually to room temperature with stirring. Distilled water was added to the reaction solution, and the resulting solution was extracted with ethyl acetate. The organic layer was washed with brine, dried over sodium sulfate and concentrated under reduced pressure. The residue was purified by flash chromatography (silica gel, n-hexane/ethyl acetate) to obtain the captioned compound (417 mg, 0.954 mmol, 55%) as a colorless amorphous product.

$^1$H-NMR (400 MHz, CDCl$_3$) δ: 1.73-1.79 (2H, m), 2.03-2.10 (4H, m), 2.32-2.39 (2H, m), 2.37 (3H, s), 2.78 (1H, s), 3.84 (3H, s), 3.97-4.02 (4H, m), 6.88-6.92 (2H, m), 7.16 (2H, d, J=8.4 Hz), 7.47 (2H, d, J=8.4 Hz), 7.55-7.58 (2H, m).

ESI-MS: m/z=438 (M+H)$^+$

Reference Example 97

4-Hydroxy-4-(1-(4-methoxyphenyl)-5-(p-tolyl)-1H-pyrazol-3-yl)-cis-cyclohexyl 2-benzyloxycarbonylamino acetate

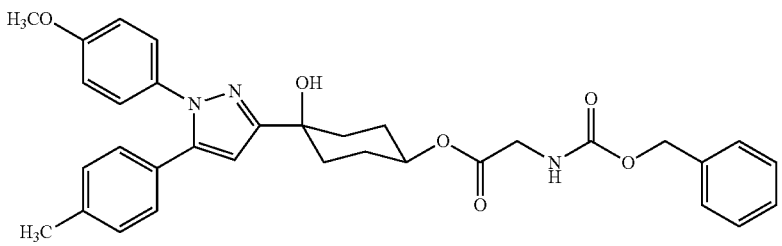

To a solution of 1-(1-(4-methoxyphenyl)-5-(p-tolyl)-1H-pyrazol-3-yl)-cyclohexane-cis-1,4-diol (Example 2-B) (76.0 mg, 0.201 mmol) in dichloromethane (2.00 mL), triethylamine (0.084 mL, 0.60 mmol), 2-benzyloxycarbonylamino acetic acid (46.2 mg, 0.241 mmol), 1-ethyl-3-(3-dimethylaminopropyl) carbodiimide hydrochloride (46.2 mg, 0.241 mmol) and 1-hydroxybenzotriazole (15.4 mg, 0.100 mmol) were added at room temperature, and the resulting solution was stirred for 20 hours. Distilled water was added to the reaction solution, and the resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (33.2 mg, 0.058 mmol, 29%) as a colorless amorphous product.

$^1$H-NMR (400 MHz, CDCl$_3$) δ: 1.91-2.07 (8H, m), 2.33 (3H, s), 2.75 (1H, s), 3.80 (3H, s), 3.98-3.99 (2H, m), 4.89-4.94 (1H, m), 5.14 (2H, s), 5.33-5.35 (1H, m), 6.36 (1H, s), 6.82-6.86 (2H, m), 7.08-7.10 (4H, m), 7.17-7.21 (2H, m), 7.29-7.38 (5H, m).

ESI-MS: m/z=552 (M−OH)$^+$

Reference Example 98

(S)-4-Hydroxy-4-(1-(4-methoxyphenyl)-5-(p-tolyl)-1H-pyrazol-3-yl)-cis-cyclohexyl 2-(benzyloxycarbonylamino)-3-methylbutanoate was synthesized in the same manner as in Reference Example 97.

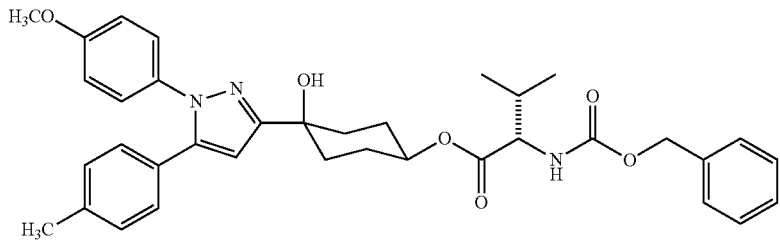

$^1$H-NMR (400 MHz, CDCl$_3$) δ: 0.92 (3H, d, J=6.4 Hz), 0.99 (3H, d, J=6.4 Hz), 1.89-2.10 (8H, m), 2.16-2.24 (1H, m), 2.34 (3H, s), 2.63 (1H, s), 3.81 (3H, s), 4.30-4.33 (1H, m), 4.88-4.95 (1H, m), 5.12 (2H, s), 5.28-5.30 (1H, m), 6.36 (1H, s), 6.78-6.82 (2H, m), 7.09-7.10 (4H, m), 7.18-7.24 (2H, m), 7.29-7.38 (5H, m).

ESI-MS: m/z=594 (M−OH)$^+$

Reference Example 99

(S)-4-Hydroxy-4-(1-(4-methoxyphenyl)-5-(p-tolyl)-1H-pyrazol-3-yl)cyclohexyloxy)methyl 2-(benzyloxycarbonylamino)-3-methylbutanoate

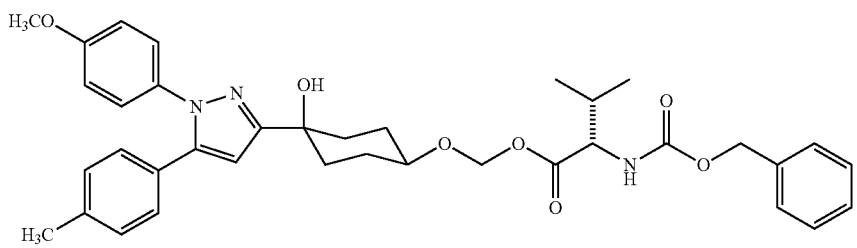

To a solution of 1-(1-(4-methoxyphenyl)-5-(p-tolyl)-1H-pyrazol-3-yl)-cyclohexane-cis-1,4-diol (Example 2-B) (199 mg, 0.506 mmol) in dichloromethane (3.00 mL), molecular sieves 4A (300 mg) and diisopropyl ethylamine (0.210 mL, 1.21 mmol) were added at room temperature, and the resulting solution was cooled to −50° C. Subsequently, (S)-iodomethyl 2-benzyloxycarbonylamino-3-methylbutanoate (0.187 mL, 1.26 mmol) and silver trifluoromethanesulfonate (232 mg, 0.904 mmol) were added at the same temperature, and the obtained solution was stirred for 2 hours. Thereafter, the resulting solution was stirred at −30° C. for 14 hours. Saturated sodium bicarbonate solution was added to the reaction solution, and the resulting solution was filtered through Celite. The filtrate was washed with brine, and the organic layer was dried over anhydrous sodium sulfate and concentrated under reduced pressure. The residue was purified by flash chromatography (silica gel, n-hexane/ethyl acetate) to obtain the captioned compound (123 mg, 0.192 mmol, 64%) as a colorless amorphous product.

$^1$H-NMR (400 MHz, CDCl$_3$) δ: 0.92 (3H, d, J=6.4 Hz), 1.01 (3H, d, J=6.4 Hz), 1.88-1.99 (6H, m), 2.02-2.09 (2H, m), 2.20-2.26 (1H, m), 2.34 (3H, s), 2.50 (1H, s), 3.66-3.72 (1H, m), 3.81 (3H, s), 4.32-4.36 (1H, m), 5.12 (2H, s), 5.38 (1H, d, J=6.4 Hz), 5.50 (1H, d, J=6.4 Hz), 6.37 (1H, s), 6.83-6.87 (2H, m), 7.08-7.11 (4H, m), 7.18-7.24 (2H, m), 7.29-7.38 (5H, m).

ESI-MS: m/z=624 (M−OH)$^+$

Reference Example 100

Dibenzyl 4-hydroxy-4-(1-(4-methoxyphenyl)-5-(p-tolyl)-1H-pyrazol-3-yl)-cis-cyclohexylphosphate

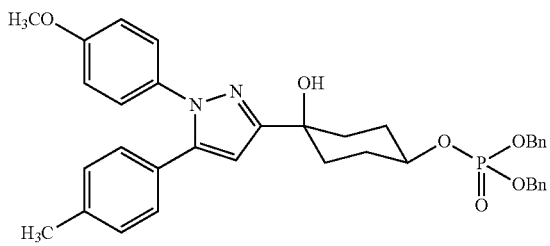

To a solution of 1-(1-(4-methoxyphenyl)-5-(p-tolyl)-1H-pyrazol-3-yl)cyclohexanecis-1,4-diol (Example 2-B) (200 mg, 0.528 mmol) in tetrahydrofuran (2.6 mL), 55% sodium hydride (55.3 mg, 1.27 mmol) and tetrabenzylpyrophosphonate (370 mg, 0.687 mmol) were sequentially added with stirring under ice-cooling, and the obtained solution was stirred at room temperature for 15 hours. The reaction solution was cooled in ice and water was added thereto. The resulting solution was extracted with ethyl acetate. The organic layer was washed with brine, dried over anhydrous sodium sulfate and concentrated under reduced pressure. The residue was purified by flash chromatography (silica gel, n-hexane/ethyl acetate) to obtain the captioned compound (251 mg, 0.393 mmol, 74%) as a colorless transparent oily compound.

$^1$H-NMR (400 MHz, CDCl$_3$) δ: 1.87-2.11 (8H, m), 2.33 (3H, s), 3.79 (3H, s), 4.42-4.51 (1H, m), 5.00-5.12 (4H, m), 6.34 (1H, s), 6.81-6.87 (2H, m), 7.09 (4H, s), 7.16-7.23 (2H, m), 7.29-7.37 (10H, m).

ESI-MS: m/z=639 (M+H)$^+$

With regard to the compounds, the compounds of the following Examples 1 to 71 and Comparative Examples 1 to 30 were synthesized. As the compounds used for the syntheses of the compounds of Examples, for which a synthesis method is not described, commercially available compounds were used.

Example 1

1-(1-(4-Methoxyphenyl)-5-(p-tolyl)-1H-pyrazol-3-yl)cyclohexanol

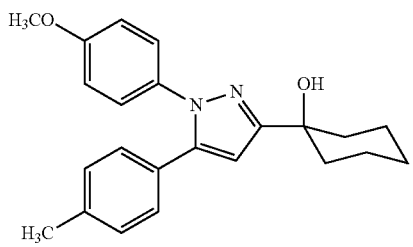

To a suspension of 4-methoxyphenylhydrazine (165 mg, 0.944 mmol) in ethanol (5.0 mL), triethylamine (258 μL, 1.88 mmol) was added, and the obtained solution was stirred at room temperature for 30 minutes. The resulting solution was added to a solution of 3-(1-hydroxycyclohexyl)-1-(4-tolyl)-2-propyn-1-one (Reference Example 14) (214 mg, 0.883 mmol) in ethanol (3.0 mL), and the resulting mixture was stirred at room temperature for 20 hours. The reaction solution was concentrated under reduced pressure, and distilled water was added to the residue. The resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain the title compound (141 mg, 0.389 mmol, 44%) as a yellow amorphous product.

$^1$H-NMR (400 MHz, CDCl$_3$) δ: 1.31-1.42 (1H, m), 1.54-2.03 (9H, m), 2.33 (3H, s), 2.52 (1H, brs), 3.81 (3H, s), 6.40 (1H, s), 6.84 (2H, d, J=8.8 Hz), 7.09 (4H, s), 7.21 (2H, d, J=8.8 Hz).

Example 2

1-(1-(4-Methoxyphenyl)-5-(p-tolyl)-1H-pyrazol-3-yl)cyclohexan-trans-1,4-diol (2-A)

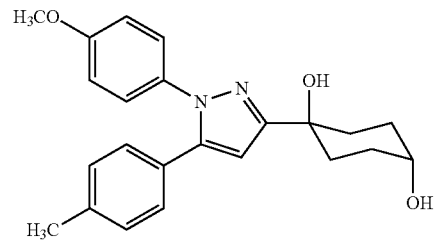

1-(1-(4-Methoxyphenyl)-5-(p-tolyl)-1H-pyrazol-3-yl)cyclohexan-cis-1,4-diol (2-B)

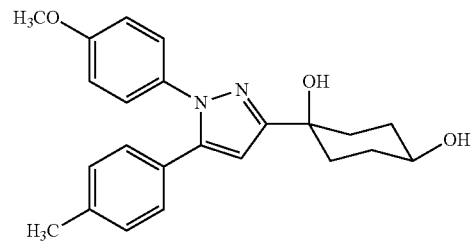

To a solution of 4-hydroxy-4-(1-(4-methoxyphenyl)-5-(p-tolyl)-1H-pyrazol-3-yl)-cyclohexan-1-one (Example 37) (8.00 g, 21.3 mmol) in methanol (200 mL), sodium borohydride (804 mg, 21.3 mmol) was added. The obtained solution was stirred at room temperature for 2 hours, and then poured into 1 M hydrochloric acid. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound 2-A (1.66 g, 4.39 mmol, 21%) as a white solid, and the title compound 2-B (4.85 g, 12.8 mmol, 60%) as a white solid.

2-A: $^1$H-NMR (400 MHz, CDCl$_3$) δ: 1.36 (1H, d, J=3.6 Hz), 1.64-1.72 (2H, m), 1.77-1.83 (2H, m), 2.04-2.12 (2H, m), 2.32-2.39 (5H, m), 2.56 (1H, s), 3.81 (3H, s), 4.03-4.06 (1H, m), 6.43 (1H, s), 6.85 (2H, d, J=8.8 Hz), 7.10 (4H, s), 7.21 (2H, d, J=8.8 Hz).

IR (KBr, cm$^{-1}$): 3344, 2929, 2875, 1740, 1516, 1443, 1369, 1251, 1032, 1001, 832.

ESI-MS: m/z=379 (M+H)$^+$

Mp 151-153° C.

Anal. Calcd for C23H26N2O3: C, 72.99; H, 6.92; N, 7.40. found: C, 72.97; H, 6.92; N, 7.34.

2-B: $^1$H-NMR (400 MHz, CDCl$_3$) δ: 1.44 (1H, s), 1.81-1.99 (6H, m), 2.04-2.12 (2H, m), 2.33 (3H, s), 2.56 (1H, s), 3.70-3.77 (1H, m), 3.80 (3H, s), 6.37 (1H, s), 6.85 (2H, d, J=8.8 Hz), 7.09 (4H, s), 7.20 (2H, d, J=8.8 Hz).

IR (KBr, cm$^{-1}$): 3303, 2918, 1517, 1442, 1366, 1248, 1063, 1026, 837, 807.

ESI-MS: m/z=379 (M+H)$^+$

Mp 164-166° C.

Anal. Calcd for C23H26N2O3: C, 72.99; H, 6.92; N, 7.40. found: C, 72.87; H, 6.86; N, 7.22.

Example 3

1-(1-(4-Methoxyphenyl)-5-(6-methylpyridin-3-yl)-1H-pyrazol-3-yl)cyclohexan-cis-1,4-diol

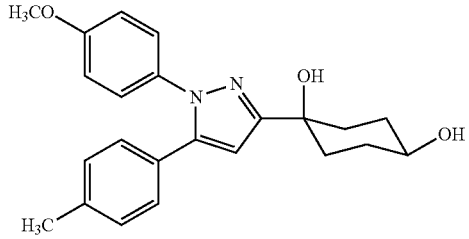

To a solution of 4-hydroxy-4-(1-(4-methoxyphenyl)-5-(6-methylpyridin-3-yl)-1H-pyrazol-3-yl)-cyclohexan-1-one (Example 38) (109.5 mg, 0.29 mmol) in methanol (1.5 mL), sodium borohydride (12.1 mg, 0.32 mmol) was added. The obtained solution was stirred at room temperature for 40 minutes, and 1 M hydrochloric acid was then added thereto. The reaction solution was washed with ethyl acetate, and the aqueous layer was basified with 1 M aqueous sodium hydroxide solution, followed by extraction of the resulting mixture twice with ethyl acetate. The organic layers were washed with brine, dried over anhydrous sodium sulfate, and concentrated under reduced pressure. The residue was purified by flash chromatography (silica gel, ethyl acetate) to obtain the title compound (30.6 mg, 0.81 mmol, 28%) as a white solid.

$^1$H-NMR (400 MHz, CDCl$_3$) δ: 1.59 (1H, brs), 1.81-2.00 (6H, m), 2.05-2.08 (2H, m), 2.55 (3H, s), 2.61 (1H, s), 3.71-3.78 (1H, m), 3.81 (3H, s), 6.46 (1H, s), 6.86 (2H, d, J=8.8 Hz), 7.06 (1H, d, J=8.0 Hz), 7.18 (2H, d, J=8.8 Hz), 7.32 (1H, dd, J=2.0, 8.0 Hz), 8.40 (1H, d, J=2.0 Hz).

IR (KBr, cm$^{-1}$): 3444, 2933, 2858, 1516, 1249, 1067, 968, 839.

ESI-MS: m/z=380 (M+H)$^+$

Example 4

1-(1,5-Bis(4-methoxyphenyl)-1H-pyrazol-3-yl)cyclohexan-trans-1,4-diol (4-A)

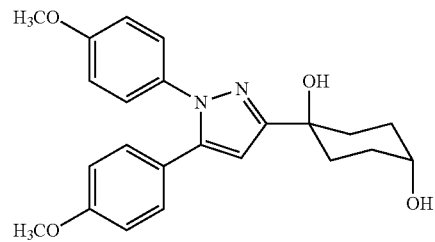

1-(1,5-Bis(4-methoxyphenyl)-1H-pyrazol-3-yl)cyclohexan-cis-1,4-diol (4-B)

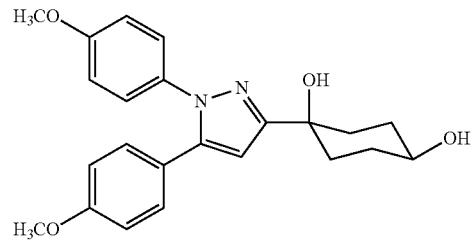

To a solution of 4-(1,5-bis(4-methoxyphenyl)-1H-pyrazol-3-yl)-4-hydroxy-cyclohexan-1-one (Example 39) (523 mg, 1.38 mmol) in methanol, sodium borohydride (65 mg, 1.7 mmol) was added. The obtained solution was stirred at room temperature for 1.5 hours, and concentrated under reduced pressure. Distilled water was added to the residue, and the resulting solution was extracted with ethyl acetate. The organic layer was dried over anhydrous magnesium sulfate, and concentrated under reduced pressure. The residue was purified by flash chromatography to separate into low polar component and high polar component. The low polar component was purified by recrystallization (ethyl acetate/n-hexane=2/1) to obtain the title compound 4-A (79 mg, 0.20 mmol, 14%) as a white crystal. The high polar component was purified by recrystallization (ethyl acetate/n-hexane=2/1) to obtain the title compound 4-B (186 mg, 0.471 mmol, 34%) as a white crystal.

4-A: $^1$H-NMR (400 MHz, CDCl$_3$) δ: 1.33 (1H, d, J=3.4 Hz), 1.63-1.73 (2H, m), 1.75-1.84 (2H, m), 2.03-2.13 (2H, m), 2.30-2.39 (2H, m), 2.55 (1H, s), 3.80 (3H, s), 3.81 (3H, s), 4.02-4.08 (1H, m), 6.40 (1H, s), 6.82 (2H, d, J=8.8 Hz), 6.85 (2H, d, J=8.8 Hz), 7.14 (2H, d, J=8.8 Hz), 7.21 (2H, d, J=8.8 Hz).

IR (KBr, cm$^{-1}$): 3379, 1613, 1517, 1503, 1251, 1180, 1032, 1001, 835.

ESI-MS: m/z=395 (M+H)$^+$

4-B: $^1$H-NMR (400 MHz, CDCl$_3$) δ: 1.41 (1H, d, J=4.1 Hz), 1.79-2.55 (8H, m), 2.55 (1H, s), 3.69-3.78 (1H, m), 3.80 (3H, s), 3.81 (3H, s), 6.34 (1H, s), 6.81 (2H, d, J=8.8 Hz), 6.85 (2H, d, J=8.8 Hz), 7.13 (2H, d, J=8.8 Hz), 7.20 (2H, d, J=8.8 Hz).

IR (KBr, cm$^{-1}$): 3385, 1613, 1517, 1503, 1250, 1064, 1031, 970, 835.

ESI-MS: m/z=395 (M+H)$^+$

Example 5

1-(5-(4-Chlorophenyl)-1-(4-methoxyphenyl)-1H-pyrazol-3-yl)cyclohexan-trans-1,4-diol (5-A)

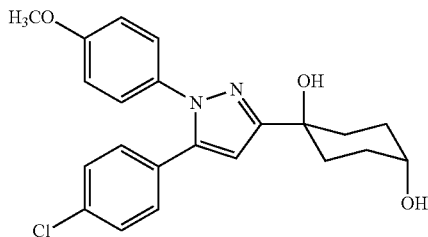

1-(5-(4-Chlorophenyl)-1-(4-methoxyphenyl)-1H-pyrazol-3-yl)cyclohexan-cis-1,4-diol (5-B)

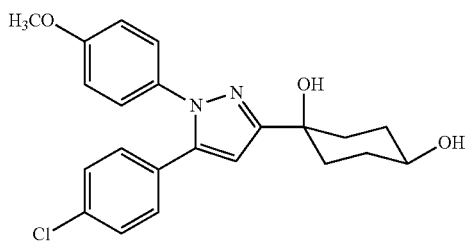

To a solution of 4-(5-(4-chlorophenyl)-1-(4-methoxyphenyl)-1H-pyrazol-3-yl)-4-hydroxy-cyclohexan-1-one (Example 40) (619 mg, 1.56 mmol) in methanol (15.6 mL), sodium borohydride (59.0 mg, 1.56 mmol) was added. The obtained solution was stirred at room temperature for 1 hour, and then poured into 1 M hydrochloric acid. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound 5-A (131 mg, 0.328 mmol, 21%) as a white solid, and the title compound 5-B (291 mg, 0.730 mmol, 47%) as a white solid.

5-A: $^1$H-NMR (400 MHz, CDCl$_3$) δ: 1.32 (1H, d, J=3.2 Hz), 1.63-1.73 (2H, m), 1.76-1.84 (2H, m), 2.03-2.12 (2H, m), 2.30-2.39 (2H, m), 2.50 (1H, s), 3.82 (3H, s), 4.02-4.09 (1H, m), 6.46 (1H, s), 6.84-6.87 (2H, m), 7.14 (2H, d, J=8.8 Hz), 7.19 (2H, d, J=8.8 Hz), 7.26-7.28 (2H, m).

ESI-MS: m/z=399 (M+H)$^+$

5-B: $^1$H-NMR (400 MHz, CDCl$_3$) δ: 1.41 (1H, d, J=5.2 Hz), 1.82-2.09 (8H, m), 2.49 (1H, s), 3.70-3.78 (1H, s), 3.82 (3H, s), 6.41 (1H, s), 6.85-6.87 (2H, m), 7.13 (2H, d, J=8.4 Hz), 7.18 (2H, d, J=8.4 Hz), 7.25-7.27 (2H, m).

ESI-MS: m/z=399 (M+H)$^+$

Example 6

1-(1-(4-Chlorophenyl)-5-p-tolyl-1H-pyrazol-3-yl)cyclohexan-trans-1,4-diol (6-A)

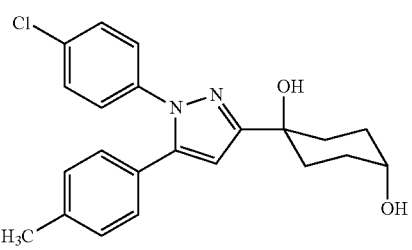

1-(1-(4-Chlorophenyl)-5-p-tolyl-1H-pyrazol-3-yl)cyclohexan-cis-1,4-diol (6-B)

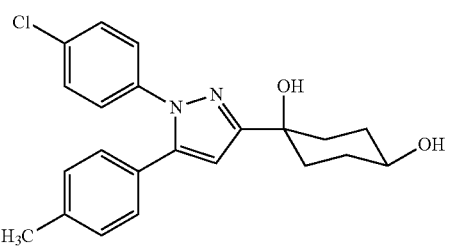

To a solution of 4-hydroxy-4-(1-(4-chlorophenyl)-5-(p-tolyl)-1H-pyrazol-3-yl)-cyclohexan-1-one (Example 41) (510 mg, 1.34 mmol) in methanol (13 mL), sodium borohydride (53 mg, 1.40 mmol) was added, and the obtained solution was stirred at room temperature for 2 hours. The reaction solution was concentrated under reduced pressure, and then dissolved into ethyl acetate, and washed with distilled water and brine. The organic layer was dried over anhydrous sodium sulfate, and concentrated under reduced pressure. The residue was purified by flash chromatography (silica gel, n-hexane/ethyl acetate) to obtain the title compound 6-A (114 mg, 0.298 mmol, 22%) as a white solid, and the title compound 6-B (360 mg, 0.940 mmol, 70%) as a white solid.

6-A: $^1$H-NMR (400 MHz, CDCl$_3$) δ: 1.36 (1H, br), 1.65-1.72 (2H, m), 1.77-1.82 (2H, m), 2.04-2.11 (2H, m), 2.31-2.38 (2H, m), 2.36 (3H, s), 2.51 (1H, s), 4.03-4.08 (1H, m), 6.44 (1H, s), 7.10 (2H, d, J=8.8 Hz), 7.13 (2H, d, J=8.8 Hz), 7.22-7.30 (4H, m).

IR (KBr, cm$^{-1}$): 3349, 2918, 1497, 1440, 1366, 1240, 1098, 1007, 969, 833, 810.

ESI-MS: m/z=383 (M+H)$^+$

6-B: $^1$H-NMR (400 MHz, CDCl$_3$) δ: 1.45 (1H, br), 1.80-1.99 (6H, m), 2.03-2.07 (2H, m), 2.35 (3H, s), 2.51 (1H, s), 3.70-3.80 (1H, m), 6.39 (1H, s), 7.09 (2H, d, J=8.4 Hz), 7.13 (2H, d, J=8.4 Hz), 7.21-7.24 (2H, m), 7.27-7.31 (2H, m).

IR (KBr, cm$^{-1}$): 3365, 2946, 1496, 1442, 1368, 1241, 1095, 1059, 1014, 970, 887.

ESI-MS: m/z=365 (M−OH)$^+$

The compounds of the following Examples were prepared by the same procedure as described above.

TABLE 7-1

| Example | Structural Formula | Compound Data |
|---|---|---|
| 7 | | ¹H-NMR (400 MHz, CDCl₃) δ: 1.34 (1H, d, J = 3.2 Hz), 1.64-1.72 (2H, m), 1.76-1.83 (2H, m), 2.03-2.12 (2H, m), 2.30-2.39 (2H, m), 2.45 (1H, s), 4.03-4.09 (1H, m), 6.48 (1H, s), 7.15 (2H, d, J = 8.8 Hz), 7.22 (2H, d, J = 8.8 Hz), 7.30-7.33 (4H, m).<br>ESI-MS: m/z = 403 (M + H)⁺ |
| 8 | | ¹H-NMR (400 MHz, CDCl₃) δ: 1.45 (1H, d, J = 4.0 Hz), 1.80-2.07 (8H, m), 2.46 (1H, s), 3.70-3.79 (1H, s), 6.43 (1H, s), 7.14 (2H, d, J = 8.8 Hz), 7.21 (2H, d, J = 8.8 Hz), 7.29-7.33 (4H, m).<br>ESI-MS: m/z = 403 (M + H)⁺ |
| 9 | | ¹H-NMR (400 MHz, CDCl₃) δ: 1.33 (1H, d, J = 3.2 Hz), 1.65-1.73 (2H, m), 1.78-1.84 (2H, m), 2.04-2.13 (2H, m), 2.32-2.40 (2H, m), 2.51 (1H, s), 4.03-4.09 (1H, m), 6.48 (1H, s), 7.14-7.16 (2H, m), 7.26-7.28 (7H, m).<br>ESI-MS: m/z = 369 (M + H)⁺ |
| 10 | | ¹H-NMR (400 MHz, CDCl₃) δ: 1.43 (1H, d, J = 5.2 Hz), 1.81-2.09 (8H, m), 2.50 (1H, s), 3.71-3.79 (1H, m), 6.43 (1H, s), 7.12-7.16 (2H, m), 7.25-7.38 (7H, m).<br>ESI-MS: m/z = 369 (M + H)⁺ |
| 11 | | ¹H-NMR (400 MHz, CDCl₃) δ : 1.41 (1H, brs), 1.64-1.72 (2H, m), 1.77-1.83 (2H, m), 2.04-2.11 (2H, m), 2.31-2.38 (2H, m), 2.34 (3H, s), 2.35 (3H, s), 2.59 (1H, s), 4.02-4.07 (1H, m), 6.43 (1H, s), 7.09-7.11 (4H, m), 7.12 (2H, d, J = 8.4 Hz), 7.18 (2H, d, J = 8.4 Hz).<br>IR (KBr, cm⁻¹): 3343, 2918, 1518, 1440, 1367, 1266, 1240, 1196, 1159, 1107, 1007, 824, 810.<br>ESI-MS: m/z = 363 (M + H)⁺ |

TABLE 7-2

| Example | Structural Formula | Compound Data |
|---|---|---|
| 12 | | $^1$H-NMR (400 MHz, CDCl$_3$) δ: 1.48 (1H, brs), 1.80-1.99 (6H, m), 2.02-2.09 (2H, m), 2.34 (3H, s), 2.35 (3H, s), 2.61 (1H, s), 3.70-3.78 (1H, m), 6.38 (1H, s), 7.08-7.12 (4H, m), 7.12 (2H, d, J = 8.8 Hz), 7.17 (2H, d, J = 8.8 Hz).<br>IR (KBr, cm$^{-1}$): 3375, 2937, 2870, 1519, 1502, 1440, 1362, 1217, 1193, 1112, 1064, 1042, 1017, 973, 886, 821, 804.<br>ESI-MS: m/z = 345 (M − OH)$^+$ |
| 13 | | $^1$H-NMR (400 MHz, CDCl$_3$) δ: 1.47 (1H, brs), 1.64-1.73 (2H, m), 1.76-1.85 (2H, m), 2.03-2.12 (2H, m), 2.31-2.40 (2H, m), 2.34 (3H, s), 2.62 (1H, s), 4.02-4.08 (1H, m), 6.45 (1H, s), 7.08-7.14 (4H, m), 7.26-7.36 (5H, m).<br>IR (KBr, cm$^{-1}$): 3337, 2920, 1599, 1506, 1437, 1366, 1005, 810, 765, 696.<br>ESI-MS: m/z = 349 (M + H)$^+$ |
| 14 | | $^1$H-NMR (400 MHz, CDCl$_3$) δ: 1.50 (1H, brs), 1.80-2.00 (6H, m), 2.03-2.09 (2H, m), 2.34 (3H, s), 2.60 (1H, s), 3.70-3.79 (1H, m), 6.40 (1H, s), 7.08-7.12 (4H, m), 7.27-7.35 (5H, m).<br>IR (KBr, cm$^{-1}$): 3374, 2919, 1596, 1505, 1440, 1361, 1217, 1112, 1064, 1044, 1019, 973, 886, 819, 799, 771, 693.<br>ESI-MS: m/z = 331 (M − OH)$^+$ |
| 15 | | $^1$H-NMR (400 MHz, CDCl$_3$) δ: 1.42 (1H, d, J = 4.8 Hz), 1.79-2.01 (6H, m), 2.03-2.08 (2H, m), 2.54 (1H, s), 3.71-3.80 (1H, m), 3.81 (3H, s), 6.41 (1H, s), 6.84 (2H, d, J = 6.8 Hz), 7.18-7.23 (4H, m), 7.28-7.30 (3H, m).<br>ESI-MS: m/z = 365 (M + H)$^+$ |

TABLE 7-3

| Example | Structural Formula | Compound Data |
|---|---|---|
| 16 | | $^1$H-NMR (400 MHz, CDCl$_3$) δ: 1.34 (1H, d, J = 3.6 Hz), 1.65-1.73 (2H, m), 1.17-1.85 (2H, m), 2.03-2.12 (2H, m), 2.32-2.40 (2H, m), 2.54 (1H, s), 3.81 (3H, s), 4.00-4.10 (1H, m), 6.46 (1H, s), 6.85 (2H, d, J = 8.8 Hz), 7.19-7.24 (4H, m), 7.28-7.31 (3H, m).<br>ESI-MS: m/z = 365 (M + H)$^+$ |
| 17 | | $^1$H-NMR (400 MHz, CDCl$_3$) δ: 1.34 (1H, d, J = 3.6 Hz), 1.62-1.73 (2H, m), 1.77-1.85 (2H, m), 2.03-2.12 (2H, m), 2.31-2.40 (5H, m), 2.57 (1H, s), 4.00-4.08 (1H, m), 6.61 (1H, s), 7.12 (2H, d, J = 8.4 Hz), 7.17 (2H, d, J = 8.8 Hz), 7.21-7.24 (2H, m), 7.28-7.30 (3H, m).<br>ESI-MS: m/z = 349 (M + H)$^+$ |

TABLE 7-3-continued

| Example | Structural Formula | Compound Data |
|---|---|---|
| 18 | (structure) | $^1$H-NMR (400 MHz, CDCl$_3$) δ: 1.79-2.00 (6H, m), 2.03-2.08 (2H, m), 2.34 (3H, s), 2.57 (1H, s), 3.70-3.79 (1H, m), 6.41 (1H, s), 7.10 (2H, d, J = 8.4 Hz), 7.16 (2H, d, J = 8.4 Hz), 7.27-7.31 (3H, m), 7.19-7.23 (2H, m). ESI-MS: m/z = 349 (M + H)$^+$ |
| 19 | (structure) | $^1$H-NMR (400 MHz, CDCl$_3$) δ: 1.35 (1H, d, J = 3.6 Hz), 1.62-1.73 (2H, m), 1.75-1.86 (2H, m), 2.02-2.13 (2H, m), 2.29-2.40 (5H, m), 2.58 (1H, s), 3.80 (3H, s), 4.01-4.09 (1H, m), 6.40 (1H, s), 6.82 (2H, d, J = 8.8 Hz), 7.10-7.20 (6H, m). |
| 20 | (structure) | $^1$H-NMR (400 MHz, CDCl$_3$) δ: 1.34 (1H, d, J = 5.6 Hz), 1.80-2.10 (8H, m), 2.34 (3H, s), 2.59 (1H, s), 3.68-3.79 (1H, m), 3.80 (3H, s), 6.34 (1H, s), 6.81 (2H, d, J = 8.4 Hz), 7.08-7.20 (6H, m). |

TABLE 7-4

| Example | Structural Formula | Compound Data |
|---|---|---|
| 21 | (structure) | $^1$H-NMR (400 MHz, CDCl$_3$) δ: 1.48 (1H, s), 1.62-1.72 (2H, m), 1.73-1.83 (2H, m), 2.02-2.12 (2H, m), 2.30-2.39 (2H, m), 2.57 (1H, s), 3.82 (3H, s), 4.02-4.06 (1H, m), 6.42 (1H, s), 6.84 (2H, d, J = 8.8 Hz), 7.13 (2H, d, J = 12.0 Hz), 7.23 (2H, d, J = 8.8 Hz), 7.29 (2H, d, J = 8.8 Hz). ESI-MS: m/z = 399 (M + H)$^+$ |
| 22 | (structure) | $^1$H-NMR (400 MHz, CDCl$_3$) δ: 1.79-1.99 (6H, m), 2.03-2.07 (3H, m), 3.70-3.79 (1H, m), 3.81 (3H, s), 6.37 (1H, s), 6.84 (2H, d, J = 8.8 Hz), 7.14 (2H, d, J = 8.8 Hz), 7.22 (2H, d, J = 8.8 Hz), 7.29 (2H, d, J = 8.8 Hz). ESI-MS: m/z = 399 (M + H)$^+$ |
| 23 | (structure) | $^1$H-NMR (400 MHz, CDCl$_3$) δ: 1.38 (1H, s), 1.64-1.74 (2H, m), 1.76-1.85 (2H, m), 2.03-2.13 (2H, m), 2.31-2.40 (2H, m), 2.58 (1H, s), 3.81 (3H, s), 4.06 (1H, s), 6.42 (1H, s), 6.82 (2H, d, J = 8.8 Hz), 7.14 (2H, d, J = 8.8 Hz), 7.28-7.37 (5H, m). ESI-MS: m/z = 365 (M + H)$^+$ |

TABLE 7-4-continued

| Example | Structural Formula | Compound Data |
|---|---|---|
| 24 | | ¹H-NMR (400 MHz, CDCl₃) δ: 1.47 (1H, s), 1.79-1.99 (6H, m), 2.03-2.07 (2H, m), 2.59 (1H, s), 3.70-3.39 (1H, m), 3.80 (3H, s), 6.37 (1H, s), 6.82 (2H, d, J = 8.6 Hz), 7.13 (2H, d, J = 8.6 Hz), 7.27-7.36 (5H, m).<br>ESI-MS: m/z = 365 (M + H)⁺ |

TABLE 7-5

| Example | Structural Formula | Compound Data |
|---|---|---|
| 25 | | ¹H-NMR (400 MHz, CDCl3) δ: 1.35 (1H, s), 1.67-1.71 (2H, m), 1.78-1.84 (2H, m), 2.0-2.11 (2H, m), 2.33-2.40 (2H, m), 2.49 (1H, s), 3.83 (3H, s), 4.07 (1H, m), 6.53 (1H, s), 6.87 (2H, d, J = 8.2 Hz), 7.19 (2H, d, J = 8.2 Hz), 7.33 (2H, d, J = 8.2 Hz), 7.55 (2H, d, J = 8.2 Hz).<br>ESI-MS: m/z = 433 (M + H)⁺ |
| 26 | | ¹H-NMR (400 MHz, CDCl3) δ: 1.44 (1H, d, J = 4.0 Hz), 1.84-2.01 (8H, m), 2.48 (1H, s), 3.75 (1H, s), 3.82 (3H, s), 6.49 (1H, s), 6.87 (2H, d, J = 9.2 Hz), 7.19 (2H, d, J = 9.2 Hz), 7.32 (2H, d, J = 8.2 Hz), 7.55 (2H, d, J = 8.2 Hz).<br>ESI-MS: m/z = 433 (M + H)⁺ |
| 27 | | ¹H-NMR (400 MHz, CDCl3) δ: 1.23 (3H, t, J = 7.6 Hz), 1.33 (1H, br), 1.64-1.73 (2H, m), 1.77-1.84 (2H, m), 2.03-2.12 (2H, m), 2.31-2.40 (2H, m), 2.55 (1H, s), 2.63 (2H, q, J = 7.6 Hz), 3.81 (3H, s), 4.02-4.07 (1H, m), 6.43 (1H, s), 6.83-6.89 (2H, m), 7.12 (4H, s), 7.19-7.28 (2H, m).<br>ESI-MS: m/z = 393 (M + H)⁺ |
| 28 | | ¹H-NMR (400 MHz, CDCl3) δ: 1.23 (3H, t, J = 7.6 Hz), 1.41 (1H, d, J = 4.4 Hz), 1.80-2.09 (8H, m), 2.55 (1H, s), 2.63 (2H, q, J = 7.6 Hz), 3.69-3.83 (4H, m), 6.38 (1H, s), 6.82-6.87 (2H, m), 7.12 (4H, s), 7.17-7.28 (2H, m).<br>ESI-MS: m/z = 393 (M + H)⁺ |

TABLE 7-6
| Example | Structural Formula | Compound Data |
|---|---|---|
| 29 | 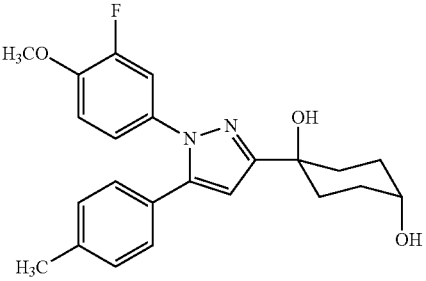 | $^1$H-NMR (400 MHz, CDCl$_3$) δ: 1.32 (1H, br), 1.65-1.72 (2H, m), 1.77-1.83 (2H, m), 2.04-2.11 (2H, m), 2.30-2.39 (5H, m), 2.48 (1H, br), 3.89 (3H, s), 4.02-4.08 (1H, m), 6.43 (1H, s), 6.88 (1H, t, J = 8.8 Hz), 6.93-7.02 (1H, m), 7.08-7.15 (5H, m). ESI-MS: m/z = 397 (M + H)$^+$ |
| 30 | 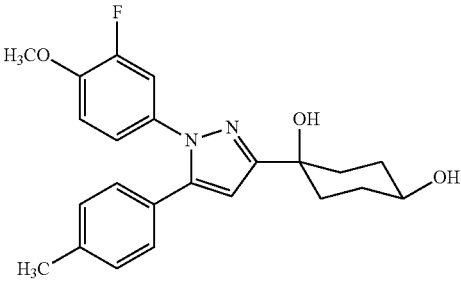 | $^1$H-NMR (400 MHz, CDCl$_3$) δ: 1.41 (1H, br), 1.80-2.08 (8H, m), 2.35 (3H, s), 2.48 (1H, s), 3.70-3.80 (1H, m), 3.89 (3H, s), 6.38 (1H, s), 6.88 (1H, t, J = 8.8 Hz), 6.96-7.01 (1H, m), 7.06-7.14 (5H, m). ESI-MS: m/z = 397 (M + H)$^+$ |
| 31 | 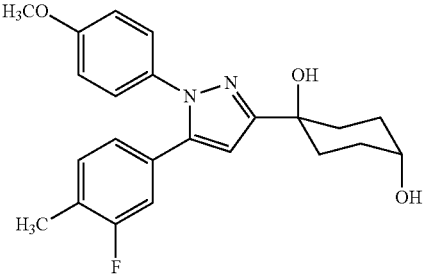 | $^1$H-NMR (400 MHz, CDCl$_3$) δ 1.63-1.84 (4H, m), 2.03-2.12 (2H, m), 2.26 (3H, d, J = 1.6 Hz), 2.31-2.41 (2H, m), 2.51 (1H, br), 3.82 (3H, s), 4.03-4.08 (1H, m), 6.44 (1H, s), 6.84-6.90 (4H, m), 7.08 (1H, t, J = 8.0 Hz), 7.18-7.23 (2H, m). ESI-MS: m/z = 397 (M + H)$^+$ |
| 32 | 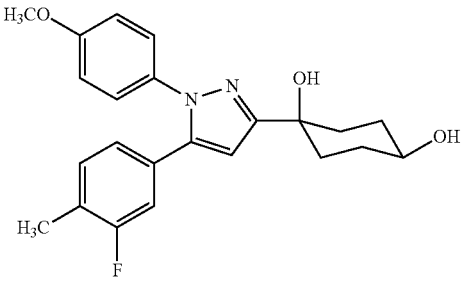 | $^1$H-NMR (400 MHz, CDCl$_3$) δ: 1.41 (1H, d, J = 4.8 Hz), 1.81-2.08 (8H, m), 2.25 (3H, d, J = 1.6 Hz), 2.51 (1H, s), 3.69-3.78 (1H, m), 3.82 (3H, s), 6.39 (1H, s), 6.84-6.89 (4H, m), 7.09 (1H, t, J = 7.6 Hz), 7.17-7.24 (2H, m). ESI-MS: m/z = 397 (M + H)$^+$ |

TABLE 7-7

| Example | Structural Formula | Compound Data |
|---|---|---|
| 33 | | ¹H-NMR (400 MHz, CDCl₃) δ: 1.32 (1H, br), 1.65-1.72 (2H, m), 1.77-1.83 (2H, m), 2.04-2.11 (2H, m), 2.30-2.39 (5H, m), 2.48 (1H, br), 3.89 (3H, s), 4.02-4.08 (1H, m), 6.43 (1H, s), 6.88 (1H, t, J = 8.8 Hz), 6.93-7.02 (1H, m), 7.08-7.15 (5H, m).<br>ESI-MS: m/z = 397 (M + H)⁺ |
| 34 | | ¹H-NMR (400 MHz, CDCl₃) δ: 1.41 (1H, br), 1.80-2.08 (8H, m), 2.35 (3H, s), 2.48 (1H, s), 3.70-3.80 (1H, m), 3.89 (3H, s), 6.38 (1H, s), 6.88 (1H, t, J = 8.8 Hz), 6.96-7.01 (1H, m), 7.06-7.14 (5H, m).<br>ESI-MS: m/z = 397 (M + H)⁺ |
| 35 | | ¹H-NMR (400 MHz, CDCl₃) δ: 1.63-1.84 (4H, m), 2.03-2.12 (2H, m), 2.26 (3H, d, J = 1.6 Hz), 2.31-2.41 (2H, m), 2.51 (1H, br), 3.82 (3H, s), 4.03-4.08 (1H, m), 6.44 (1H, s), 6.84-6.90 (4H, m), 7.08 (1H, t, J = 8.0 Hz), 7.18-7.23 (2H, m).<br>ESI-MS: m/z = 397 (M + H)⁺ |
| 36 | | ¹H-NMR (400 MHz, CDCl₃) δ: 1.41 (1H, d, J = 4.8 Hz), 1.81-2.08 (8H, m), 2.25 (3H, d, J = 1.6 Hz), 2.51 (1H, s), 3.69-3.78 (1H, m), 3.82 (3H, s), 6.39 (1H, s), 6.84-6.89 (4H, m), 7.09 (1H, t, J = 7.6 Hz), 7.17-7.24 (2H, m).<br>ESI-MS: m/z = 397 (M + H)⁺ |

Example 37

4-Hydroxy-4-(1-(4-methoxyphenyl)-5-(p-tolyl)-1H-pyrazol-3-yl)cyclohexan-1-one

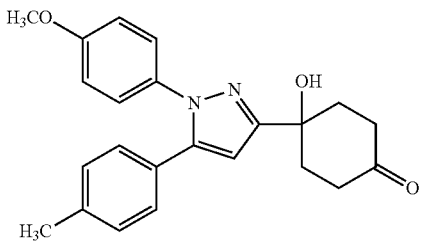

To a solution of 8-(1-(4-methoxyphenyl)-5-(p-tolyl)-1H-pyrazol-3-yl)-1,4-dioxaspiro[4.5]decan-8-ol (Reference Example 30) (14.6 g, 34.7 mmol) in tetrahydrofuran (69.4 mL), 6 M hydrochloric acid (138.9 mL) was added, and the obtained solution was stirred at room temperature for 15 hours. The reaction solution was cooled in ice, and 50% aqueous sodium hydroxide solution was added dropwise thereto at 0° C. until it became basic. Thereafter, the resulting solution was extracted with ethyl acetate. The organic layer was washed with brine, dried over anhydrous sodium sulfate, and concentrated under reduced pressure. The residue was purified by recrystallization (n-hexane/ethyl acetate, 70° C.) to obtain the title compound (10.5 g, 27.9 mmol, 80%) as a white solid.

¹H-NMR (400 MHz, CDCl₃) δ: 2.33-2.43 (9H, m), 2.87-2.95 (3H, m), 3.82 (3H, s), 6.39 (1H, s), 6.86 (2H, d, J=8.8 Hz), 7.10 (4H, s), 7.22 (2H, d, J=8.8 Hz).

IR (KBr, cm⁻¹): 3321, 2929, 1712, 1518, 1463, 1299, 1249, 1179, 1114, 1027, 961, 821.

ESI-MS: m/z=377 (M+H)⁺

Example 38

4-Hydroxy-4-(1-(4-methoxyphenyl)-5-(6-methylpyridin-3-yl)-1H-pyrazol-3-yl)-cyclohexan-1-one

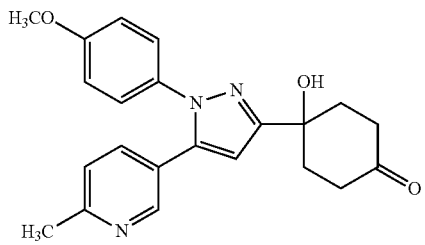

To a solution of 8-(1-(4-methoxyphenyl)-5-(6-methylpyridin-3-yl)-1H-pyrazol-3-yl)-1,4-dioxaspiro[4.5]decan-8-ol (Reference Example 31) (128.8 mg, 0.30 mmol) in tetrahydrofuran (0.6 mL), 6 M hydrochloric acid (1.2 mL) was added, and the obtained solution was stirred at room temperature for 3 hours. The reaction solution was cooled in ice, and 50% aqueous sodium hydroxide solution was added dropwise thereto at 0° C. until it became basic. Thereafter, the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (109.5 mg, 0.29 mmol, 96%) as an amorphous product.

$^1$H-NMR (400 MHz, CDCl$_3$) δ: 2.34-2.44 (6H, m), 2.55 (3H, s), 2.87-2.95 (2H, m), 3.18 (1H, s), 3.82 (3H, s), 6.49 (1H, s), 6.87 (2H, d, J=8.8 Hz), 7.08 (1H, d, J=8.1 Hz), 7.19 (2H, d, J=8.8 Hz), 7.35 (1H, dd, J=2.2, 8.1 Hz), 8.40 (1H, d, J=2.2 Hz).

ESI-MS: m/z=378 (M+H)$^+$

Example 39

4-(1,5-Bis(4-methoxyphenyl)-1H-pyrazol-3-yl)-4-hydroxy-cyclohexan-1-one

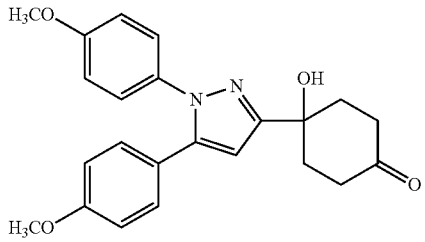

To a solution of 8-(1,5-bis(4-methoxyphenyl)-1H-pyrazol-3-yl)-1,4-dioxaspiro[4.5]decan-8-ol (Reference Example 32) (658 mg, 1.50 mmol) in tetrahydrofuran (3.75 mL), 6 M hydrochloric acid (7.5 mL) was added at 0° C., and the obtained solution was stirred at room temperature for 5 hours. The reaction solution was neutralized by pouring it into ice-cooled 10% aqueous sodium hydroxide solution. The resulting solution was basified by addition of saturated sodium bicarbonate solution, and extracted with ethyl acetate. The organic layer was dried over anhydrous magnesium sulfate, and concentrated under reduced pressure. The residue was purified by flash chromatography (silica gel, n-hexane/ethyl acetate) to obtain the title compound (523 mg, 1.33 mmol, 89%) as an amorphous product.

$^1$H-NMR (400 MHz, CDCl$_3$) δ: 2.30-2.45 (6H, m), 2.86-2.96 (2H, m), 2.99 (1H, s), 3.80 (3H, s), 3.82 (3H, s), 6.36 (1H, s), 6.82 (2H, d, J=8.8 Hz), 6.87 (2H, d, J=8.8 Hz), 7.13 (2H, d, J=8.8 Hz), 7.21 (2H, d, J=8.8 Hz).

ESI-MS: m/z=393 (M+H)$^+$

Example 40

4-(5-(4-Chlorophenyl)-1-(4-methoxyphenyl)-1H-pyrazol-3-yl)-4-hydroxy-cyclohexan-1-one

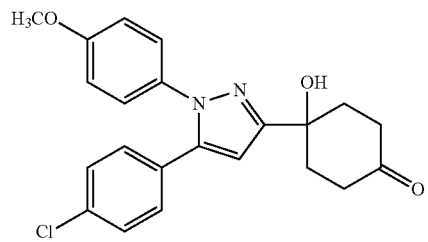

To a solution of 8-(5-(4-chlorophenyl)-1-(4-methoxyphenyl)-1H-pyrazol-3-yl)-1,4-dioxaspiro[4.5]decan-8-ol (Reference Example 33) (756 mg, 1.71 mmol) in tetrahydrofuran (4.3 mL), 6 M hydrochloric acid (8.6 mL) was added, and the obtained solution was stirred at room temperature for 15 hours. The reaction solution was cooled in ice, and 50% aqueous sodium hydroxide solution was added dropwise thereto at 0° C. until it became basic. Thereafter, the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (619 mg, 1.56 mmol, 91%) as an amorphous product.

$^1$H-NMR (400 MHz, CDCl$_3$) δ: 2.31-2.45 (6H, m), 2.85-2.98 (3H, m), 3.82 (3H, s), 6.43 (1H, s), 6.86-6.90 (2H, m), 7.14 (2H, d, J=8.8 Hz), 7.19 (2H, d, J=8.8 Hz), 7.26-7.29 (2H, m).

ESI-MS: m/z=397 (M+H)$^+$

Example 41

4-Hydroxy-4-(1-(4-chlorophenyl)-5-(p-tolyl)-1H-pyrazol-3-yl)-cyclohexan-1-one

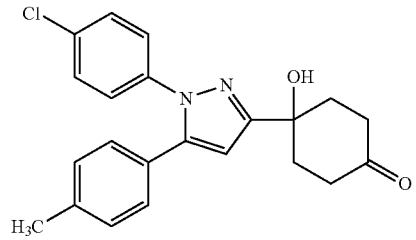

To a solution of 8-(1-(4-chlorophenyl)-5-p-tolyl-1H-pyrazol-3-yl)-1,4-dioxaspiro[4.5]decan-8-ol (Reference Example 34) (931 mg, 2.19 mmol) in tetrahydrofuran (5.5 mL), 6 M hydrochloric acid (11 mL) was added, and the obtained solution was stirred at room temperature for 15 hours. The reaction solution was basified by pouring it into saturated aqueous sodium hydrogen carbonate solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (513 mg, 1.35 mmol, 61%) as a white solid.

$^1$H-NMR (400 MHz, CDCl$_3$) δ: 2.32-2.36 (4H, m), 2.36 (3H, s), 2.38-2.44 (2H, m), 2.87-2.95 (2H, m), 2.90 (1H, s), 6.41 (1H, s), 7.10 (2H, d, J=8.0 Hz), 7.14 (2H, d, J=8.0 Hz), 7.23 (2H, d, J=8.8 Hz), 7.31 (2H, d, J=8.8 Hz).

ESI-MS: m/z=381 (M+H)$^+$

The following compounds were prepared by the same procedure as described above.

TABLE 8-1

| Example | Structural Formula | Compound Data |
|---|---|---|
| 42 | (structure: 1,5-bis(4-chlorophenyl)pyrazol-3-yl-4-hydroxycyclohexanone) | $^1$H-NMR (400 MHz, CDCl$_3$) δ: 2.31-2.45 (6H, m), 2.86-2.96 (3H, m), 6.45 (1H, s), 7.15 (2H, d, J = 8.8 Hz), 7.22 (2H, d, J = 8.8 Hz), 7.31-7.35 (4H, m).<br>ESI-MS: m/z = 401 (M + H)$^+$ |
| 43 | (structure: 1-phenyl-5-(4-chlorophenyl)pyrazol-3-yl-4-hydroxycyclohexanone) | $^1$H-NMR (400 MHz, CDCl$_3$) δ: 2.32-2.44 (6H, m), 2.85-2.95 (2H, m), 3.10 (1H, brs), 6.45 (1H, s), 7.13-7.16 (2H, m), 7.26-7.39 (7H, m).<br>ESI-MS: m/z = 367 (M + H)$^+$ |
| 44 | (structure: 1,5-bis(4-methylphenyl)pyrazol-3-yl-4-hydroxycyclohexanone) | $^1$H-NMR (400 MHz, CDCl$_3$) δ: 2.32-2.45 (6H, m), 2.34 (3H, s), 2.36 (3H, s), 2.87-2.95 (2H, m), 2.98 (1H, s), 6.37 (1H, s), 7.10-7.19 (8H, m).<br>ESI-MS: m/z = 361 (M + H)$^+$ |
| 45 | (structure: 1-phenyl-5-(4-methylphenyl)pyrazol-3-yl-4-hydroxycyclohexanone) | $^1$H-NMR (400 MHz, CDCl$_3$) δ: 2.32-2.45 (6H, m), 2.35 (3H, s), 2.87-2.96 (2H, m), 2.97 (1H, s), 6.41 (1H, s), 7.09-7.13 (4H, m), 7.27-7.37 (5H, m).<br>ESI-MS: m/z = 347 (M + H)$^+$ |
| 46 | (structure: 1-(4-methoxyphenyl)-5-phenylpyrazol-3-yl-4-hydroxycyclohexanone) | $^1$H-NMR (400 MHz, CD$_3$OD) δ: 2.44-2.38 (6H, m), 2.87-2.96 (3H, m), 3.82 (3H, s), 6.43 (1H, s), 6.86 (2H, d, J = 9.0 Hz), 7.19-7.24 (4H, m), 7.29-7.32 (3H, m).<br>ESI-MS: m/z = 363 (M + H)$^+$ |

TABLE 8-1-continued

| Example | Structural Formula | Compound Data |
|---|---|---|
| 47 | (structure) | ¹H-NMR (400 MHz, CDCl₃) δ: 2.32-2.44 (2H, m), 2.35-2.39 (5H, m), 2.43-2.50 (2H, m), 2.89-2.96 (2H, m), 6.43 (1H, s), 7.13 (2H, d, J = 8.8 Hz), 7.17 (2H, d, J = 8.8 Hz), 7.20-7.24 (2H, m), 7.29-7.32 (3H, m). ESI-MS: m/z = 347 (M + H)⁺ |

TABLE 8-2

| Example | Structural Formula | Compound Data |
|---|---|---|
| 48 | (structure) | ¹H-NMR (400 MHz, CDCl3) δ: 2.31-2.34 (2H, m), 2.36 (3H, s), 2.37-2.39 (2H, m), 2.41-2.43 (2H, m), 2.86-2.96 (2H, m), 2.99 (1H, s), 3.80 (3H, s), 6.36 (1H, s), 6.83 (2H, d, J = 8.8 Hz), 7.13-7.19 (6H, m). ESI-MS: m/z = 377 (M + H)⁺ |
| 49 | (structure) | ¹H-NMR (400 MHz, CDCl3) δ: 2.31-2.35 (4H, m), 2.38-2.43 (2H, m), 2.86-2.96 (3H, m), 3.82 (3H, s), 6.38 (1H, s), 6.84 (2H, d, J = 9.0 Hz), 7.13 (2H, d, J = 11.7 Hz), 7.23 (2H, t, J = 8.9 Hz), 7.31 (2H, d, J = 11.5 Hz). ESI-MS: m/z = 397 (M + H)⁺ |
| 50 | (structure) | ¹H-NMR (400 MHz, CDCl3) δ: 2.31-2.45 (6H, m), 2.86-2.96 (2H, m), 3.02 (1H, s), 3.80 (3H, s), 6.37 (1H, s), 6.83 (2H, d, J = 8.8 Hz), 7.14 (2H, d, J = 8.8 Hz), 7.28-7.37 (5H, m). |
| 51 | (structure) | ¹H-NMR (400 MHz, CDCl3) δ: 2.33-2.37 (4H, m), 2.39-2.43 (2H, m), 2.87-2.95 (3H, m), 3.83 (3H, s), 6.50 (1H, s), 6.89 (2H, d, J = 8.0 Hz), 7.20 (2H, d, J = 8.0 Hz), 7.33 (2H, d, J = 8.0 Hz), 7.56 (2H, d, J = 8.0 Hz). ESI-MS: m/z = 431 (M + H)⁺ |
| 52 | (structure) | ¹H-NMR (400 MHz, CDCl3) δ: 1.23 (3H, t, J = 7.6 Hz), 2.31-2.45 (6H, m), 2.64 (2H, q, J = 7.6 Hz), 2.86-2.96 (3H, m), 3.82 (3H, s), 6.39 (1H, s), 6.83-6.89 (2H, m), 7.13 (4H, s), 7.20-7.25 (2H, m). ESI-MS: m/z = 391 (M + H)⁺ |

TABLE 8-3

| Example | Structural Formula | Compound Data |
|---|---|---|
| 53 | | $^1$H-NMR (400 MHz, CDCl$_3$) δ: 2.31-2.45 (9H, m), 2.86-2.97 (3H, m), 3.90 (3H, s), 6.39 (1H, s), 6.89 (1H, t, J = 8.8 Hz), 6.98-7.01 (1H, m), 7.08-7.15 (5H, m). ESI-MS: m/z = 395 (M + H)$^+$ |
| 54 | | $^1$H-NMR (400 MHz, CDCl$_3$) δ: 2.26 (3H, d, J = 1.6 Hz), 2.31-2.45 (6H, m), 2.85-2.96 (3H, m), 3.82 (3H, s), 6.41 (1H, s), 6.84-6.90 (4H, m), 7.10 (1H, t, J = 8.0 Hz), 7.18-7.23 (2H, m). ESI-MS: m/z = 395 (M + H)$^+$ |
| 55 | | $^1$H-NMR (400 MHz, CDCl$_3$) δ: 2.30-2.45 (9H, m), 2.83 (1H, s), 2.86-2.97 (2H, m), 6.45 (1H, s), 7.10-7.20 (4H, m), 7.40-7.45 (2H, m), 7.59-7.64 (2H, m). ESI-MS: m/z = 372 (M + H)$^+$ |
| 56 | | $^1$H-NMR (400 MHz, CDCl$_3$) δ: 2.31-2.46 (6H, m), 2.84-2.96 (3H, m), 3.83 (3H, s), 6.53 (1H, s), 6.87-6.92 (2H, m), 7.15-7.21 (2H, m), 7.30-7.34 (2H, m), 7.57-7.61 (2H, m). ESI-MS: m/z = 425 (M + H)$^+$ |

Example 57 c-4-Hydroxy-4-(1-(4-methoxyphenyl)-5-(p-tolyl)-1H-pyrazol-3-yl)-cyclohexan-r-1-yl acetate

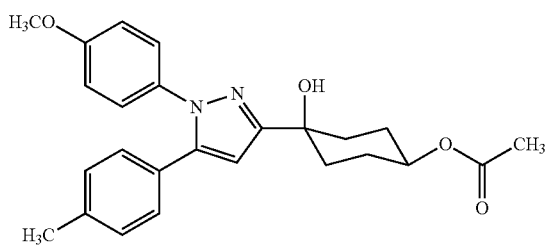

To a suspension of 1-(1-(4-methoxyphenyl)-5-(p-tolyl)-1H-pyrazol-3-yl)cyclohexan-cis-1,4-diol (Example 2-B) (500 mg, 1.32 mmol) in dichloromethane (4.4 mL), acetic anhydride (0.312 mL, 3.30 mmol), pyridine (0.267 mL, 3.30 mmol), and 4-dimethylaminopyridine (16.1 mg, 0.132 mmol) were added, and the obtained solution was stirred at room temperature for 45 minutes. Water was added to the reaction solution to quench the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (556 mg, 1.32 mmol, quant.) as an amorphous product.

$^1$H-NMR (400 MHz, CDCl$_3$) δ: 1.89-2.08 (11H, m), 2.34 (3H, s), 2.64 (1H, brs), 3.81 (3H, s), 4.80-4.88 (1H, m), 6.36 (1H, s), 6.85 (2H, d, J=8.8 Hz), 7.00 (4H, s), 7.20 (2H, d, J=8.8 Hz).

ESI-MS: m/z=421 (M+H)$^+$

Example 58

4-(4-Chloro-1-(4-methoxyphenyl)-5-(p-tolyl)-1H-pyrazol-3-yl)-c-4-hydroxy-cyclohexan-r-1-yl acetate

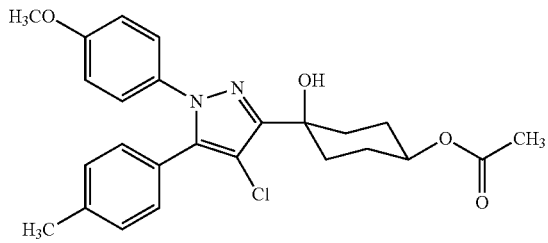

To a solution of c-4-hydroxy-4-(1-(4-methoxyphenyl)-5-(p-tolyl)-1H-pyrazol-3-yl)-cyclohexan-r-1-yl acetate (Example 57) (140 mg, 0.333 mmol) in acetonitrile (1.66 mL), N-chlorosuccinimide (49 mg, 0.366 mmol) was added. The obtained solution was stirred at 80° C. for 15 hours, and cooled to room temperature. Brine was added to the reaction solution, and the resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain the title compound (67 mg, 0.147 mmol, 44%) as a white solid.

$^1$H-NMR (400 MHz, CDCl$_3$) δ: 1.92-2.04 (6H, m), 2.28-2.36 (8H, m), 3.10 (1H, s), 3.79 (3H, s), 4.85-4.88 (1H, m), 6.80-6.82 (2H, m), 7.11-7.16 (6H, m).

Example 59

1-(4-Chloro-1-(4-methoxyphenyl)-5-(p-tolyl)-1H-pyrazol-3-yl)cyclohexan-cis-1,4-diol

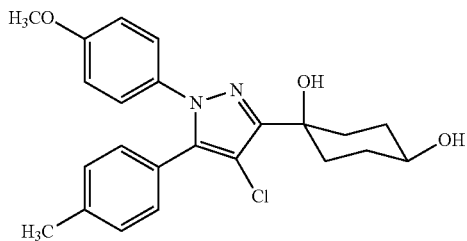

To a solution of 4-(4-chloro-1-(4-methoxyphenyl)-5-(p-tolyl)-1H-pyrazol-3-yl)-c-4-hydroxy-cyclohexan-r-1-yl acetate (Example 58) (67 mg, 0.147 mmol) in methanol (1.5 mL), potassium carbonate (102 mg, 0.736 mmol) was added, and the obtained solution was stirred at room temperature for 2 hours. Water was added to the reaction solution to quench the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (58 mg, 0.140 mmol, 95%) as a white solid.

$^1$H-NMR (400 MHz, CDCl$_3$) δ: 1.45 (1H, s), 1.83-2.05 (6H, m), 2.21-2.23 (2H, m), 2.36 (3H, s), 3.04 (1H, s), 3.76-3.79 (4H, m), 6.79-6.83 (2H, m), 7.11-7.16 (6H, m).

ESI-MS: m/z=395, 397 (M−OH)$^+$

Example 60 t-4-Fluoro-4-(1-(4-methoxyphenyl)-5-(p-tolyl)-1H-pyrazol-3-yl)-cyclohexan-r-1-ol

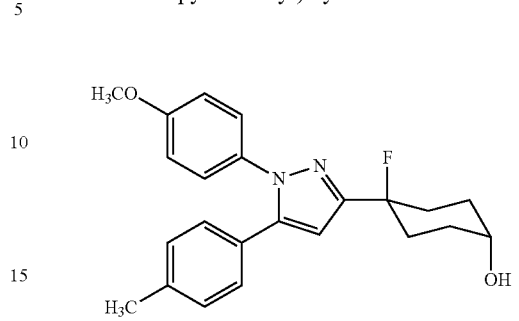

To a solution of c-4-hydroxy-4-(1-(4-methoxyphenyl)-5-p-tolyl-1H-pyrazol-3-yl)-cyclohexan-r-1-yl acetate (Example 57) (100 mg, 0.238 mmol) in dichloromethane (1.19 mL), Deoxofluor™ (48 μL, 0.262 mmol) was added, and the obtained solution was stirred at room temperature for 15 minutes. To the reaction solution, 1 M hydrochloric acid was added, and the resulting solution was extracted with chloroform. The organic layer was washed with brine, and then dried over anhydrous magnesium sulfate, and concentrated under reduced pressure to obtain the residue.

To a solution of the obtained residue in methanol (2.4 mL), potassium carbonate (164 mg, 1.18 mmol) was added, and the obtained solution was stirred at room temperature for 2 hours. Water was added to the reaction solution to quench the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (22.4 mg, 0.058 mmol, 25%) as a white solid.

$^1$H-NMR (400 MHz, CDCl$_3$) δ: 1.37 (1H, m), 1.72-1.77 (2H, m), 2.02-2.14 (4H, m), 2.34 (3H, s), 2.38-2.49 (2H, m), 3.81 (3H, s), 4.11 (1H, m), 6.52 (1H, m), 6.84 (2H, d, J=8.8 Hz), 7.22 (2H, d, J=8.8 Hz), 7.26 (4H, s).

ESI-MS: m/z=381 (M+H)$^+$

Example 61

4,4-Difluoro-1-(1-(4-methoxyphenyl)-5-(p-tolyl)-1H-pyrazol-3-yl)cyclohexanol

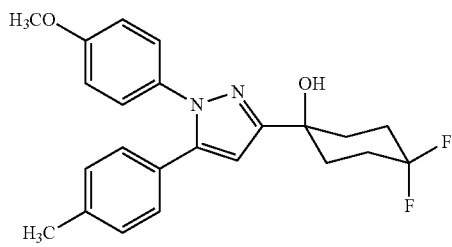

To a solution of 1-(1-(4-methoxyphenyl)-5-(p-tolyl)-1H-pyrazol-3-yl)-4-oxo-cyclohexan-1-yl acetate (Reference Example 81) (110 mg, 0.263 mmol) in dichloromethane (2.63 mL), (dimethylamino)sulfur trifluoride (DAST) (104 μL, 0.578 mmol) was added, and the obtained solution was stirred at room temperature for 2 hours. To the reaction solution, 1 M hydrochloric acid was added, and the resulting solution was extracted with chloroform. The organic layer was washed with brine, and then dried over anhydrous magnesium sulfate, and concentrated under reduced pressure to obtain the residue.

To a solution of the obtained residue in tetrahydrofuran (193 μL) and methanol (386 μL), 4 M aqueous sodium hydroxide solution (193 μL, 0.772 mmol) was added, and the obtained solution was stirred at room temperature for 6 hours. Water was added to the reaction solution to quench the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (41.0 mg, 0.103 mmol, 39%) as a white solid.

$^1$H-NMR (400 MHz, CDCl$_3$) δ: 2.01-2.31 (8H, m), 2.34 (3H, s), 2.77 (1H, s), 3.81 (3H, s), 6.37 (1H, s), 6.86 (2H, d, J=8.8 Hz), 7.10 (4H, s), 7.21 (2H, d, J=8.8 Hz).

ESI-MS: m/z=399 (M+H)$^+$

Example 62

1-(1-(4-Methoxyphenyl)-5-(p-tolyl)-1H-pyrazol-3-yl)-4-(trifluoromethyl)cyclohexan-cis-1,4-diol

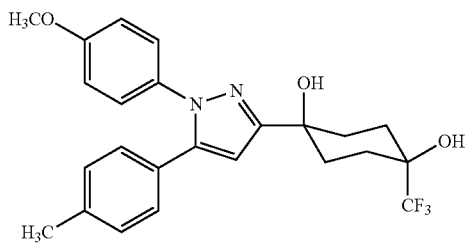

To a solution of 4-hydroxy-4-(1-(4-methoxyphenyl)-5-(p-tolyl)-1H-pyrazol-3-yl)cyclohexanone (Example 37) (620 mg, 1.65 mmol) in tetrahydrofuran (6.60 mL), (trifluoromethyl)trimethylsilane (535 μL, 3.62 mmol) was added at 0° C. Thereafter, tetra-n-butylammonium fluoride (TBAF, 1 M tetrahydrofuran solution) (362 μL, 0.36 mmol) was added dropwise thereto, and the obtained solution was stirred at room temperature for 6 hours. To the reaction solution, tetra-n-butylammonium fluoride (TBAF, 1 M tetrahydrofuran solution) (3.29 mL, 3.29 mmol) was added. The obtained mixture was stirred at room temperature for 1 hour, and then poured into 1 M hydrochloric acid. The reaction solution was extracted with diethyl ether. The organic layer was washed with brine, dried over anhydrous sodium sulfate, and concentrated under reduced pressure. The residue was purified by flash chromatography (silica gel, n-hexane/ethyl acetate) to obtain the title compound (410 mg, 0.92 mmol, 56%) as a white solid.

$^1$H-NMR (400 MHz, CDCl$_3$) δ: 1.60 (1H, s), 1.87-2.02 (4H, m), 2.09-2.02 (2H, m), 2.34-2.40 (6H, m), 3.82 (3H, s), 6.47 (1H, s), 6.86 (2H, d, J=8.8 Hz), 7.08-7.11 (4H, m), 7.20 (2H, d, J=8.8 Hz).

IR (KBr, cm$^{-1}$): 3402, 2954, 1517, 1463, 1305, 1250, 1249, 1179, 1121, 1056, 1024, 834.

ESI-MS: m/z=447 (M+H)$^+$

Example 63

4-Methoxy-1-(1-(4-methoxyphenyl)-5-(p-tolyl)-1H-pyrazol-3-yl)cyclohexanol

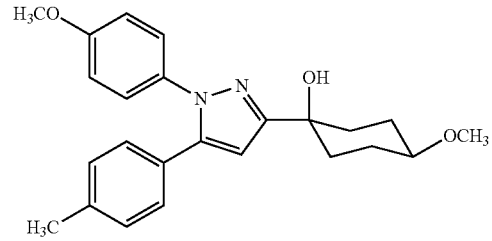

To a solution of c-4-methoxy-1-(1-(4-methoxyphenyl)-5-(p-tolyl)-1H-pyrazol-3-yl)-cyclohexan-r-1-yl acetate (Reference Example 79) (124 mg, 0.284 mmol) in methanol (2.8 mL), potassium carbonate (197 mg, 1.42 mmol) was added, and the obtained solution was stirred at room temperature for 18 hours. Water was added to the reaction solution to quench the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (102 mg, 0.260 mmol, 91%) as a white amorphous product.

$^1$H-NMR (400 MHz, CDCl$_3$) δ: 1.78-1.88 (2H, m), 1.90-1.99 (4H, m), 2.03-2.09 (2H, m), 2.33 (3H, s), 2.49 (1H, s), 3.24-3.32 (1H, m), 3.39 (3H, s), 3.81 (3H, s), 6.39 (1H, s), 6.85 (2H, d, J=8.8 Hz), 7.09 (4H, s), 7.20 (2H, d, J=8.8 Hz).

IR (KBr, cm$^{-1}$): 3425, 2937, 1516, 1443, 1369, 1300, 1249, 1171, 1099, 1030, 968, 834, 801.

ESI-MS: m/z=393 (M+H)$^+$

Example 64

4-Hydroxy-4-(1-(4-methoxyphenyl)-5-p-tolyl-1H-pyrazol-3-yl)-cis-cyclohexanecarboxylic acid

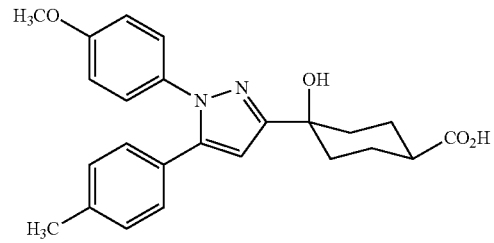

To a solution of c-4-hydroxy-4-(1-(4-methoxyphenyl)-5-(p-tolyl)-1H-pyrazol-3-yl)-cis-cyclohexan-r-1-carbaldehyde (Reference Example 82) (124.9 mg, 0.32 mmol) in t-butanol (2.4 ml), distilled water (0.8 ml) and 2-methyl-2-butene (101 μl, 0.96 mmol) were added, and the obtained solution was cooled in ice. At 0° C., sodium dihydrogen phosphate (42.1 mg, 0.35 mmol) and sodium chlorite (72.3 mg, 0.80 mmol) were added thereto, and the obtained mixture was stirred for 5 minutes. The mixture was warmed to room temperature, and stirred for 1 hour, and then cooled to 0° C. Thereafter, aqueous sodium thiosulfate solution was added thereto, and the resulting mixture was stirred. To the mixture, 1 M hydrochloric acid and ethyl acetate were added, and the resulting solution was extracted. The organic layer was washed with brine, dried over anhydrous sodium sulfate, and concentrated under reduced pressure. The residue was purified by flash chromatography (silica gel, n-hexane/ethyl acetate) to obtain the title compound (116.6 mg, 0.29 mmol, 93%) as a white solid.

$^1$H-NMR (400 MHz, CDCl$_3$) δ: 1.87-2.11 (9H, m), 2.33 (3H, s), 2.40-2.43 (1H, m), 3.81 (3H, s), 6.38 (1H, s), 6.84 (2H, d, J=9.2 Hz), 7.09-7.09 (4H, m), 7.20 (2H, d, J=9.2 Hz).

IR (KBr, cm$^{-1}$): 3523, 2928, 1706, 1517, 1252, 831.

ESI-MS: m/z=407 (M+H)$^+$

Example 65

4-(Hydroxymethyl)-4-(1-(4-methoxyphenyl)-5-p-tolyl-1H-pyrazol-3-yl)-trans-1,4-cyclohexanol (65-A)

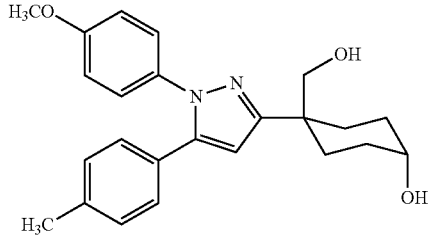

4-(Hydroxymethyl)-4-(1-(4-methoxyphenyl)-5-p-tolyl-1H-pyrazol-3-yl)-cis-1,4-cyclohexanol (65-B)

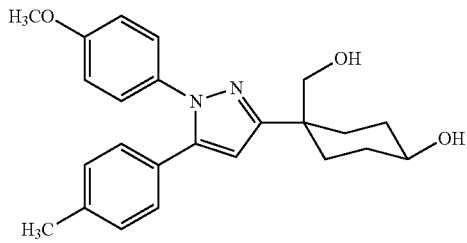

To a solution of 4-(benzyloxymethyl)-4-(1-(4-methoxyphenyl)-5-p-tolyl-1H-pyrazol-3-yl)cyclohexan-1-one (Reference Example 91) (387 mg, 0.804 mmol) in methanol (8.0 mL), sodium borohydride (30.4 mg, 0.804 mmol) was added. The obtained solution was stirred at room temperature for 1 hour, and then poured into 1 M hydrochloric acid. The reaction solution was extracted with ethyl acetate. The organic layer was washed with brine, dried over anhydrous sodium sulfate, and concentrated under reduced pressure to obtain the residue.

To a solution of the obtained residue in methanol (8.0 mL), under hydrogen atmosphere, 10% palladium carbon (86.0 mg, 0.080 mmol) was added, and the obtained solution was stirred at room temperature for 3 hours. The reaction solution was filtered through Celite, and concentrated under reduced pressure. The residue was purified by flash chromatography (amine silica gel, n-hexane/ethyl acetate) to obtain the title compound 65-A (51.6 mg, 0.131 mmol, 16%) as a white solid, and the title compound 65-B (164 mg, 0.418 mmol, 52%) as a white amorphous product.

65-A: $^1$H-NMR (400 MHz, CDCl$_3$) δ: 1.43 (1H, brs), 1.54-1.67 (2H, m), 1.83-1.91 (4H, m), 2.00-2.08 (2H, m), 2.34 (3H, s), 3.24-3.33 (1H, m), 3.78-3.86 (6H, m), 6.32 (1H, s), 6.84 (2H, d, J=8.8 Hz), 7.10 (4H, s), 7.19 (2H, d, J=8.8 Hz).

ESI-MS: m/z=393 (M+H)$^+$

65-B: $^1$H-NMR (400 MHz, CDCl$_3$) δ: 1.39 (1H, d, J=4.8 Hz), 1.46-1.60 (4H, m), 1.85-1.95 (2H, m), 2.33-2.40 (5H, m), 2.71 (1H, t, J=6.4 Hz), 3.55 (2H, d, J=6.4 Hz), 3.71-3.83 (4H, m), 6.37 (1H, s), 6.85 (2H, d, J=8.8 Hz), 7.10 (4H, s), 7.20 (2H, d, J=8.8 Hz).

ESI-MS: m/z=393 (M+H)$^+$

Example 66

4-(4,5-Bis(4-methoxyphenyl)oxazol-2-yl)-4-hydroxycyclohexanone

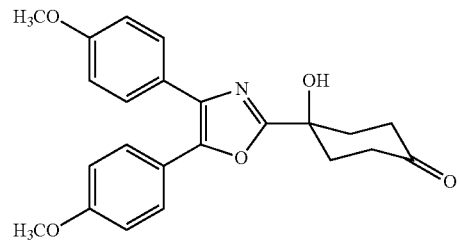

To a solution of 8-(4,5-bis(4-methoxyphenyl)oxazol-2-yl)-1,4-dioxaspiro[4.5]decan-8-ol (Reference Example 92) (781 mg, 1.78 mmol) in tetrahydrofuran (4.5 mL), 6 M hydrochloric acid (9.0 mL) was added at 0° C., and the obtained solution was stirred at room temperature for 2 hours. The reaction solution was cooled to 0° C., and alkalified by addition of 10% aqueous sodium hydroxide solution and saturated sodium bicarbonate solution. The resulting solution was extracted with ethyl acetate. The organic layer was dried over anhydrous magnesium sulfate, and concentrated under reduced pressure. The residue was purified by recrystallization (ethyl acetate/n-hexane) to obtain the title compound (445 mg, 1.13 mmol, 63%) as a pale yellow solid.

$^1$H-NMR (400 MHz, CDCl$_3$) δ: 2.32-2.54 (6H, m), 2.81-2.92 (2H, m), 3.17 (1H, m), 3.84 (6H, s), 6.90 (2H, d, J=8.8 Hz), 6.91 (2H, d, J=8.8 Hz), 7.49 (2H, d, J=8.8 Hz), 7.56 (2H, d, J=8.8 Hz).

ESI-MS: m/z=394 (M+H)$^+$

Example 67

4-(4,5-Bis(4-methoxyphenyl)oxazol-2-yl)cyclohexan-trans-1,4-diol (67-A)

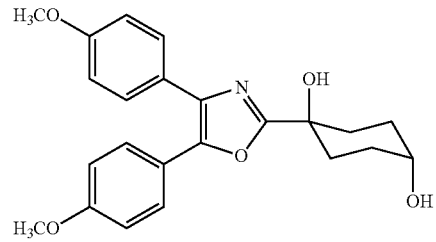

4-(4,5-Bis(4-methoxyphenyl)oxazol-2-yl)cyclohexan-cis-1,4-diol (67-B)

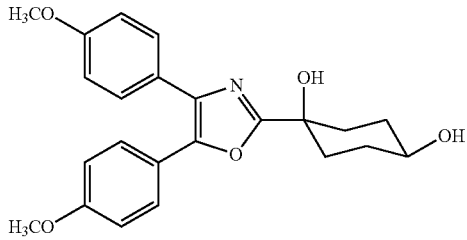

To a solution of 4-hydroxy-4-(4,5-bis(4-methoxyphenyl)oxazol-2-yl)cyclohexan-1-one (Example 66) (395 mg, 1.00 mmol) in methanol (20 mL), sodium borohydride (47 mg, 1.24 mmol) was added, and the obtained solution was stirred at room temperature for 16 hours. The reaction solution was concentrated under reduced pressure, and distilled water was added to the residue. The resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain the title compound 67-A (73 mg, 0.18 mmol, 18%) as a white solid, and the title compound 67-B (207 mg, 0.523 mmol, 52%) as a white solid.

67-A: $^1$H-NMR (400 MHz, CDCl$_3$) δ: 1.63-1.75 (2H, m), 1.78-1.88 (2H, m), 2.01-2.12 (2H, m), 2.44-2.53 (2H, m), 2.67 (1H, s), 4.00-4.07 (1H, m), 6.89 (2H, d, J=8.8 Hz), 6.90 (2H, d, J=8.8 Hz), 7.51 (2H, d, J=8.8 Hz), 7.57 (2H, d, J=8.8 Hz).

IR (KBr, cm$^{-1}$): 3356, 1613, 1600, 1520, 1503, 1254, 1182, 1033, 999, 966, 834.

ESI-MS: m/z=396 (M+H)$^+$

67-B: $^1$H-NMR (400 MHz, CDCl$_3$) δ: 1.49 (1H, brs), 1.78-2.13 (8H, m), 2.76 (1H, s), 3.72-3.78 (1H, m), 3.83 (6H, s), 6.89 (2H, d, J=8.8 Hz), 6.90 (2H, d, J=8.8 Hz), 7.49 (2H, d, J=8.8 Hz), 7.55 (2H, d, J=8.8 Hz).

IR (KBr, cm$^{-1}$): 3364, 1615, 1599, 1520, 1500, 1302, 1252, 1176, 1069, 1053, 1028, 965, 833.

ESI-MS: m/z=396 (M+H)$^+$

Example 68

4-Hydroxy-4-(4-(4-methoxyphenyl)-5-(p-tolyl)thiazol-2-yl)cyclohexan-1-one

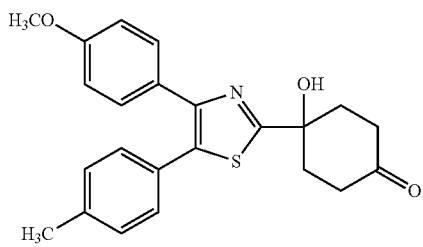

To a solution of 8-(4-(4-methoxyphenyl)-5-(p-tolyl)thiazol-2-yl)-1,4-dioxaspiro[4.5]decan-8-ol (Reference Example 96) (469 mg, 1.07 mmol) in tetrahydrofuran (5.4 mL), 6 M hydrochloric acid (5.4 mL) was added at 0° C., and the obtained solution was stirred at room temperature for 14 hours. The reaction solution was basified by pouring it into saturated aqueous sodium hydrogen carbonate solution, and the resulting mixture was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (352 mg, 0.895 mmol, 83%) as a white solid.

$^1$H-NMR (400 MHz, CDCl$_3$) δ: 2.33-2.51 (6H, m), 2.37 (3H, s), 2.86-2.95 (2H, m), 3.50 (1H, s), 3.81 (3H, s), 6.81-6.84 (2H, m), 7.14 (2H, d, J=8.0 Hz), 7.24 (2H, d, J=8.0 Hz), 7.44-7.48 (2H, m).

ESI-MS: m/z=394 (M+H)$^+$

Example 69

1-(4-(4-Methoxyphenyl)-5-(p-tolyl)thiazol-2-yl)cyclohexan-trans-1,4-diol (69-A)

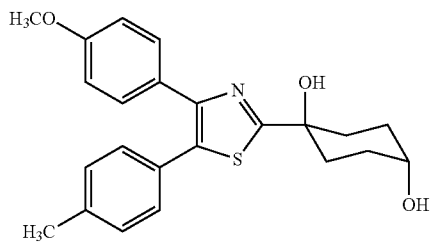

1-(4-(4-Methoxyphenyl)-5-p-tolylthiazol-2-yl)cyclohexan-cis-1,4-diol (69-B)

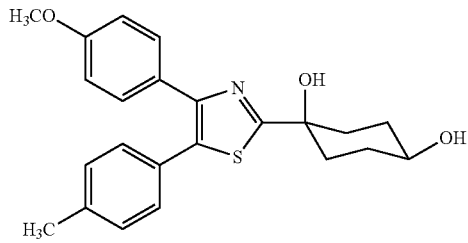

To a solution of 4-hydroxy-4-(4-(4-methoxyphenyl)-5-(p-tolyl)thiazol-2-yl)cyclohexan-1-one (Example 68) (186 mg, 0.471 mmol) in methanol (4.7 mL), sodium borohydride (36 mg, 0.943 mmol) was added, and the obtained solution was stirred at room temperature for 1 hour. The reaction solution was concentrated under reduced pressure, and then dissolved into ethyl acetate, and washed with distilled water and brine. The organic layer was dried over anhydrous sodium sulfate, and concentrated under reduced pressure. The residue was purified by flash chromatography (silica gel, n-hexane/ethyl acetate) to obtain the title compound 69-A (42 mg, 0.106 mmol, 23%) as a white solid, and the title compound 69-B (136 mg, 0.344 mmol, 73%) as a white solid.

69-A: $^1$H-NMR (400 MHz, CDCl$_3$) δ: 1.53-1.57 (1H, m), 1.76-1.87 (4H, m), 2.05-2.12 (2H, m), 2.35-2.42 (2H, m), 2.36 (3H, s), 3.15 (1H, br), 3.80 (3H, s), 4.10-4.14 (1H, m), 6.80-6.84 (2H, m), 7.13 (2H, d, J=8.0 Hz), 7.24 (2H, d, J=8.0 Hz), 7.45-7.49 (2H, m).

IR (KBr, cm$^{-1}$): 3409, 2923, 1613, 1515, 1252, 1179, 1004, 815.

ESI-MS: m/z=396 (M+H)$^+$

69-B: $^1$H-NMR (400 MHz, CDCl$_3$) δ: 1.48 (1H, d, J=4.8 Hz), 1.82-1.89 (2H, m), 1.95-2.01 (2H, m), 2.05-2.09 (4H, m), 2.36 (3H, s), 3.01 (1H, s), 3.76-3.82 (1H, m), 3.80 (3H, s), 6.80-6.83 (2H, m), 7.13 (2H, d, J=8.0 Hz), 7.22 (2H, d, J=8.0 Hz), 7.43-7.47 (2H, m).

IR (KBr, cm$^{-1}$): 3418, 2938, 1611, 1515, 1249, 1177, 1058, 816.

ESI-MS: m/z=396 (M+H)$^+$

Example 70

1-(4-(4-Methoxyphenyl)-5-p-tolylthiazol-2-yl)-4-(trifluoromethyl)cyclohexan-trans-1,4-diol (70-A)

1-(4-(4-Methoxyphenyl)-5-(p-tolyl)thiazol-2-yl)-4-(trifluoromethyl)cyclohexan-cis-1,4-diol (70-B)

To a solution of 4-hydroxy-4-(4-(4-methoxyphenyl)-5-p-tolylthiazol-2-yl)cyclohexan-1-one (Example 68) (199 mg, 0.506 mmol) and Ruppert's reagent (0.187 mL, 1.26 mmol) in tetrahydrofuran (2.5 mL), 1.0 M tetrabutylammonium fluoride/tetrahydrofuran solution (0.051 mL, 0.051 mmol) was added at room temperature, and the obtained solution was stirred for 10 minutes. The reaction solution was concentrated under reduced pressure, and dissolved into tetrahydrofuran (3.0 mL). Distilled water (0.2 mL) and 1.0 M tetrabutylammonium fluoride/tetrahydrofuran solution (1.02 mL, 1.02 mmol) were added thereto, and the resulting mixture was stirred at room temperature for 30 minutes. Distilled water was added to the reaction solution, and the resulting solution was extracted with ethyl acetate, followed by washing with brine. The organic layer was dried over anhydrous sodium sulfate, and concentrated under reduced pressure. The residue was purified by flash chromatography (silica gel, n-hexane/ethyl acetate) to obtain the title compound 70-A (70 mg, 0.151 mmol, 30%) as a white solid, and the title compound 70-A (132 mg, 0.285 mmol, 56%) as a white solid.

70-A: $^1$H-NMR (400 MHz, CDCl$_3$) δ: 1.79-1.84 (2H, m), 1.90 (1H, s), 1.96-2.01 (2H, m), 2.21-2.33 (4H, m), 2.37 (3H, s), 3.28 (1H, s), 3.80 (3H, s), 6.80-6.84 (2H, m), 7.13 (2H, d, J=8.0 Hz), 7.23 (2H, d, J=8.0 Hz), 7.44-7.48 (2H, m).

IR (KBr, cm$^{-1}$): 3460, 2940, 1610, 1515, 1494, 1442, 1310, 1245, 1175, 1035, 1005, 837, 813

ESI-MS: m/z=464 (M+H)$^+$

70-B: $^1$H-NMR (400 MHz, CDCl$_3$) δ: 1.90-1.96 (2H, m), 1.97 (1H, br), 2.16-2.23 (2H, m), 2.28-2.36 (4H, m), 2.37 (3H, s), 2.81 (1H, br), 3.80 (3H, s), 6.80-6.83 (2H, m), 7.14 (2H, d, J=8.0 Hz), 7.26 (2H, d, J=8.0 Hz), 7.44-7.48 (2H, m).

IR (KBr, cm$^{-1}$): 3419, 2940, 1611, 1515, 1443, 1290, 1250, 1175, 1120, 1066, 993, 837, 814

ESI-MS: m/z=464 (M+H)$^+$

Example 71

Ethyl 4-hydroxy-4-(1-(4-methoxyphenyl)-5-p-tolyl-1H-pyrazol-3-yl)-cis-cyclohexanecarboxylate

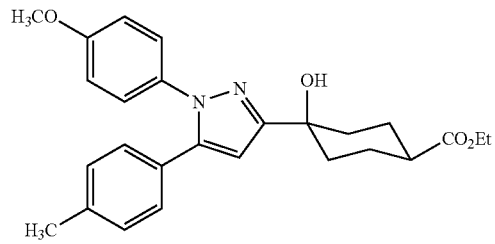

To a solution of 4-hydroxy-4-(1-(4-methoxyphenyl)-5-p-tolyl-1H-pyrazol-3-yl)-cis-cyclohexanecarboxylic acid (Example 64) (41.6 mg, 0.10 mmol) in DMF (1.0 ml), potassium carbonate (41.4 mg, 0.3 mmol) and ethyl iodide (24.8 μl, 0.3 mmol) were added, and the obtained solution was stirred for 2 hours. Brine was added to the reaction solution, and the resulting solution was extracted with ethyl acetate. The organic layer was washed with brine, dried over anhydrous sodium sulfate, and concentrated under reduced pressure. The residue was purified by flash column chromatography (silica gel, n-hexane/ethyl acetate) to obtain the title compound (44.1 mg, 0.10 mmol, 97%) as a white amorphous product.

$^1$H-NMR (400 MHz, CDCl$_3$) δ: 1.27 (3H, t, J=6.8 Hz), 1.85-2.09 (8H, m), 2.33 (3H, s), 2.34-2.41 (1H, m), 2.59 (1H, s), 3.80 (3H, s), 4.15 (2H, q, J=6.8 Hz), 6.38 (1H, s), 6.84 (2H, d, J=8.8 Hz), 7.09-7.09 (4H, m), 7.20 (2H, d, J=8.8 Hz).

ESI-MS: m/z=435 (M+H)$^+$

The compounds of the following Comparative Examples 1 to 25 were prepared by the same procedure as in the above Examples 2 to 6.

TABLE 9-1

| Comparative Example | Structural Formula | Compound Data |
|---|---|---|
| 1 | H$_3$CO-phenyl-pyrazol(2-CH$_3$-phenyl)-cyclohexane(OH)(OH) | $^1$H-NMR (400 MHz, CDCl$_3$) δ: 1.67-1.73 (3H, m), 1.80-1.86 (2H, m), 2.00 (3H, s), 2.05-2.12 (2H, m), 2.33-2.40 (2H, m), 2.59 (1H, s), 3.76 (3H, s), 4.03-4.06 (1H, m), 6.35 (1H, s), 6.72 (2H, d, J = 8.8 Hz), 7.11-7.21 (6H, m). ESI-MS: m/z = 379 (M + H)$^+$ |

TABLE 9-1-continued

| Comparative Example | Structural Formula | Compound Data |
|---|---|---|
| 2 | (4-methoxyphenyl at N1, 2-methylphenyl at C5, 1,4-dihydroxycyclohexyl at C3 of pyrazole) | $^1$H-NMR (400 MHz, CDCl$_3$) δ: 1.85-1.99 (10H, m), 2.06-2.09 (2H, m), 2.66 (1H, s), 3.75-3.75 (4H, m), 6.28 (1H, s), 6.75 (2H, d, J = 9.2 Hz), 7.12 (2H, d, J = 9.2 Hz), 7.14-7.20 (3H, m), 7.24-7.28 (1H, m). IR (KBr, cm$^{-1}$): 3326, 2939, 1516, 1249, 1069, 834. ESI-MS: m/z = 361 (M − OH)$^+$, 379 (M + H)$^+$ |
| 3 | (4-methoxyphenyl at N1, 4-(methylsulfonyl)phenyl at C5, 1,4-dihydroxycyclohexyl at C3 of pyrazole) | $^1$H-NMR (400 MHz, CDCl$_3$) δ: 1.63-1.83 (5H, m), 2.03-2.12 (2H, m), 2.32-2.39 (2H, m), 2.58 (1H, s), 3.07 (3H, s), 3.83 (3H, s), 4.04-4.06 (1H, m), 6.57 (1H, s), 6.88 (2H, d, J = 8.8 Hz), 7.19 (2H, d, J = 8.8 Hz), 7.40 (2H, d, J = 8.8 Hz), 7.85 (2H, d, J = 8.8 Hz). ESI-MS: m/z = 443 (M + H)$^+$ |
| 4 | (4-methoxyphenyl at N1, 4-(methylsulfonyl)phenyl at C5, 1,4-dihydroxycyclohexyl at C3 of pyrazole) | $^1$H-NMR (400 MHz, CDCl$_3$) δ: 1.80-2.00 (9H, m), 3.06 (3H, s), 3.71-3.80 (1H, m), 3.82 (3H, s), 6.53 (1H, s), 6.88 (2H, d, J = 8.8 Hz), 7.17 (2H, d, J = 8.8 Hz), 7.39 (2H, d, J = 8.4 Hz), 7.85 (2H, d, J = 8.4 Hz). ESI-MS: m/z = 443 (M + H)$^+$ |

TABLE 9-2

| Comparative Example | Structural Formula | Compound Data |
|---|---|---|
| 5 | (4-fluorophenyl at N1, 4-chlorophenyl at C5, 1,4-dihydroxycyclohexyl at C3 of pyrazole) | $^1$H-NMR (400 MHz, CDCl$_3$) δ: 1.34 (1H, brs), 1.64-1.73 (2H, m), 1.76-1.84 (2H, m), 2.03-2.12 (2H, m), 2.30-2.40 (2H, m), 2.45 (1H, brs), 4.03-4.10 (1H, m), 6.48 (1H, s), 7.02-7.08 (2H, m), 7.12-7.17 (2H, m), 7.23-7.32 (4H, m). ESI-MS: m/z = 387 (M + H)$^+$ |
| 6 | (4-fluorophenyl at N1, 4-chlorophenyl at C5, 1,4-dihydroxycyclohexyl at C3 of pyrazole) | $^1$H-NMR (400 MHz, CDCl$_3$) δ: 1.45 (1H, d, J = 5.2 Hz), 1.80-2.09 (8H, m), 2.45 (1H, s), 3.70-3.80 (1H, m), 6.43 (1H, s), 7.01-7.08 (2H, m), 7.11-7.16 (2H, m), 7.22-7.31 (4H, m). ESI-MS: m/z = 387 (M + H)$^+$ |

TABLE 9-2-continued

| Comparative Example | Structural Formula | Compound Data |
|---|---|---|
| 7 | (2,4-dichlorophenyl / 4-chlorophenyl pyrazole with cyclohexane-1,4-diol) | $^1$H-NMR (400 MHz, CDCl$_3$) δ: 1.34 (1H, brs), 1.63-1.71 (2H, m), 1.77-1.84 (2H, m), 2.03-2.11 (2H, m), 2.32-2.40 (3H, m), 4.01-4.08 (1H, m), 6.53 (1H, s), 7.09-7.12 (2H, m), 7.24-7.27 (2H, m), 7.32 (1H, dd, J = 8.4, 2.0 Hz), 7.36 (1H, d, J = 8.4 Hz), 7.46 (1H, d, J = 2.0 Hz).<br>ESI-MS: m/z = 437 (M + H)$^+$ |
| 8 | (2,4-dichlorophenyl / 4-chlorophenyl pyrazole with cyclohexane-1,4-diol) | $^1$H-NMR (400 MHz, CDCl$_3$) δ: 1.44 (1H, d, J = 4.8 Hz), 1.79-2.09 (8H, m), 2.37 (1H, s), 3.70-3.80 (1H, m), 6.49 (1H, s), 7.08-7.11 (2H, m), 7.24-7.27 (2H, m), 7.32 (1H, dd, J = 8.4, 2.0 Hz), 7.35 (1H, d, J = 8.4 Hz), 7.45 (1H, d, J = 2.0 Hz).<br>ESI-MS: m/z = 437 (M + H)$^+$ |
| 9 | (4-methoxyphenyl / 3-methylphenyl pyrazole with cyclohexane-1,4-diol) | $^1$H-NMR (400 MHz, CDCl$_3$) δ: 1.34 (1H, d, J = 3.6 Hz), 1.64-1.73 (2H, m), 1.77-1.84 (2H, m), 2.04-2.12 (2H, m), 2.30 (3H, s), 2.31-2.40 (2H, m), 2.56 (1H, s), 3.81 (3H, s), 4.02-4.08 (1H, m), 6.45 (1H, s), 6.85 (2H, d, J = 9.2 Hz), 6.93-6.97 (1H, m), 7.09-7.18 (3H, m), 7.22 (2H, d, J = 9.2 Hz).<br>ESI-MS: m/z = 379 (M + H)$^+$ |

TABLE 9-3

| Comparative Example | Structural Formula | Compound Data |
|---|---|---|
| 10 | (4-methoxyphenyl / 3-methylphenyl pyrazole with cyclohexane-1,4-diol) | $^1$H-NMR (400 MHz, CDCl$_3$) δ: 1.43 (1H, d, J = 4.8 Hz), 1.83-2.00 (6H, m), 2.03-2.09 (2H, m), 2.29 (3H, s), 2.56 (1H, s), 3.70-3.78 (1H, m), 3.81 (3H, s), 6.39 (1H, s), 6.84 (2H, d, J = 8.8 Hz), 6.92-6.96 (1H, m), 7.08-7.18 (3H, m), 7.20 (2H, d, J = 8.8 Hz).<br>ESI-MS: m/z = 379 (M + H)$^+$ |
| 11 | (4-fluorophenyl / 4-methylphenyl pyrazole with cyclohexane-1,4-diol) | $^1$H-NMR (400 MHz, CDCl$_3$) δ: 1.36 (1H, brs), 1.64-1.72 (2H, m), 1.77-1.83 (2H, m), 2.04-2.12 (2H, m), 2.32-2.39 (2H, m), 2.35 (3H, s), 2.51 (1H, s), 4.03-4.08 (1H, m), 6.44 (1H, s), 6.99-7.05 (2H, m), 7.09 (2H, d, J = 8.4 Hz), 7.12 (2H, d, J = 8.4 Hz), 7.24-7.30 (2H, m).<br>IR (KBr, cm$^{-1}$): 3342, 2921, 1516, 1439, 1368, 1227, 1196, 1156, 1005, 840, 810.<br>ESI-MS: m/z = 367 (M + H)$^+$ |

TABLE 9-3-continued

| Comparative Example | Structural Formula | Compound Data |
|---|---|---|
| 12 | 4-F-phenyl, 4-methylphenyl pyrazole with cyclohexanediol | $^1$H-NMR (400 MHz, CDCl$_3$) δ: 1.50 (1H, brs), 1.80-1.99 (6H, m), 2.02-2.08 (2H, m), 2.35 (3H, s), 2.54 (1H, s), 3.71-3.78 (1H, m), 6.39 (1H, s), 6.99-7.05 (2H, m), 7.08 (2H, d, J = 8.4 Hz), 7.11 (2H, d, J = 8.4 Hz), 7.23-7.28 (2H, m). IR (KBr, cm$^{-1}$): 3374, 2938, 2876, 1515, 1436, 1416, 1362, 1238, 1192, 1167, 1111, 1092, 1064, 1018, 973, 886, 843, 799. ESI-MS: m/z = 349 (M − OH)$^+$ |
| 13 | 4-methoxyphenyl, 4-F-phenyl pyrazole with cyclohexanediol | $^1$H-NMR (400 MHz, CDCl$_3$) δ: 1.54 (1H, brs), 1.64-1.72 (2H, m), 1.77-1.84 (2H, m), 2.04-2.12 (2H, m), 2.32-2.39 (2H, m), 2.52 (1H, s), 3.82 (3H, s), 4.03-4.08 (1H, m), 6.44 (1H, s), 6.84-6.88 (2H, m), 6.96-7.02 (2H, m), 7.16-7.21 (4H, m). IR (KBr, cm$^{-1}$): 3355, 2931, 1516, 1249, 1003, 830. ESI-MS: m/z = 383 (M + H)$^+$ |

TABLE 9-4

| Comparative Example | Structural Formula | Compound Data |
|---|---|---|
| 14 | 4-methoxyphenyl, 4-F-phenyl pyrazole with cyclohexanediol | $^1$H-NMR (400 MHz, CDCl$_3$) δ: 1.45 (1H, brs), 1.80-2.00 (6H, m), 2.02-2.09 (2H, m), 2.53 (1H, s), 3.70-3.78 (1H, m), 3.81 (3H, s), 6.39 (1H, s), 6.83-6.88 (2H, m), 6.96-7.01 (2H, m), 7.16-7.20 (4H, m). IR (KBr, cm-1): 3412, 2937, 1609, 1517, 1444, 1300, 1251, 1159, 1066, 971, 839. ESI-MS: m/z = 365 (M − OH)$^+$ |
| 15 | 4-Cl-phenyl, 4-F-phenyl pyrazole with cyclohexanediol | $^1$H-NMR (400 MHz, CDCl$_3$) δ: 1.42 (1H, brs), 1.63-1.72 (2H, m), 1.76-1.83 (2H, m), 2.03-2.11 (2H, m), 2.31-2.38 (2H, m), 2.50 (1H, s), 4.04-4.09 (1H, m), 6.46 (1H, s), 7.00-7.05 (2H, m), 7.17-7.22 (4H, m), 7.29-7.32 (2H, m). IR (KBr, cm$^{-1}$): 3366, 2936, 1499, 1362, 1231, 1002, 840. ESI-MS: m/z = 387 (M + H)$^+$ |
| 16 | 4-Cl-phenyl, 4-F-phenyl pyrazole with cyclohexanediol | $^1$H-NMR (400 MHz, CDCl$_3$) δ: 1.46 (1H, brs), 1.80-1.99 (6H, m), 2.02-2.08 (2H, m), 2.47 (1H, s), 3.70-3.79 (1H, m), 6.41 (1H, s), 7.00-7.05 (2H, m), 7.17-7.22 (4H, m), 7.28-7.32 (2H, m). IR (KBr, cm$^{-1}$): 3459, 2937, 1602, 1500, 1374, 1231, 1071, 963. ESI-MS: m/z = 369 (M − OH)$^+$ |

TABLE 9-4-continued

| Comparative Example | Structural Formula | Compound Data |
|---|---|---|
| 17 | (4-F-C6H4)-pyrazole-(4-F-C6H4), cyclohexane-diol structure | ¹H-NMR (400 MHz, CDCl₃) δ: 1.45 (1H, brs), 1.64-1.72 (2H, m), 1.77-1.83 (2H, m), 2.03-2.12 (2H, m), 2.31-2.39 (2H, m), 2.51 (1H, br), 4.03-4.08 (1H, m), 6.46 (1H, s), 6.98-7.06 (4H, m), 7.11-7.20 (2H, m), 7.23-7.26 (2H, m). IR (KBr, cm⁻¹): 3399, 2933, 1609, 1515, 1444, 1368, 1228, 1159, 1073, 999, 840, 815. ESI-MS: m/z = 371 (M + H)⁺ |

TABLE 9-5

| Comparative Example | Structural Formula | Compound Data |
|---|---|---|
| 18 | (4-F-C6H4)-pyrazole-(4-F-C6H4), cyclohexane-diol structure | ¹H-NMR (400 MHz, CDCl₃) δ: 1.47 (1H, brs), 1.80-2.00 (6H, m), 2.02-2.07 (2H, m), 2.48 (1H, s), 3.71-3.79 (1H, m), 6.41 (1H, s), 6.98-7.06 (4H, m), 7.15-7.20 (2H, m), 7.22-7.26 (2H, m). IR (KBr, cm⁻¹): 3369, 2941, 1609, 1515, 1236, 1159, 1066, 973, 841. ESI-MS: m/z = 353 (M − OH)⁺ |
| 19 | phenyl-pyrazole-(4-F-C6H4), cyclohexane-diol structure | ¹H-NMR (400 MHz, CDCl₃) δ: 1.40 (1H, brs), 1.65-1.72 (2H, m), 1.78-1.84 (2H, m), 2.04-2.12 (2H, m), 2.32-2.40 (2H, m), 2.55 (1H, s), 4.04-4.08 (1H, m), 6.46 (1H, s), 6.97-7.02 (2H, m), 7.17-7.22 (2H, m), 7.27-7.36 (5H, m). IR (KBr, cm⁻¹): 3361, 2932, 1604, 1502, 1438, 1363, 1231, 1000, 812, 766. ESI-MS: m/z = 353 (M + H)⁺ |
| 20 | phenyl-pyrazole-(4-F-C6H4), cyclohexane-diol structure | ¹H-NMR (400 MHz, CDCl₃) δ: 1.45-1.46 (1H, m), 1.81-2.01 (6H, m), 2.02-2.09 (2H, m), 2.54 (1H, s), 3.71-3.79 (1H, m), 6.41 (1H, s), 6.97-7.02 (2H, m), 7.16-7.21 (2H, m), 7.25-7.28 (2H, m), 7.30-7.36 (3H, m). IR (KBr, cm⁻¹): 3349, 2941, 1601, 1502, 1436, 1359, 1232, 1066, 834. ESI-MS: m/z = 335 (M − OH)⁺ |
| 21 | (4-CH3-C6H4)-pyrazole-(4-F-C6H4), cyclohexane-diol structure | ¹H-NMR (400 MHz, CDCl₃) δ: 1.38 (1H, brs), 1.64-1.72 (2H, m), 1.77-1.84 (2H, m), 2.04-2.12 (2H, m), 2.32-2.39 (2H, m), 2.36 (3H, s), 2.56 (1H, s), 4.03-4.08 (1H, m), 6.44 (1H, s), 6.96-7.02 (2H, m), 7.12-7.21 (6H, m). IR (KBr, cm⁻¹): 3363, 2926, 1613, 1509, 1440, 1364, 1231, 1001, 818. ESI-MS: m/z = 367 (M + H)⁺ |

TABLE 9-6

| Comparative Example | Structural Formula | Compound Data |
|---|---|---|
| 22 | (4-methylphenyl / 4-fluorophenyl pyrazole cyclohexanediol structure) | $^1$H-NMR (400 MHz, CDCl$_3$) δ: 1.43 (1H, brs), 1.65-1.73 (2H, m), 1.76-1.83 (2H, m), 2.04-2.12 (2H, m), 2.32-2.39 (2H, m), 2.38 (3H, s), 2.48 (1H, br), 3.06 (3H, s), 4.05-4.09 (1H, m), 6.49 (1H, s), 7.12 (2H, d, J = 8.0 Hz), 7.16 (2H, d, J = 8.0 Hz), 7.50 (2H, d, J = 8.4 Hz), 7.88 (2H, d, J = 8.4 Hz).<br>IR (KBr, cm$^{-1}$): 3422, 2930, 1594, 1504, 1364, 1306, 1150, 958, 781.<br>ESI-MS: m/z = 427 (M + H)$^+$ |
| 23 | (methylsulfonylphenyl / p-tolyl pyrazole cyclohexanediol) | $^1$H-NMR (400 MHz, CDCl$_3$) δ: 1.44-1.46 (1H, m), 1.84-2.00 (6H, m), 2.03-2.08 (2H, m), 2.38 (3H, s), 2.46 (1H, s), 3.05 (3H, s), 3.74-3.78 (1H, m), 6.44 (1H, s), 7.11 (2H, d, J = 8.0 Hz), 7.17 (2H, d, J = 8.0 Hz), 7.49 (2H, d, J = 8.4 Hz), 7.88 (2H, d, J = 8.4 Hz).<br>IR (KBr, cm$^{-1}$): 3402, 2932, 1594, 1505, 1364, 1305, 1153, 961, 780.<br>ESI-MS: m/z = 409 (M − OH)$^+$ |
| 24 | (4-methoxyphenyl / 2-methoxypyridinyl pyrazole cyclohexanediol) | $^1$H-NMR (400 MHz, CDCl$_3$) δ: 1.37 (1H, s), 1.67-1.72 (2H, m), 1.79-1.85 (2H, m), 2.05-2.09 (2H, m), 2.33-2.37 (2H, m), 2.54 (1H, s), 3.67 (3H, s), 3.79 (3H, s), 4.06-4.10 (1H, m), 6.50 (1H, s), 6.82 (2H, d, J = 8.8 Hz), 6.87 (1H, dd, J = 5.2, 7.2 Hz), 7.17 (2H, d, J = 8.8 Hz), 7.46 (1H, d, J = 2.0, 7.2 Hz), 8.15 (1H, d, J = 2.0, 5.2 Hz).<br>ESI-MS: m/z = 396 (M + H)$^+$ |
| 25 | (4-methoxyphenyl / 2-methoxypyridinyl pyrazole cyclohexanediol isomer) | $^1$H-NMR (400 MHz, CDCl$_3$) δ: 1.44-1.46 (1H, m), 1.87-1.97 (6H, m), 2.05-2.06 (2H, m), 2.52 (1H, s), 3.67 (3H, s), 3.74-3.79 (4H, s), 6.45 (1H, s), 6.82 (2H, d, J = 8.8 Hz), 6.87 (1H, dd, J = 5.2, 7.2 Hz), 7.17 (2H, d, J = 8.8 Hz), 7.45 (1H, d, J = 2.0, 7.2 Hz), 8.14 (1H, d, J = 2.0, 5.2 Hz).<br>ESI-MS: m/z = 396 (M + H)$^+$ |

Comparative Example 26 c-4-Hydroxy-1-(1-(4-methoxyphenyl)-5-(p-tolyl)-1H-pyrazol-3-yl)-cyclohexan-r-1-yl acetate

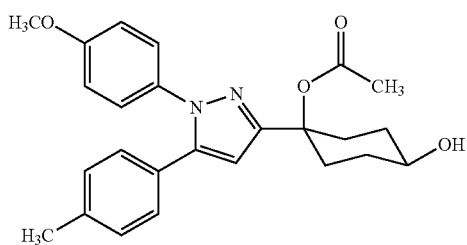

To a solution of 1-(1-(4-methoxyphenyl)-5-(p-tolyl)-1H-pyrazol-3-yl)-cyclohexan-cis-1,4-diyl diacetate (Reference Example 78) (297 mg, 0.642 mmol) in methanol (4.3 mL), potassium carbonate (89.0 mg, 0.642 mmol) was added, and the obtained solution was stirred at room temperature for 4 hours. Water was added to the reaction solution to quench the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (213 mg, 0.507 mmol, 79%) as a white solid.

$^1$H-NMR (400 MHz, CDCl$_3$) δ: 1.49 (1H, d, J=4.4 Hz), 1.65-1.74 (2H, m), 1.90-1.98 (4H, m), 2.10 (3H, s), 2.32 (3H, s), 2.71-2.78 (2H, m), 3.74-3.81 (4H, m), 6.37 (1H, s), 6.83 (2H, d, J=9.2 Hz), 7.08 (4H, s), 7.20 (2H, d, J=9.2 Hz).

ESI-MS: m/z=421 (M+H)$^+$

Comparative Example 27

4-Methoxy-4-(1-(4-methoxyphenyl)-5-p-tolyl-1H-pyrazol-3-yl)cyclohexanol

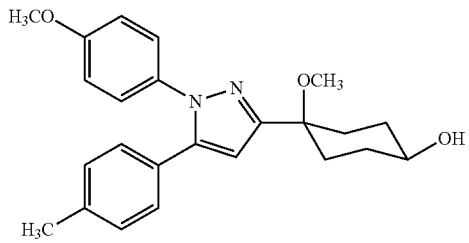

To a solution of c-4-hydroxy-4-(1-(4-methoxyphenyl)-5-(p-tolyl)-1H-pyrazol-3-yl)-cyclohexan-r-1-yl acetate (Example 57) (200 mg, 0.476 mmol) in N,N-dimethylformamide (2.4 mL), 55% sodium hydride (31.1 mg, 0.713 mmol) and methyl iodide (39.0 μL, 0.618 mmol) were added with stirring under ice-cooling. The obtained solution was stirred at room temperature for 60 hours. Water was added to the reaction solution with stirring under ice-cooling, and the resulting solution was stirred for 15 minutes, followed by extraction with ethyl acetate. The organic layer was washed with brine, dried over anhydrous sodium sulfate, and concentrated under reduced pressure. The residue was purified by flash chromatography (silica gel, n-hexane/ethyl acetate) and further purified by reprecipitation and washing (n-hexane/diethyl ether) to obtain the title compound (60.5 mg, 0.139 mmol, 29%) as a white solid.

$^1$H-NMR (400 MHz, CDCl$_3$) δ: 1.42 (1H, brs), 1.70-1.78 (2H, m), 1.84-1.95 (4H, m), 2.25-2.34 (5H, m), 3.18 (3H, s), 3.68-3.77 (1H, m), 3.81 (3H, s), 6.43 (1H, s), 6.84 (2H, d, J=8.8 Hz), 7.10 (4H, s), 7.20 (2H, d, J=8.8 Hz).

IR (KBr, cm$^{-1}$): 3407, 2937, 1516, 1457, 1368, 1298, 1249, 1185, 1071, 1035, 969, 833.

ESI-MS: m/z=393 (M+H)$^+$

Comparative Example 28

1-(4-Fluoro-1-(4-methoxyphenyl)-5-(p-tolyl)-1H-pyrazol-3-yl)cyclohexan-cis-1,4-diol

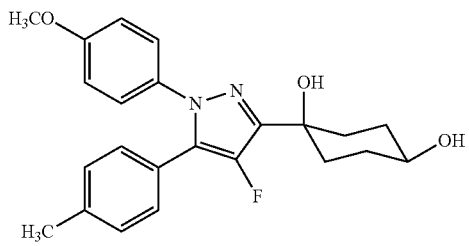

To a solution of 4-(4-fluoro-1-(4-methoxyphenyl)-5-(p-tolyl)-1H-pyrazol-3-yl)-c-4-hydroxy-cyclohexan-r-1-yl acetate (Reference Example 80) (90 mg, 0.205 mmol) in methanol (2.0 mL), potassium carbonate (142 mg, 1.03 mmol) was added, and the obtained solution was stirred at room temperature for 2 hours. Water was added to the reaction solution to quench the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain the title compound (62 mg, 0.156 mmol, 76%) as a white solid.

$^1$H-NMR (400 MHz, CDCl$_3$) δ: 1.45 (1H, s), 1.83-1.95 (4H, m), 2.06-2.08 (4H, m), 2.36 (3H, s), 2.70 (1H, s), 3.77-3.81 (4H, m), 6.83-6.86 (2H, m), 7.12-7.19 (6H, m).

ESI-MS: m/z=379 (M−OH)$^+$

Comparative Example 29

4-(4-Fluoro-1-(4-methoxyphenyl)-5-(4-tolyl)-1H-pyrazol-3-yl)-1-(N-hydroxy-N-methylcarbamoyl)-4-piperidinol

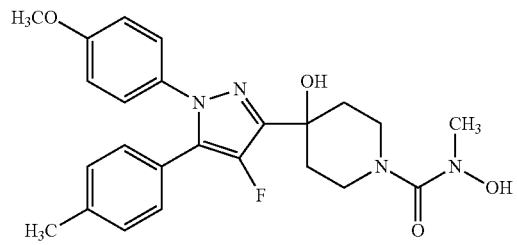

To a solution of 4-(4-fluoro-1-(4-methoxyphenyl)-5-(4-tolyl)-1H-pyrazol-3-yl)-4-piperidinol (3.61 g, 9.46 mmol) in tetrahydrofuran (946 mL), triphosgene (1.12 g, 3.78 mmol) and triethylamine (1.65 mL, 11.8 mmol) were added at 0° C., and the obtained solution was stirred at the same temperature for 40 minutes. To the reaction solution, N-methylhydroxylamine hydrochloride (988 mg, 11.8 mmol) and triethylamine (3.43 mL, 24.6 mmol) were added, and the obtained mixture was stirred at 80° C. for 3 hours. The reaction solution was cooled to room temperature, and distilled water was added to the reaction solution. The resulting solution was extracted with ethyl acetate. The organic layer was washed with 1 M hydrochloric acid, saturated sodium bicarbonate solution and brine, dried over anhydrous sodium sulfate, and concentrated under reduced pressure. The residue was purified by recrystallization (n-hexane/ethyl acetate, 80° C.) to obtain the title compound (2.96 g, 6.51 mmol, 68%) as a pale yellow solid.

$^1$H-NMR (400 MHz, CDCl$_3$) δ: 1.94-1.98 (2H, m), 2.23-2.31 (2H, m), 2.35 (3H, s), 2.86 (1H, s), 3.00 (3H, s), 3.50-3.56 (2H, m), 3.81 (3H, s), 3.92-3.95 (2H, m), 6.84-6.87 (3H, m), 7.10-7.19 (6H, m).

IR (KBr, cm$^{-1}$): 3382, 1630, 1513, 1440, 1251, 1164, 1108, 1031, 836.

ESI-MS: m/z=438 (M−OH)$^+$

Comparative Example 30

4-(3-Cyclohexyl-5-phenyl-1H-pyrazol-1-yl)-2-(hydroxymethyl)benzenesulfonamide

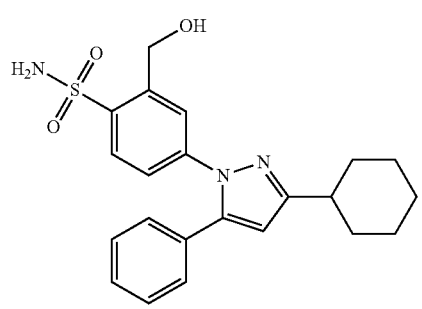

To a suspension of 4-hydrazinyl-2-(hydroxymethyl)benzenesulfonamide (224 mg, 0.884 mmol) in ethanol (4.0 mL), triethylamine (246 μL, 1.77 mmol) and 1-cyclohexyl-3-phenylpropan-1,3-dione (185 mg, 0.803 mmol) were added, and the obtained solution was stirred at 100° C. for 72 hours. Water was added to the reaction solution, and the resulting solution was extracted with ethyl acetate. The organic layer was washed with brine, dried over anhydrous sodium sulfate, and concentrated under reduced pressure. The residue was purified by flash chromatography (silica gel, n-hexane/chloroform/acetone) to obtain the title compound (51.5 mg, 0.125 mmol, 16%) as a white amorphous product.

$^1$H-NMR (400 MHz, CDCl$_3$) δ: 1.18-1.89 (8H, m), 1.98-2.09 (2H, m), 2.69-2.79 (1H, m), 3.28 (1H, br), 4.94 (2H, d, J=5.2 Hz), 5.56-5.63 (2H, m), 6.35 (1H, s), 7.05-7.38 (6H, m), 7.48-7.54 (1H, m), 7.83 (1H, d, J=8.8 Hz).

ESI-MS: m/z=412 (M+H)$^+$

Example 72

Effect on Nociceptive Pain

Using a mouse acetic acid writhing model with which nociceptive pain can be evaluated, the analgesic effect of Compound (I) was studied.

1. Experimental Method

Male ddY mice of 5 to 6 weeks old were fasted for not less than 16 hours, during which water was given ad libitum. Thereafter, the test compound solution or its vehicle was orally administered (10 mL/kg). As the vehicle of the test compound solution, dimethyl sulfoxide (hereinafter referred to as DMSO):Tween 80:distilled water (1:1:8) or 27% hydroxypropyl-β-cyclodextrin (hereinafter referred to as HP-β-CD) was used. Forty five minutes after the administration of the vehicle or test compound, 0.6% acetic acid solution (10 mL/kg) was intraperitoneally administered to induce writhing responses (behaviors such as extending the body and bending the body backward). The number of writhing responses occurred from 10 minutes after the administration of the acetic acid solution was counted for 10 minutes, and the number of writhing responses was used as an index of pain.

The mean number of writhing responses obtained in the vehicle group was defined as 100%, and the dose of the test compound with which 50% of the response was suppressed was represented as the ED$_{50}$ value.

2. Results

Results are shown in Table 10.

TABLE 10

| Compound | ED$_{50}$ (mg/kg) | Vehicle |
| --- | --- | --- |
| Example 1 | 3.78 | A |
| Example 2-A | 1.80 | A |
| Example 2-B | 1.40 | A |
| Example 3 | 6.07 | B |
| Example 6-A | 7.97 | B |
| Example 28 | 5.27 | B |
| Example 29 | 3.77 | A |
| Example 30 | 3.73 | B |
| Example 31 | 0.41 | B |
| Example 33 | 2.69 | B |
| Example 35 | 4.69 | B |
| Example 37 | 1.95 | A |
| Example 57 | 1.77 | B |
| Example 59 | 9.92 | B |
| Example 60 | 1.37 | B |
| Example 62 | 0.54 | B |
| Example 63 | 5.36 | B |
| Example 64 | 1.19 | B |
| Example 65-A | 1.44 | B |

TABLE 10-continued

| Compound | ED$_{50}$ (mg/kg) | Vehicle | |
| --- | --- | --- | --- |
| Example 67-B | 7.32 | B | |
| Example 69-A | 3.02 | A | |
| Example 70-B | 9.65 | B | |
| Example 71 | 1.58 | A | |
| Comparative Example 1 to 28 | >10 | Comparative Examples 8, 24, 26 | A |
| | | Comparative Examples 1 to 7, 9 to 23, 25, 27 | B |
| Comparative Example 30 | >10 | B | |

Vehicle A = DMSO:Tween 80:distilled water (1:1:8), vehicle B = 27% HP-β-CD

All the compounds of Examples 1, 2-A, 2-B, 3, 6-A, 28-31, 33, 35, 37, 57, 59, 60, 62~64, 65-A, 67-B, 69-A, 70-B and 71 described in Table 10 showed ED$_{50}$ values of 0.41 to 9.92 mg/kg. In terms of Comparative Examples 1 to 28, the ED$_{50}$ values were >10 mg/kg. These results indicate that Compound (I) has an excellent analgesic effect. Further, the compound of Comparative Example 30 did not cause significant reduction in the number of writhing responses even by administration of 10 mg/kg of the compound (t-test).

Example 73

Effect in Mouse Sciatic Nerve-Ligation Model

Using a mouse sciatic nerve-ligation model (Seltzer model) with which neuropathic pain can be evaluated, the analgesic effect of Compound (I) was studied.

The neuropathic pain model was prepared according to the method by Seltzer et al. Male ICR mice of 5 weeks old were anesthetized with sodium pentobarbital (70 mg/kg, i.p.), and the sciatic nerve at the femoral region of the right hind limb was exposed, followed by triply and tightly ligating the sciatic nerve under microscope such that only half thickness thereof was pressed with silk suture of 8-0 (NATSUME SEISAKUSHO), to provide Ligation group. A group wherein the sciatic nerve was exposed but not ligated was provided as a control group (Sham). In terms of evaluation of neuropathic pain (hereinafter referred to as von Frey test), mice were kept in acrylic cages (NATSUME SEISAKUSHO) placed on nets for at least 1 hour for habituation, and a filament (North Coast Medical Inc. CA, USA) which exerts a pressure of 0.16 g was used to mechanically stimulate the both plantar hind paws by pressing them with the filament 3 times for 3 seconds/time at intervals of 3 seconds. The escape behavior occurred upon application of the mechanical stimulation was scored (0: no response, 1: showed slow and slight escape behavior in response to the stimulation, 2: showed quick escape behavior without flinching (behavior of shaking legs quickly and continuously) or licking (leg-licking behavior), 3: showed quick escape behavior with flinching or licking), and the total of the scores obtained in the triplicate pressing trials was used as an index of pain. The von Frey test was carried out 7 days after the sciatic nerve ligation operation to obtain the pre value before oral administration of the test compound, and also carried out 1 hour, 2 hours and 3 hours after the oral administration to obtain values to be used as indices of the analgesic effect. To provide a positive control, gabapentin (30 mg/kg, oral administration) was used.

The results are shown in FIGS. 1 to 4 and Table 11. In FIGS. 1 to 4, the ordinate indicates the total score of the von Frey test, and a higher value indicates a stronger pain. The abscissa indicates the time (hr) after the administration of the test compound. As the vehicle of the test compound solution, 27% HP-β-CD was used in the experiments of FIG. 1, FIG. 3 and FIG. 4, and DMSO:Tween 80:distilled water (1:1:8) was used in the experiment of FIG. 2. The pharmacological effect was evaluated by statistical analysis by multiple unpaired t-test corrected with Dunnett's method using the vehicle group (Ligation+Vehicle) at each measurement time as a control. The symbols "*" in the Figures indicate statistical significance (: p<0.01, *: p<0.001).

Based on the results of the von Frey test with the compounds of Example 2-A (FIG. 1), Example 2-B (FIG. 2), Example 62 (FIG. 3) and Comparative Example 29 (FIG. 4), gabapentin and the compound of Comparative Example 29, which were positive controls, showed the strongest analgesic effect 1 hour after the oral administration, and the analgesic effect drastically decreased 3 hours after the oral administration. On the other hand, in the cases of oral administration of the compound of Example 2-A in an amount of 0.3 mg/kg, and oral administration of the compounds of Example 2-B and Example 62 in amounts of 0.3 and 1.0 mg/kg, respectively, a strong analgesic effect was maintained even 3 hours after the oral administration. From these results, it was revealed that Compound (I) having a cyclohexane skeleton is continuously effective on neuropathic pain.

As shown in Table 11, based on the results of the von Frey test carried out 1 hour after oral administration of the compounds of Example 4-B, Example 30, Example 31, Example 59, Example 64 and Example 67-B, all of these compounds significantly improved the von Frey total score compared to the vehicle group. Thus, it was revealed that these compounds are effective on neuropathic pain.

TABLE 11

| Compound | Dose (mg/kg) (n = 5 to 6) | Control group | Vehicle group | Compound-administered group | Score improvement rate % | Vehicle |
|---|---|---|---|---|---|---|
| Example 4-B | 10 | 0.8 ± 0.2 | 5.4 ± 0.4 | 2.2 ± 0.5** | 70 | A |
| Example 30 | 10 | 0.4 ± 0.2 | 5.0 ± 0.3 | 1.2 ± 0.6*** | 83 | A |
| Example 31 | 3 | 0.4 ± 0.2 | 4.8 ± 0.4 | 0.7 ± 0.5*** | 93 | B |
| Example 59 | 10 | 0.2 ± 0.2 | 4.6 ± 0.5 | 1.7 ± 0.6** | 66 | A |
| Example 64 | 1 | 0.4 ± 0.2 | 4.8 ± 0.4 | 2.3 ± 0.5* | 57 | C |
| Example 67-B | 10 | 0.8 ± 0.2 | 5.4 ± 0.4 | 0.8 ± 0.7*** | 100 | A | von Frey Total Score Observed 1 Hour after Oral Administration (mean ± standard error)

Vehicle A = DMSO:Tween 80:distilled water (1:1:8), vehicle B = 27% HP-β-CD, vehicle C = 0.5% methyl cellulose In the cases where vehicle A or B was used, the compound was administered as a test compound solution, and in the cases where Vehicle C was used, the compound was administered as a test compound suspension.

The score improvement rate was calculated as follows:

score improvement rate=100−(score of compound-administered group−score of control group)/(score of vehicle group−score of control group)×100.

The symbols "*" in the table indicate statistical significance (*: p<0.05, : p<0.01, *: p<0.001) based on comparison with the vehicle group (multiple unpaired t-test corrected with Dunnett's method).

Example 74

Effect on Mouse Model Having Pain Due to Diabetic Neuralgia

Using a mouse model having pain due to streptozotocin (hereinafter referred to as STZ)-induced diabetic neuralgia, with which diabetic neuropathic pain can be evaluated, the analgesic effect of Compound (I) was studied.

STZ (250 mg/kg) or physiological saline was intraperitoneally administered to male ICR mice of 5 weeks old, to prepare mice having diabetes and a control group thereof. The mice having diabetes herein means mice whose blood glucose level at full feeding is not less than 350 mg/dL when a small amount of blood was collected from the tail vein 6 days after administration of STZ and the blood glucose level was measured using a blood glucose meter Precision Xceed and an electrode for measurement of blood glucose Smartblue (Abbott).

Seven days after the administration of STZ, the von Frey test was carried out for the mice having diabetes as in the above-described case of evaluation of neuropathic pain, and individuals showing a total score of 5 or higher were selected as individuals having the diseased state of pain due to diabetic neuralgia. The selected individuals were divided into groups such that the total score becomes even among the groups, followed by oral administration of test compounds. One hour after the oral administration, the von Frey test was further carried out, and the obtained value was used as an index of the analgesic effect. As a positive control, pregabalin (10 mg/kg, oral administration) was used.

Figure 5:
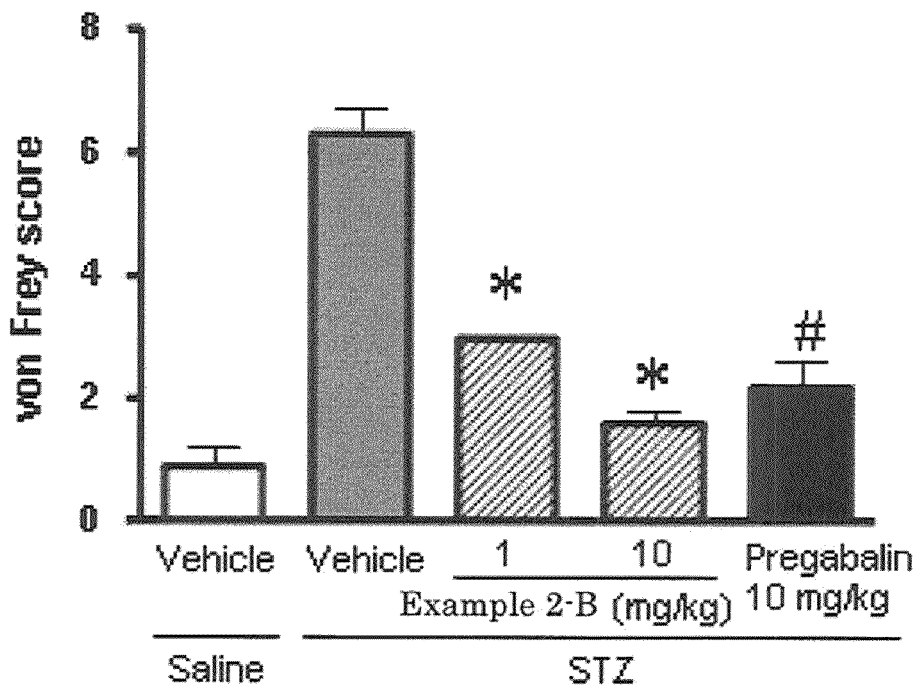
FIG. 5 is a diagram showing the effect of the compound of Example 2-B in a mouse model having pain due to streptozotocin (STZ)-induced diabetic neuralgia (oral administration).

The results are shown in FIG. 5. In FIG. 5, the ordinate indicates the total score of the von Frey test, and a higher value indicates a stronger pain. As the vehicle of the test compound suspension, 0.5% methyl cellulose was used. The pharmacological effect was evaluated by statistical analysis using the group of STZ administration+vehicle administration as a control, by Williams test for the Example 2-B-administered group and by unpaired t-test for the pregabalin-administered group. The symbols "*" and "#" in the figure indicate statistical significance based on comparison with the group of STZ administration+vehicle administration (*: p<0.025, #: p<0.05).

Based on the results of the von Frey test obtained with the compound of Example 2-B, the oral administration of 1 and 10 mg/kg of the compound significantly improved the total score of the von Frey test. It was revealed from these test results that Compound (I) is effective for pain due to diabetic neuralgia.

Example 75

Human and Mouse Liver Microsomal Stability Assay

A liver microsomal stability assay, which is known to be an in vitro assay for evaluation of the stability of a compound against hepatic metabolism, was carried out to evaluate the stability of Compound (I) against human and mouse hepatic metabolism.

A total of 4 times of experiments were carried out for the combinations of the compound of Example 2-B or the compound of Comparative Example 29 as the test compound and human liver microsomes (Xenotech) or mouse liver microsomes (Xenotech) as the liver microsomes.

The respective reagents to be used for the liver microsomal stability assay were prepared as follows. That is, an appropriate amount of D-glucose 6-phosphate disodium salt (hereinafter referred to as G6P) was dissolved in distilled water at 100 mmol/L, to prepare 100 mmol/L aqueous G6P solution. In 5 mL of distilled water, 1000 units of Glucose 6-phosphate dehydrogenase from Yeast (hereinafter referred to as G6PDH) was dissolved, to prepare 200 units/mL aqueous G6PDH solution. An appropriate amount of $MgCl_2$ was dissolved in distilled water at 100 mmol/L, to prepare 100 mmol/L aqueous $MgCl_2$ solution. To 500 mL of 200 mmol/L aqueous $K_2HPO_4$ solution, 200 mmol/L aqueous $KH_2PO_4$ solution (about 130 mL) was added, and pH was adjusted to 7.4, to prepare 200 mmol/L $KH_2PO_4$/$K_2HPO_4$ buffer pH7.4 (hereinafter referred to as 200 mmol/L PB). β-nicotinamide-adenine dinucleotide phosphate, reduced form, tetrasodium salt (hereinafter referred to as (NADPH) was dissolved in distilled water such that the NADPH content becomes 10 mmol/L based on the purity (Purity NADPH) in the assay data described in the attached document, to prepare 10 mmol/L aqueous NADPH solution.

The liver microsomal stability assay was carried out according to the following procedure. First, the reagents listed in Table 12 (excluding microsomes) were mixed together to prepare a reaction mixture, and the reaction mixture was aliquoted in 130 μL volumes to 4 wells (which play roles as the wells for the 0-minute reaction, well for the 30-minute reaction, well for the 20-minute reaction and well for the 10-minute reaction, respectively) in a 96-well tube plate (BM Equipment Co., Ltd; hereinafter referred to as plate). The entire plate was covered with a silicone cap, and the plate was subjected to preincubation by being soaked in a water bath at 37° C. for 10 minutes.

After the preincubation, 3.75 μL of 20 mg/mL microsome suspension+16.25 μL of distilled water (20 μL in total) were added to the well for the 30-minute reaction, and the plate was covered with the cap, followed by soaking the plate in a water bath at 37° C. to initiate the reaction.

Ten minutes after the beginning of the reaction, 3.75 μL of 20 mg/mL microsome suspension+16.25 μL of distilled water (20 μL in total) were added to the well for the 20-minute reaction, and 20 minutes after the beginning of the reaction, 3.75 μL of 20 mg/mL microsome suspension+16.25 μL of distilled water (20 μL in total) were added to the well for the 10-minute reaction. The reaction was further continued by keeping the plate soaked in the water bath at 37° C.

Thirty minutes after the beginning of the reaction, the plate was removed from the water bath, and 120 μL of acetonitrile was added to each well, followed by covering the plate with the cap, stirring the plate for 10 seconds with Direct Mixer, and stopping the reaction by 10 minutes of ice cooling. After the reaction was stopped, 3.75 μL of 20 mg/mL microsome suspension+16.25 μL of distilled water (20 μL in total) were added to the well for the 0-minute reaction.

TABLE 12

|  | Amount to be added (μL) | Final concentration |
|---|---|---|
| 10 mmol/L NADPH | 15.0 | 1 mmol/L |
| 100 mmol/L G6P | 15.0 | 10 mmol/L |
| 200 units/mL G6PDH | 0.75 | 1 unit/mL |
| 100 mmol/L $MgCl_2$ | 12.0 | 8 mmol/L |

TABLE 12-continued

|  | Amount to be added (μL) | Final concentration |
|---|---|---|
| 200 mmol/L PB | 75.0 | 100 mmol/L |
| 0.05 mmol/L Test compound | 6.0 | 2 μmol/L |
| Distilled water | 6.25 |  |
| Microsomes (20 mg/mL) | 3.75 | 0.5 mg/mL |
| Distilled water | 16.25 |  |
| Total amount | 150.0 | — |

The reaction liquid in each well was centrifuged at 4° C. at 2500 rpm for 10 minutes, and the supernatant was transferred to a glass-coated microplate (TOMSIC Plate+) to begin LC/MS/MS analysis. The conditions for the LC/MS/MS analysis were as follows:

HPLC system: NANOSPACE SI-2 (Shiseido)
Column: CAPCELLPAK MG S-5 2.0 mm ID×50 mm C18 (Shiseido)
Mobile phase: 0.1% Formic acid/Acetonitrile
Flow rate: 0.4 mL/min
Gradient program: 30→80B %, 0.5 to 5 min. (Linear)
MS/MS system: API-5000 (Applied Biosystems).

For the chromatogram of the reaction liquid in each well obtained by the LC/MS/MS analysis, the peak area of the test compound was confirmed, and test compound remaining rate (%) at each reaction time t (min.) was calculated taking the peak area at the reaction time of 0 minute as 100%. The test compound remaining rate was semi-logarithmically plotted against the reaction time and fitted to Equation 1 by the least squares method, thereby calculating the elimination rate constant k (1/min.). Further, the obtained k was divided by the microsome protein concentration, to calculate hepatic intrinsic clearance $CL_{int}$ (mL/min./mg) (Equation 2).

$$\text{Substrate remaining rate} = A \times \exp(-kt) \qquad \text{Equation 1}$$

$$CL_{int} = k/\text{microsome protein concentration} \qquad \text{Equation 2}$$

The values of the hepatic intrinsic clearance obtained as a result of the total of 4 times of the liver microsomal stability assay are shown in Table 13 and Table 14. A higher hepatic intrinsic clearance indicates faster metabolism of the compound in liver microsomes.

TABLE 13

|  | Hepatic intrinsic clearance (mL/min./mg) | |
|---|---|---|
| Test compound | Mouse | Human |
| Example 2-B | 0.0168 | 0.0148 |
| Comparative Example 29 | 0.267 | 0.110 |

As shown in Table 13, the hepatic intrinsic clearance obtained by the liver microsomal stability assay using the compound of Example 2-B as the test compound was extremely smaller than that using the compound of Comparative Example 29 as the test compound. From these test results, it was revealed that Compound (I) having a cyclohexane skeleton remarkably improves the metabolic stability in liver.

Table 14 shows the results of the human liver microsomal stability assay. When compared with Comparative Example 29 in Table 13, Examples 2-A, 4-B, 28, 30, 33, 35, 59, 62, 64 and 67-B showed smaller human hepatic intrinsic clearance, indicating that the metabolic stability in liver was improved.

TABLE 14

| Test Compound | Human hepatic intrinsic clearance (mL/min/mg) | Test compound | Human hepatic intrinsic clearance (mL/min/mg) |
|---|---|---|---|
| Example 2-A | 0.0451 | Example 4-B | 0.00869 |
| Example 28 | 0.00319 | Example 30 | 0.00392 |
| Example 33 | 0.0580 | Example 35 | 0.0250 |
| Example 59 | 0.0446 | Example 62 | 0.0333 |
| Example 64 | 0.00206 | Example 67-B | 0.0127 |

Example 76

Pharmacokinetics (PK) Test

Example 2-B or Comparative Example 29 was orally administered to mice, and the plasma level after the administration was measured to study the influence of improvement of the metabolic stability in liver microsomes on the change in the plasma level of the compound.

Female CD1 (ICR) mice of 7 weeks old which had been fed ad libitum with pellets (Oriental Yeast Co., Ltd.) and tap water were fasted for 17 hours before the administration. Feeding to the mice was begun again 4 hours after the administration.

The compound of Example 2-B was dissolved in DMSO: Tween 80:distilled water (1:1:8), or the compound of Comparative Example 29 was dissolved in 27% aqueous HP-β-CD solution, to prepare each solution to be administered that contained the compound at a concentration of 0.2 mg/mL.

In the case of intravenous administration of the solution, the animal was fixed in a holder, and the administration was carried out from the tail vein without anesthesia, using a syringe with an injection needle (25 G) attached thereto. In the case of oral administration, a syringe with a feeding needle attached thereto was used without anesthesia to force the solution into the stomach.

In terms of the mice to which the solution was intravenously administered, blood was collected a total of 8 times from the jugular vein or heart 5, 15 and 30 minutes and 1, 2, 4, 8 and 24 hours after the intravenous administration. In terms of the mice to which the solution was orally administered, blood was collected a total of 8 times from the jugular vein or heart 15, 30 and 45 minutes and 1, 2, 4, 8 and 24 hours after the oral administration. Further, from the jugular vein or heart of mice to which the solution was not administered, blood was collected as a blank. The collected blood was centrifuged at 4° C. at 12000 rpm for 5 minutes, and the obtained mouse plasma and blank plasma were stored at about −20° C. until preparation of samples for analysis.

To 50 µL of a mouse plasma sample, or a mouse plasma sample appropriately diluted with the blank plasma, an internal standard solution and 150 µL of methanol were added, and the resulting mixture was stirred, followed by cooling the mixture at 4° C. for 20 minutes. In terms of calibration curve samples, blank plasma to which a standard solution for a calibration curve was added was prepared by the same process. Each sample after the cooling was centrifuged (Hitachi Koki Co., Ltd.) at 4° C. at 2000 rpm for 10 minutes, and the supernatant was transferred onto a 0.20 µm filter plate (Whatman), followed by centrifugal filtration (Hitachi Koki Co., Ltd.) at 4° C. at 2000 rpm for 10 minutes. The obtained filtrate was subjected to LC/MS/MS analysis. The conditions for the LC/MS/MS analysis were the same as those in the above-described human and mouse liver microsomal stability assay.

From the results of the LC/MS/MS analysis, a calibration curve was prepared using Analysis 1.4 (Applied Biosystems). Based on the LC/MS/MS analysis and the prepared calibration curve, the concentration in each measurement sample was calculated using Analysis 1.4. For 3 times each of the experiments by intravenous administration and oral administration, the mean plasma level at each time point was calculated, and PK analysis was carried out using the obtained values (FIG. 6 and FIG. 7; each plot indicates the mean plasma level at each time point and its ±standard deviation; i.v. indicates test data by intravenous administration; and p.o. indicates test data by oral administration). The PK parameter was calculated using WinNonlin (Pharsight) by analysis independent of the models (intravenous administration: Model 201, oral administration: Model 200). Further, the bioavailability (BA) was calculated by normalization by dividing $AUC_{0-24\ hr}$ from the time point of the intravenous administration or oral administration to the time point of the final blood collection by the dose.

Figure 6:
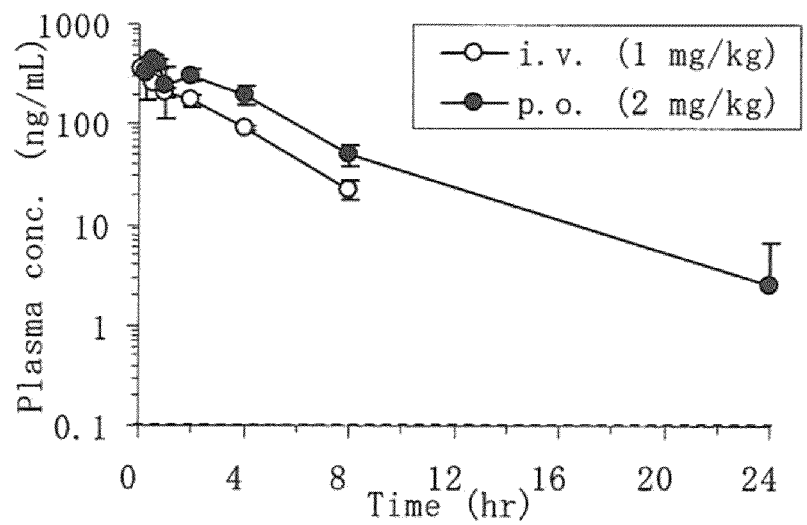
FIG. 6 is a diagram showing the change in the plasma level of the compound of Example 2-B in mice to which the compound of Example 2-B was administered.
Figure 7:
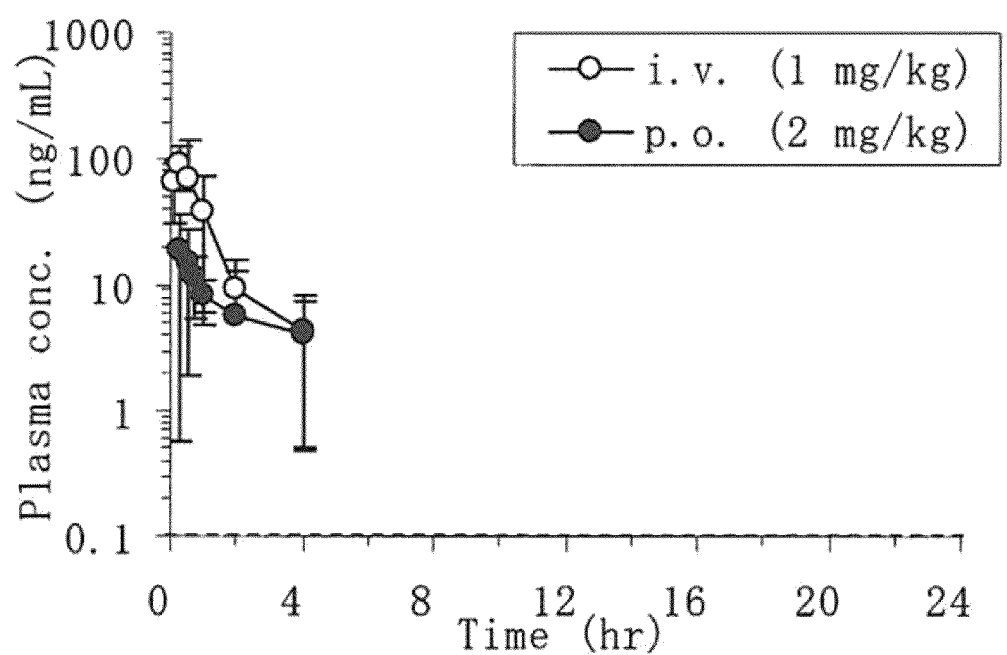
FIG. 7 is a diagram showing the change in the plasma level of the compound of Comparative Example 29 in mice to which the compound of Comparative Example 29 was administered.

As shown in FIG. 6 and FIG. 7, the mean plasma level in the mice to which the compound of Example 2-B was administered was higher than the mean plasma level in the mice to which the compound of Comparative Example 29 was administered, at all the time points. Further, BA, which indicates the ratio of oral absorption, was 88% for the compound of Example 2-B, but it was as low as 54% for the compound of Comparative Example 29. Further, the total body clearance, which indicates the rate of disappearance of a compound, was 971 mL/hr/kg for the compound of Example 2-B, but it was as high as 5672 mL/hr/kg for the compound of Comparative Example 29. From these test results, it was revealed that Compound (I) having a cyclohexane skeleton remarkably improves the metabolic stability compared to similar compounds having no cyclohexane skeleton.

Example 77

Evaluation of Safety Using Mice
1. Experimental Method

Crlj:CD1 (ICR) mice of 7 weeks old were subjected to repeated oral administration of Example 2-B or Comparative Example 29 for 5 days, and observation of clinical sign, measurement of body weight, hematology, blood chemistry, gross autopsy, measurement of organ weight and histopathology were carried out. Further, on Day 1 and Day 5 after the administration, TK measurement was carried out. Exposure to the respective compounds was confirmed.

The doses of Example 2-B were 0, 40, 200 and 1000 mg/kg/day, and those of Comparative Example 29 were 0, 30, 100 and 300 mg/kg/day. The solution to be administered was prepared using 0.5% aqueous methyl cellulose solution as a vehicle, such that the administration volume becomes 10 mL/kg.
2. Results In the animals to which Example 2-B was administered, possibilities of induction of hepatotoxicity, effects on immune organs/tissues and induction of gastrointestinal toxicity were suggested at 1000 mg/kg/day, and the no-observed-adverse-effect-level was assumed to be 200 mg/kg/day.

On the other hand, in the animals to which Comparative Example 29 was administered, possibilities of induction of hepatotoxicity and drug-induced phospholipidosis were suggested at not less than 30 mg/kg/day, and the no-observed-adverse-effect-level was assumed to be less than 30 mg/kg/day. From these results, cyclohexane derivatives (I)

represented by Example 2-B can be expected to be superior to the compound described in WO 08/105383, in view of safety.

Example 78

Prodrugs of Example 2-B were synthesized.

4-Hydroxy-4-(1-(4-methoxyphenyl)-5-p-tolyl-1H-pyrazol-3-yl)-cis-cyclohexyl dimethylcarbamate (78-A)

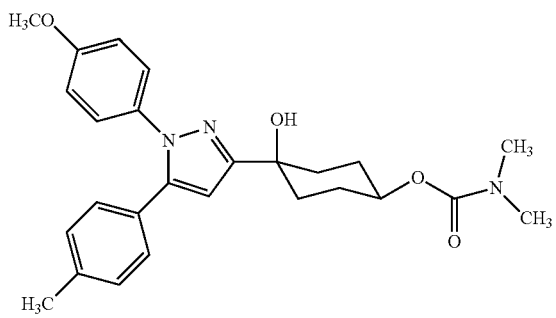

A solution of 1-(1-(4-methoxyphenyl)-5-(p-tolyl)-1H-pyrazol-3-yl)cyclohexane-cis-1,4-diol (Example 2-B) (230 mg, 0.60 mmol) in tetrahydrofuran (6.0 ml) was stirred on ice for 10 minutes. To the reaction liquid, sodium hydride (26.4 mg, 0.66 mmol) was added, and the resulting mixture was stirred at the same temperature for 20 minutes, followed by adding dimethylcarbamoyl chloride (84 µl, 0.9 mmol) dropwise thereto. The resulting mixture was stirred at room temperature for 3 hours, and brine was added to the reaction liquid, followed by extraction with ethyl acetate. The organic layer was washed with brine and dried over anhydrous sodium sulfate, followed by concentration under reduced pressure. The residue was purified by flash column chromatography (silica gel, n-hexane/ethyl acetate) to obtain the captioned compound (95.6 mg, 0.21 mmol, 35%) as a pale yellow amorphous product.

$^1$H-NMR (400 MHz, CDCl$_3$) δ: 1.93-2.04 (8H, m), 2.33 (3H, s), 2.71 (1H, s), 2.92 (6H, s), 3.80 (3H, s), 4.73-4.79 (1H, m), 6.37 (1H, s), 6.84 (2H, d, J=8.8 Hz), 7.09-7.09 (4H, m), 7.20 (2H, J=8.8 Hz).

ESI-MS: m/z=450 (M+H)$^+$

Cyclohexyl 4-hydroxy-4-(1-(4-methoxyphenyl)-5-p-tolyl-1H-pyrazol-3-yl)-cis-cyclohexyl carbonate (78-B)

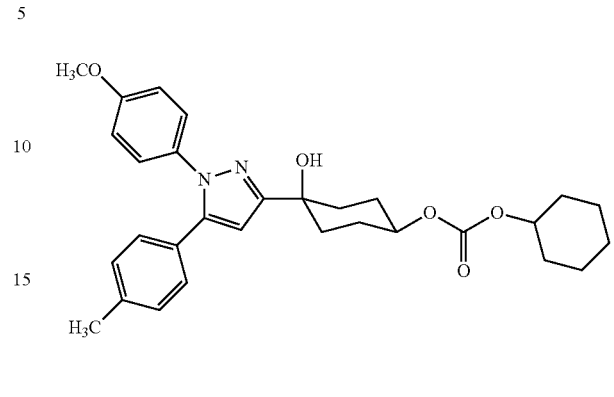

A solution of 1-(1-(4-methoxyphenyl)-5-(p-tolyl)-1H-pyrazol-3-yl)cyclohexane-cis-1,4-diol (Example 2-B) (250 mg, 0.66 mmol) in tetrahydrofuran (2.2 ml) was cooled on ice, and sodium hydride (63.4 mg, 1.45 mmol) was added thereto, followed by stirring the resulting mixture at the same temperature for 10 minutes. Cyclohexyl 1-iodoethyl carbonate (354 mg, 1.18 mmol) was then added to the mixture, and the resulting mixture was stirred at room temperature for 12 hours. To the reaction liquid, brine was added, and the resulting mixture was extracted with ethyl acetate. The organic layer was washed with brine and dried over anhydrous sodium sulfate, followed by concentration under reduced pressure. The residue was purified by flash column chromatography (silica gel, n-hexane/ethyl acetate) to obtain the captioned compound (161 mg, 0.29 mmol, 44%) as a white amorphous product.

$^1$H-NMR (400 MHz, CDCl$_3$) δ: 1.23-1.28 (4H, m), 1.31-1.40 (2H, m), 1.44-1.56 (4H, m), 1.70-1.79 (4H, m), 1.93-2.08 (4H, m), 2.32 (3H, s), 2.82 (1H, s), 3.79 (3H, s), 4.57-4.64 (1H, m), 4.67-4.71 (1H, m), 6.38 (1H, s), 6.84 (2H, d, J=8.4 Hz), 7.08-7.08 (4H, m), 7.19 (2H, J=8.4 Hz).

ESI-MS: m/z=505 (M+H)$^+$

By the same procedure as described above, the following compounds were prepared.

TABLE 15-1

| Example | Structural Formula | Compound Data |
|---------|-------------------|---------------|
| 78-C | (structure shown) | $^1$H-NMR(400 MHz, CDCl3) δ: 1.32 (3H, t, J = 8.0 Hz), 1.97-2.09 (8H, m), 2.33 (3H, s), 2.62 (1H, s), 3.80 (3H, s), 4.20 (2H, q, J = 8.0 Hz), 4.69-4.71 (1H, m), 6.37 (1H, s), 6.84 (2H, d, J = 8.8 Hz), 7.09-7.09 (4H, m), 7.20 (2H, J = 8.8 Hz). ESI-MS: m/z = 451 (M + H)$^+$ |

TABLE 15-1-continued

| Example | Structural Formula | Compound Data |
|---|---|---|
| 78-D | | $^1$H-NMR (400 MHz, CDCl$_3$) δ: 1.21 (9H, s), 1.92-2.06 (9H, m), 2.33 (3H, s), 3.80 (3H, s), 4.80-4.86 (1H, m), 6.38 (1H, s), 6.84 (2H, d, J = 8.4 Hz), 7.09-7.09 (4H, m), 7.20 (2H, J = 8.4 Hz). ESI-MS: m/z = 463 (M + H)$^+$ |

Succinic acid mono-4-hydroxy-4-(1-(4-methoxyphenyl)-5-p-tolyl-1H-pyrazol-3-yl)-cis-cyclohexyl ester (78-E)

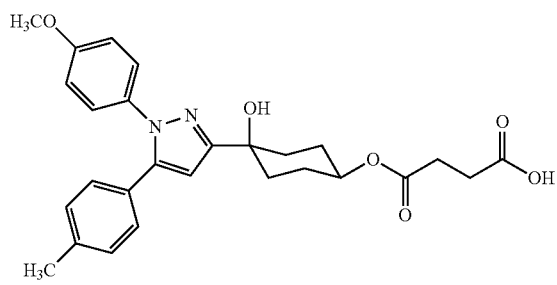

To a solution of 1-(1-(4-methoxyphenyl)-5-(p-tolyl)-1H-pyrazol-3-yl)cyclohexane-cis-1,4-diol (Example 2-B) (250 mg, 0.66 mmol) in DMF (3.3 ml), sodium hydride (63.4 mg, 1.45 mmol) was added, and the resulting mixture was stirred for 30 minutes. Succinic anhydride (99 mg, 0.99 mmol) was then added thereto, and the resulting mixture was stirred for 12 hours, followed by adding 1 M-hydrochloric acid and ethyl acetate to the reaction liquid and extraction with ethyl acetate. The organic layer was washed with brine and dried over anhydrous sodium sulfate, followed by concentration under reduced pressure. The residue was purified by flash column chromatography (silica gel, n-hexane/ethyl acetate) to obtain the captioned compound (87.0 mg, 0.18 mmol, 28%) as a white amorphous product.

$^1$H-NMR (400 MHz, CDCl$_3$) δ: 1.86-1.88 (2H, m), 1.96-2.02 (4H, m), 2.08-2.11 (3H, m), 2.32 (3H, s), 2.58-2.64 (4H, m), 3.81 (3H, s), 4.82-4.88 (1H, m), 6.38 (1H, s), 6.84 (2H, d, J=8.0 Hz), 7.09-7.09 (4H, m), 7.18 (2H, J=8.0 Hz).

ESI-MS: m/z=479 (M+H)$^+$

Cyclohexyl (4-hydroxy-4-(1-(4-methoxyphenyl)-5-(p-tolyl)-1H-pyrazol-3-yl)-cis-cyclohexyl-oxy)ethyl carbonate (78-F)

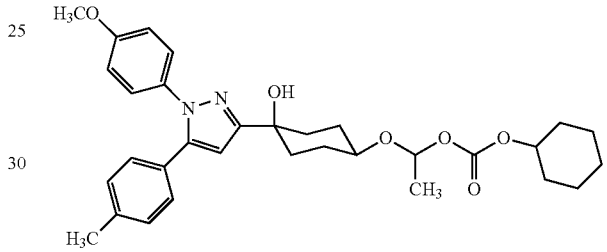

To a solution of 1-(1-(4-methoxyphenyl)-5-(p-tolyl)-1H-pyrazol-3-yl)cyclohexane-cis-1,4-diol (Example 2-B) (400 mg, 1.05 mmol) in dichloroethane (5.4 ml), cyclohexyl 1-iodoethyl carbonate (567 mg, 1.90 mmol), diisopropylethylamine (460 µl, 2.64 mmol) and silver chloride (273 mg, 1.90 mmol) were added, and the resulting mixture was stirred at 80° C. for 12 hours, followed by allowing the mixture to cool to room temperature and filtering the reaction liquid through Celite. To the filtrate, 1 M-hydrochloric acid and ethyl acetate were added, and the resulting mixture was extracted with ethyl acetate. The organic layer was washed with brine and dried over anhydrous sodium sulfate, followed by concentration under reduced pressure. The residue was purified by flash column chromatography (silica gel, n-hexane/ethyl acetate) to obtain the captioned compound (31.9 mg, 0.058 mmol, 5.1%) as a white amorphous product.

$^1$H-NMR (400 MHz, CDCl$_3$) δ: 1.15-1.34 (9H, m), 1.48-1.65 (4H, m), 1.83-1.98 (8H, m), 2.33 (3H, s), 2.49 (1H, s), 3.52-3.58 (1H, m), 3.64-3.71 (1H, m), 3.81 (3H, s), 4.92 (1H, q, J=5.2 Hz), 6.39 (1H, s), 6.84 (2H, d, J=8.8 Hz), 7.09-7.09 (4H, m), 7.19 (2H, J=8.8 Hz).

ESI-MS: m/z=549 (M+H)$^+$

By the same procedure as described above, the following compounds were prepared.

TABLE 15-2

| Example | Structural Formula | Compound Data |
|---|---|---|
| 78-G | (structure) | $^1$H-NMR (400 MHz, CDCl$_3$) δ: 1.26 (3H, t, J = 5.0 Hz), 1.33 (3H, d, J = 4.8 Hz), 1.86-2.01 (8H, m), 2.33 (3H, s), 2.49 (1H, s), 3.49-3.53 (1H, m), 3.65-3.70 (2H, m), 3.80 (3H, s), 4.84 (1H, q, J = 4.8 Hz), 6.39 (1H, s), 6.84 (2H, d, J = 8.0 Hz), 7.09-7.09 (4H, m), 7.19 (2H, J = 8.0 Hz). ESI-MS: m/z = 495 (M + H)$^+$ |
| 78-H | (structure) | $^1$H-NMR (400 MHz, CDCl$_3$) δ: 1.23 (9H, s), 1.89-2.00 (6H, m), 2.05-2.08 (2H, m), 2.33 (3H, s), 2.48 (1H, s), 3.67-3.71 (1H, m), 3.81 (3H, s), 5.39 (2H, s), 6.38 (1H, s), 6.84 (2H, d, J = 9.2 Hz), 7.09-7.09 (4H, m), 7.19 (2H, J = 9.2 Hz). ESI-MS: m/z = 493 (M + H)$^+$ |

4-Hydroxy-4-(1-(4-methoxyphenyl)-5-(p-tolyl)-1H-pyrazol-3-yl)-cis-cyclohexyl 2-aminoacetate (78-I)

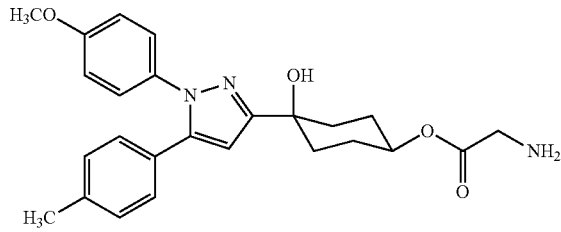

To a solution of 4-hydroxy-4-(1-(4-methoxyphenyl)-5-(p-tolyl)-1H-pyrazol-3-yl)-cis-cyclohexyl 2-benzyloxycarbonylaminoacetate (Reference Example 97) (33.2 mg, 0.058 mmol) in methanol (2.00 mL), 10% palladium/carbon (6.16 mg, 50 wt %) was added at room temperature, and the resulting mixture was stirred for 14 hours under hydrogen atmosphere. The reaction liquid was filtered through Celite, and the filtrate was concentrated under reduced pressure. The residue was purified by flash column chromatography (NH silica gel, chloroform/methanol) to obtain the captioned compound (18.4 mg, 0.042 mmol, 73%) as a colorless amorphous product.

$^1$H-NMR (400 MHz, CDCl$_3$) δ: 1.58-1.82 (2H, m), 1.88-2.12 (9H, m), 2.33 (3H, s), 3.43 (2H, s), 3.81 (3H, s), 4.88-4.94 (1H, m), 6.37 (1H, s), 6.83-6.87 (2H, m), 7.09-7.11 (4H, m), 7.18-7.22 (2H, m).

ESI-MS: m/z=436 (M+H)$^+$

By the same procedure as described above, the following compound was prepared.

TABLE 15-3

| Example | Structural Formula | Compound Data |
|---|---|---|
| 78-J | (structure) | $^1$H-NMR (400 MHz, CDCl$_3$) δ: 0.93 (3H, d, J = 6.4 Hz), 1.00 (3H, d, J = 6.4 Hz), 1.90-2.10 (9H, m), 2.34 (3H, s), 3.31 (1H, d, J = 8.0 Hz), 3.81 (3H, s), 4.88-4.94 (1H, s), 6.36, (1H, s), 6.83-6.87 (2H, m), 7.09-7.11 (4H, m), 7.18-7.22 (2H, m). ESI-MS: m/z = 460 (M − OH)$^+$ |

(S)-4-Hydroxy-4-(1-(4-methoxyphenyl)-5-(p-tolyl)-1H-pyrazol-3-yl)-cis-cyclohexyl 2-amino-3-methylbutanoate (78-K)

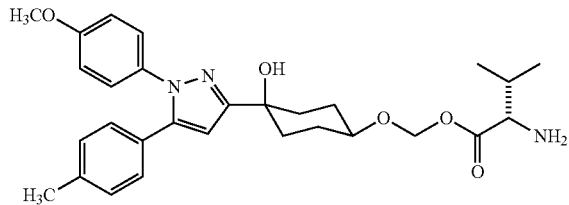

To a mixed solution of (S)-4-hydroxy-4-(1-(4-methoxyphenyl)-5-(p-tolyl)-1H-pyrazol-3-yl)-cis-cyclohexyl 2-benzyloxycarbonylamino-3-methylbutanoate (Reference Example 99) (122 mg, 0.190 mmol) in dioxane/ethanol (2.00 mL/2.00 mL), 2,2'-bipyridyl (15.0 mg, 0.096 mmol) and 10% palladium/carbon (49.0 mg, 40 wt %) was added at room temperature, and the resulting mixture was stirred for 14 hours under hydrogen atmosphere. The reaction liquid was filtered through Celite, and the filtrate was concentrated under reduced pressure. The residue was purified by flash column chromatography (silica gel, chloroform/methanol) to obtain the captioned compound (38.6 mg, 0.076 mmol, 40%) as a colorless amorphous product.

$^1$H-NMR (400 MHz, CDCl$_3$) δ: 0.92 (3H, d, J=6.8 Hz), 1.02 (3H, d, J=6.8 Hz), 1.90-2.12 (9H, m), 2.34 (3H, s), 3.32-3.34 (1H, m), 3.67-3.76 (1H, m), 3.81 (3H, s), 5.41 (1H, d, J=6.4 Hz), 5.47 (1H, d, J=6.4 Hz), 6.38, (1H, s), 6.83-6.87 (2H, m), 7.09-7.12 (4H, m), 7.18-7.22 (2H, m).

ESI-MS: m/z=490 (M–OH)$^+$

4-Hydroxy-4-(1-(4-methoxyphenyl)-5-(p-tolyl)-1H-pyrazol-3-yl)-cis-cyclohexyl dihydrogen phosphate (78-L)

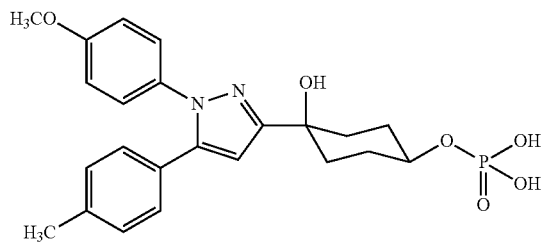

To a mixed solution of dibenzyl 4-hydroxy-4-(1-(4-methoxyphenyl)-5-(p-tolyl)-1H-pyrazol-3-yl)-cis-cyclohexyl phosphate (Reference Example 100) (251 mg, 0.393 mmol), methanol (2.6 mL) and ethyl acetate (2.6 mL), 10% palladium/carbon (41.8 mg, 50 wt %) was added, and the resulting mixture was stirred under hydrogen atmosphere at room temperature for 2.5 hours. The reaction liquid was filtered through Celite, and the filtrate was concentrated under reduced pressure. The residue was recrystallized from dichloromethane/diethyl ether to obtain the captioned compound (97.2 mg, 0.212 mmol, 54%) as a white solid.

$^1$H-NMR (400 MHz, DMSO-d$_6$) δ: 1.68-1.98 (8H, m), 2.28 (3H, s), 3.76 (3H, s), 4.13 (1H, br), 4.92 (1H, br), 6.53 (1H, s), 6.91-6.95 (2H, m), 7.08-7.17 (6H, m).

ESI-MS: m/z=459 (M+H)$^+$

Industrial Applicability

The cyclohexane derivative or a pharmaceutically acceptable salt thereof or a prodrug thereof can exert an analgesic action against nociceptive pain, neuropathic pain and diabetic neuropathic pain, and has less side effects, so that it may be used as a pharmaceutical for a wide range of pain symptoms.

The invention claimed is:

1. A cyclohexane derivative represented by Formula (I):

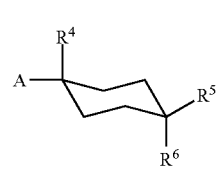

(I)

wherein

A represents a substituent represented by Formula (IIa) or (IIb):

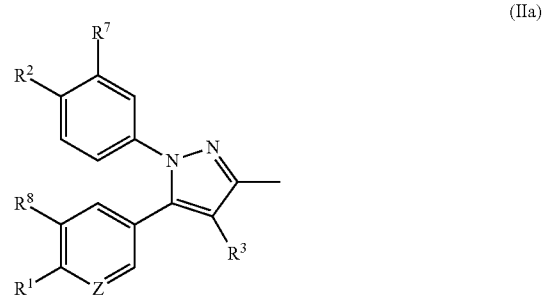

(IIa)

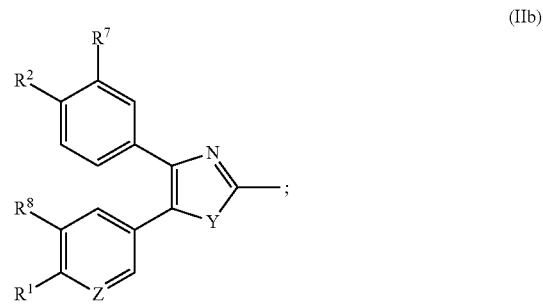

(IIb)

R$^1$ and R$^2$ each independently represent a hydrogen atom, chlorine atom, C$_1$-C$_3$ haloalkyl, C$_1$-C$_4$ alkyl, C$_1$-C$_4$ alkoxy or cyano;

R$^3$ represents a hydrogen atom or chlorine atom;

R$^4$ represents a fluorine atom, hydroxymethyl or hydroxyl;

R$^5$ and R$^6$ each independently represent a hydrogen atom, fluorine atom, C$_1$-C$_3$ haloalkyl, carboxyl, methoxycarbonyl, ethoxycarbonyl, C$_1$-C$_4$ alkoxy, hydroxyl or C$_2$-C$_5$ alkylcarbonyloxy, or R$^5$ and R$^6$ may together form an oxo group;

R$^7$ and R$^8$ each independently represent a hydrogen atom or fluorine atom;

Y represents an oxygen atom or sulfur atom; and

Z represents a nitrogen atom or methane or a pharmaceutically acceptable salt thereof or a prodrug thereof.

2. A cyclohexane derivative represented by Formula (I):

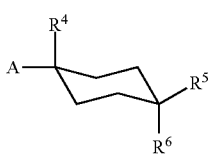

wherein

A represents a substituent represented by Formula (IIc) or (IId):

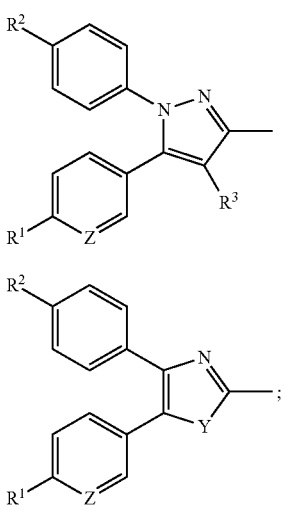

$R^1$ and $R^2$ each independently represent a hydrogen atom, chlorine atom, $C_1$-$C_3$ haloalkyl, $C_1$-$C_4$ alkyl or $C_1$-$C_4$ alkoxy;
$R^3$ represents a hydrogen atom or chlorine atom;
$R^4$ represents a fluorine atom, hydroxymethyl or hydroxyl;
$R^5$ and $R^6$ each independently represent a hydrogen atom, fluorine atom, $C_1$-$C_3$ haloalkyl, carboxyl, $C_1$-$C_4$ alkoxy, hydroxyl or $C_2$-$C_5$ alkylcarbonyloxy, or $R^5$ and $R^6$ may together form an oxo group;
Y represents an oxygen atom or sulfur atom; and
Z represents a nitrogen atom or methane
or a pharmaceutically acceptable salt thereof or a prodrug thereof.

3. The cyclohexane derivative according to claim 1, or a pharmaceutically acceptable salt thereof or a prodrug thereof, wherein $R^1$ and $R^2$ each independently represent trifluoromethyl methyl or methoxy.

4. The cyclohexane derivative according to claim 1, or a pharmaceutically acceptable salt thereof or a prodrug thereof, wherein $R^3$ represents a hydrogen atom.

5. The cyclohexane derivative according to claim 1, or a pharmaceutically acceptable salt thereof or a prodrug thereof, wherein $R^4$ represents hydroxymethyl or hydroxyl.

6. The cyclohexane derivative according to claim 1, or a pharmaceutically acceptable salt thereof or a prodrug thereof, wherein $R^5$ and $R^6$ each independently represent a hydrogen atom, fluorine atom, trifluoromethyl, carboxyl, methoxy, hydroxyl or acetyloxy, or $R^5$ and $R^6$ may together form an oxo group.

7. The cyclohexane derivative according to claim 2, or a pharmaceutically acceptable salt thereof or a prodrug thereof, wherein $R^1$ and $R^2$ each independently represent trifluoromethyl, methyl or methoxy.

8. The cyclohexane derivative according to claim 2, or a pharmaceutically acceptable salt thereof or a prodrug thereof, wherein $R^3$ represents a hydrogen atom.

9. The cyclohexane derivative according to claim 2, or a pharmaceutically acceptable salt thereof or a prodrug thereof, wherein $R^4$ represents hydroxymethyl or hydroxyl.

10. The cyclohexane derivative according to claim 2, or a pharmaceutically acceptable salt thereof or a prodrug thereof, wherein $R^5$ and $R^6$ each independently represent a hydrogen atom, fluorine atom, trifluoromethyl, carboxyl, methoxy, hydroxyl or acetyloxy, or $R^5$ and $R^6$ may together form an oxo group.

* * * * *